United States Patent [19]

Carganico et al.

[11] Patent Number: 5,990,142
[45] Date of Patent: Nov. 23, 1999

[54] BENZOPYRAN DERIVATIVES HAVING LEUKOTRIENE-ANTAGONISTIC ACTION

[75] Inventors: Germano Carganico, Piode, Italy; David Mauleon Casellas, Rubi, Spain; Jaime Pascual Avellana, L'Hospitalet del Llobregat, Spain; M. Luisa Garcia Perez, El Masnou, Spain; Albert Palomer Benet, Girona, Spain

[73] Assignee: Laboratorios Menarini S.A., Badalona, Spain

[21] Appl. No.: 09/142,922

[22] PCT Filed: Mar. 20, 1997

[86] PCT No.: PCT/EP97/01418

§ 371 Date: Oct. 15, 1998

§ 102(e) Date: Oct. 15, 1998

[87] PCT Pub. No.: WO97/34885

PCT Pub. Date: Sep. 25, 1997

[30] Foreign Application Priority Data

Mar. 21, 1996 [ES] Spain ..................................... 9600682

[51] Int. Cl.[6] .......................... A61K 31/35; A61K 31/41; C07D 405/14; C07D 407/12
[52] U.S. Cl. .......................... 514/382; 514/456; 548/253; 549/402
[58] Field of Search ............................. 549/402; 548/253; 514/382, 456

[56] References Cited

U.S. PATENT DOCUMENTS 4,977,162 12/1990 Huang et al. ........................... 514/314

OTHER PUBLICATIONS

*Chemical Abstracts*, vol. 115, No. 17, 1991, Abs. No. 182817v, p. 874, XP002036210, JP 00 395 144 A, Ono Pharmaceutical Co., Ltd.

*Primary Examiner*—Laura L. Stockton
*Attorney, Agent, or Firm*—Griffin, Butler, Whisenhunt & Szipl, LLP

[57] ABSTRACT

The present invention relates to novel 4-oxo-4H-1-benzopyran compounds containing benzyloxymethyl, 3-phenylpropyl, or other araliphatic substituents in their 8-position. These compounds show a leukotriene-antagonistic activity. The compounds are characterized by good oral adsorption. The compounds of the present invention may be used as anti-inflammatory and antiallergic medicaments, and in the treatment of cardiovascular diseases.

19 Claims, No Drawings

BENZOPYRAN DERIVATIVES HAVING LEUKOTRIENE-ANTAGONISTIC ACTION

This application is a 371 of PCT/EP97/01418 filed Mar. 20, 1997.

The present invention relates to novel benzopyran derivatives, the pharmaceutically acceptable salts and solvates thereof and pharmaceutical compositions containing them, having a leukotriene antagonistic activity. The present invention also relates to a process for the preparation of the novel benzopyran derivatives as well as to the therapeutic use thereof.

TECHNOLOGICAL BACKGROUND

It is well known that most eicosanoids, prostaglandins, leukotrienes and related compounds derive from a fatty acid having 20 carbons and 4 unsaturations, called arachidonic acid (AA), which fundamentally esterifies the hydroxyl at the 2-position of the glycerol of the phospholipids contained in the cell membranes. AA is released from the phospholipid containing it by the action of a lipase, phospholipase $A_2$ ($PLA_2$) ("CRC Handbook of Eicosanoids and Related Lipids", vol. II, Ed. A. L. Willis, CRS Press Inc., Florida (1989)). After being released AA is metabolized in mammals mainly by two different pathways or enzyme systems. Through cyclooxygenase it produces prostaglandins and thromboxanes, the most significant being $PGE_2$ and $TxA_2$, which are directly involved in inflammation (Higgs et al. Annals of Clinical Research, 16, 287 (1984)). Through lipoxygenase it produces leukotrienes, the most important being $LTB_4$, and the peptide-leukotrienes $LTC_4$, $LTD_4$ and $LTE_4$. All of them are also involved in inflammatory reactions, exhibiting chemotactic activities, stimulating the secretion of lysosomic enzymes and playing an important role in immediate hypersensitivity reactions (Bailey and Casey, Ann. Rep. Med. Chem., 17, 203 (1982)). Leukotriene $LTB_4$ is a strong chemotactic agent which promotes the infiltration of leukocytes and their subsequent degranulation. (Salmon et al., Prog. Drug Res., 37, 9 (1991)). It has been widely shown that $LTC_4$ and $LTD_4$ have strong constrictive action on human bronchi (Dahlen et al., Nature, 288, 484 (1980)), causing the obstruction of airways by inflammation and mucus production (Marom et al., Am. Rev. Resp. Dis., 126, 449 (1982)), being thus involved in the pathogenesis of bronchial asthma, chronic bronchitis, allergic rhinitis, etc. Peptide-leukotrienes also bring about a blood extravasation caused by the increase of vascular permeability (Camp et al., Br. J. Pharmacol., 80, 497 (1883)) and are involved in some inflammatory diseases such as atopic eczema and psoriasis. On the other hand, several effects of peptide-leukotrienes on human cardiovascular system have been observed; they are mainly involved in the pathogenesis of the ischaemic cardiopathy. This relationship has been confirmed by the fact that coronary arteries can produce these mediators (Piomelli et al., J. Clin. Res., 33, 521A (1985)). These effects, together with the strong contractions observed in heart tissue caused by $LTC_4$ and $LTD_4$, suggest that these mediators might contribute to other cardiovascular disorders, such as coronary spasm, heart anaphylaxis, cerebral oedema and endotoxic shock.

From what said above it follows that the control of the biological activity of leukotrienes through compounds which inhibit their release or antagonize their effects, represents a new rational approach to the prevention, elimination or improvement of different allergic, anaphylactic, inflammatory and thrombotic conditions, in which such mediators are involved.

In literature some compounds have been described that can be considered as structurally related to the compounds of the present invention, having moreover an inhibitory action on leukotrienes. Toda M. et al. described N-[4-oxo-2-(1H-5-tetrazolyl)-4H-1-benzopyran-8-yl]-4-(4-phenylbutoxy)benzamide and the derivatives thereof (EP 173,516) as strong leukotriene antagonists. All these derivatives have an amide or thioamide group in their structure as a bridge between a lipophilic moiety and a carbocycle containing an acid moiety. Therefore, the compounds disclosed in the present invention, besides other functional groups as bridges between other lipophilic and polar moieties, can have amides as well, in any case such derivatives being not included within the general formula of the patent of Toda et al. On the other hand, the derivatives of the present invention show the advantage of a very high oral bioavailability thanks to their metabolic and/or chemical stability.

On the other hand, Huang F. C. et al. (U.S. Pat. No. 4,977,162 and U.S. Pat. No. 5,082,849) described 4-oxo-7-[[3-(2-quinolinylmethoxy)phenyl]methyloxy]-2-(1H-5-tetrazolyl)-4H-1-benzopyran and the derivatives thereof as potent leukotriene antagonists. All of said compounds are quinoline derivatives containing ethers, thioethers, sulfoxides, sulfones, amides, ketones, vinylenes and amines as bridges between the chromane heterocycle or equivalent with an acid function and the quinoline-containing lipophilic moiety. Therefore such compounds differ from those of the present invention in that they contain a quinoline within their general formulae, which heterocycle is never present in the general formulae and claims of the present invention.

However, the obtention of compounds with high leukotriene antagonistic activity and good oral bioavailability is still an unresolved problem in a number of antagonists up to now. The present invention provides a series of novel compounds that exhibit the above mentioned antagonistic action, that show a good oral adsorption and are useful in therapy.

DISCLOSURE OF THE INVENTION

The present invention provides novel benzopyran derivatives of general formula I,

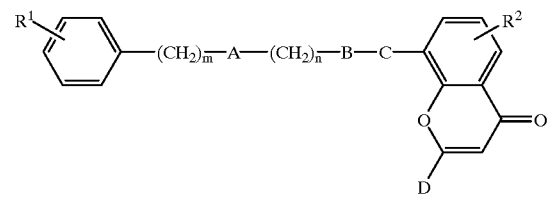

I
wherein:
A is an oxygen or sulfur atom or a methylene group;
B can be:
a) a benzofused heterocycle

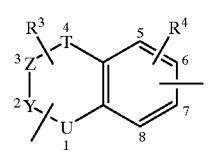

wherein:

U is an oxygen or sulfur atom or a NR⁵ group, wherein R⁵ is hydrogen or $(C_1-C_4)$-alkyl, the R⁵ group being optionally substituted by the substituent containing A when said substituent is bound to the 1-position of the benzofused heterocycle;

Z and Y represent two carbon atoms linked together by a single bond or by a double bond;

T is a single bond, a methylene group or a carbonyl group; and wherein:
the substituent containing A is bound to any one of the possible 1-, 2-, 3- or 4-position of the benzofused heterocycle;
the substituent containing C is bound to the 6- or 7-position of the benzofused heterocycle;
b) a phenyl group

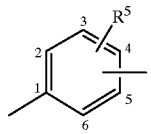

wherein the substituent containing C is bound to the phenyl group at the 3-, 4- or 5-position;

C is a diradical which represents:
a) when B is a benzofused heterocycle, a —CONR⁷—, —CSNR⁷—, —SO₂NR⁷—, —CH₂O—, —CH=CH— group, wherein R⁷ is hydrogen or methyl;
b) when B is a phenyl group, a —SO₂NR⁷—, —CH₂O—, —CH=CH— group, wherein R⁷ is hydrogen or methyl;

D is a 5-tetrazolyl or —COOR⁸ group, wherein R⁸ is hydrogen, a $(C_1-C_4)$-alkyl or a phenylalkyl group of less than 10 carbon atoms;

R¹, R², R³, R⁴ and R⁶ are independently hydrogen, halogen, $(C_1-C_4)$-alkyl, —OCH₃ or —OH;

m and n are integers from 0 to 4.

The present invention also provides a process for the preparation of the novel benzopyran derivatives, as well as the therapeutic use thereof.

The present invention also relates to the solvates and the pharmaceutically acceptable salts of the compounds of formula I and particularly the salts represented by formula Ia,

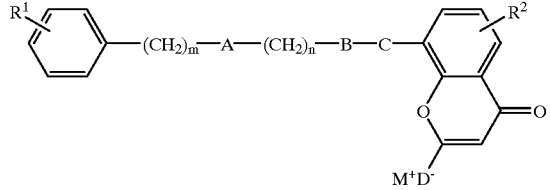

Ia
wherein M⁺ is an alkali metal cation (e.g. Na⁺, K⁺), or it represents the half amount of an alkaline-earth metal cation (e.g. ½ Ca²⁺, ½ Mg²⁺), or a cation deriving from an amine or ammonium salt (e.g. ethanolammonium, diethanolammonium, triethanolammonium, tris (hydroxymethyl)methylammonium).

The compounds of formula I can have one or more asymmetric carbons in their structure. The present invention comprises all the possible stereoisomers as well as the mixtures thereof.

Preferred compounds are those wherein R¹ and R² are hydrogen, fluorine or chlorine and D is a 5-tetrazolyl or COOR⁸ group, wherein R⁸ is hydrogen, methyl, ethyl or benzyl.

Preferred compounds also are those wherein B is a benzofused heterocycle and C is a —CO—NR⁷— or —CH=CH— group.

Further preferred compounds are those of general formula I wherein B is a phenyl group and C is a —CH=CH—, —CH₂O— or —SO₂NR⁷— group.

Particularly preferred are the compounds of formula I wherein R³ is hydrogen or methyl, C is a —CO—NR⁷— or —CH=CH— group, m and n are integers from 1 to 2, B is a benzofused heterocycle wherein Y—Z represents two carbon atoms linked by a double bond, T is a single bond or a carbonyl group and U is a NR⁵ group, wherein R⁵ is hydrogen or methyl or can be substituted by the substituent containing A, and wherein the substituent containing C is bound to the 6-position of the benzofused heterocycle and the substituent containing A is bound to the 1- or 2-position of the benzofused heterocycle.

Particularly preferred also are the compounds of formula I wherein R³ is hydrogen, R⁴ is hydrogen, fluorine, chlorine, methyl or methoxide, C is a —CONR⁷— or —CH=CH— group, m and n are integers from 1 to 2, B is a benzofused heterocycle wherein Y—Z represents two carbon atoms linked by a single bond or a double bond, T is a single bond or a methylene group and U is an oxygen atom, and wherein the substituent containing C is bound to the 6-position of the benzofused heterocycle and the substituent containing A is bound to the 2-position of the benzofused heterocycle according to the numberings described above.

Particularly preferred also are the compounds of general formula I wherein C is a —CH=CH—, —CH₂O— or —SO₂NR⁷— group, n is 0, m is an integer from 3 to 5 and B is a phenyl group in which the substituents containing A and C are linked to the phenyl group at the respective relative para position.

Most preferred compounds of formula I of the present invention are the following ones:

8-[2-(benzyloxymethyl)chromane-6-carboxamido]-4-oxo-4H-1-benzopyran-2-carboxylic acid;
N-[4-oxo-2-(1H-5-tetrazolyl)-4H-1-benzopyran-8-yl]-2-(benzyloxymethyl)chromane-6-carboxamide;
8-[2-(3-phenylpropyl)chromane-6-carboxamido]-4-oxo-4H-1-benzopyran-2-carboxylic acid;
N-[4-oxo-2-(1H-5-tetrazolyl)-4H-1-benzopyran-8-yl]-2-(3phenylpropyl)chromane-6-carboxamide;
8-[2-(benzyloxymethyl)benzofuran-5-carboxamido]-4-oxo-4H-1-benzopyran-2-carboxylic acid;
8-(2-benzyloxymethyl-2,3-dihydrobenzofuran-5-carboxamido)-4-oxo-4H-1-benzopyran-2-carboxylic acid;
N-[4-oxo-2-(1H-5-tetrazolyl)-4H-1-benzopyran-8-yl]-2-benzyloxymethyl-2,3-dihydrobenzofuran-5-carboxamide;
8-[2-(3-phenylpropyl)-2,3-dihydrobenzofuran-5-carboxamido]-4-oxo-4H-1-benzopyran-2-carboxylic acid;
N-[4-oxo-2-(1H-5-tetrazolyl)-4H-1-benzopyran-8-yl]-2-(3-phenylpropyl)-2,3-dihydrobenzofuran-5-carboxamide;
8-(2-benzylthiomethyl-2,3-dihydrobenzofuran-5-carboxamido)-4-oxo-4H-1-benzopyran-2-carboxylic acid;
8-[2-(4'-fluorobenzyloxymethyl)-2,3-dihydrobenzofuran-5-carboxamido]-4-oxo-4H-1-benzopyran-2-carboxylic acid;

N-[4-oxo-2-(1H-5-tetrazolyl)-4H-1-benzopyran-8-yl]-2-(4'-fluorobenzyloxymethyl)-2,3-dihydrobenzofuran-5-carboxamide;

8-[7-chloro-2-(3-phenylpropyl)-2,3-dihydrobenzofuran-5-carboxamido]-4-oxo-4H-1-benzopyran-2-carboxylic acid;

8-[2-(3-phenylpropyl)-2,3-dihydrobenzofuran-5-carboxamido]-6-fluoro-4-oxo-4H-1-benzopyran-2-carboxylic acid;

8-[4-chloro-2-(3-phenylpropyl)-2,3-dihydrobenzofuran-5-carboxamido]-4-oxo-4H-1-benzopyran-2-carboxylic acid;

8-[6-chloro-2-(3-phenylpropyl)-2,3-dihydrobenzofuran-5-carboxamido]-4-oxo-4H-1-benzopyran-2-carboxylic acid;

N-[4-oxo-2-(1H-5-tetrazolyl)-4H-1-benzopyran-8-yl]-1-(4phenylbutyl)-3-methylindole-5-carboxamide;

8-[[4-(4-phenylbutoxy)phenyl]methyloxy]-4-oxo-4H-1-benzopyran-2-carboxylic acid;

8-[[4-(4-phenylbutoxy)phenyl]sulfonylamino]-4-oxo-4H-1-benzopyran-2-carboxylic acid;

8-[(E)-2-[4-(4-phenylbutoxy)phenyl]ethen-1-yl]-4-oxo-4H-1-benzopyran-2-carboxylic acid;

8-[(E)-2-[4-(4-phenylbutoxy)phenyl]ethen-1-yl]-4-oxo-2(5-1H-tetrazolyl)-4H-1-benzopyran;

8-[(E)-2-[4-[4-(4-fluorophenyl)butoxy]phenyl]ethen-1-yl-]-oxo-4H-1-benzopyran-2-carboxylic acid;

8[(E)-2-[4-[4-(4-fluorophenyl)butoxy]phenyl]ethen-1-yl]-4-oxo-2-(5-1H-tetrazolyl)-4H-1-benzopyran;

8-[(E)-2-[4-(4-phenylbutoxy)-2-fluorophenyl]ethen-1-yl]-4-oxo-4H-1-benzopyran-2-carboxylic acid;

8-[(E)-2-[2-(4'-fluorobenzyloxymethyl)-2,3-dihydrobenzofuran-5-yl]ethen-1-yl]-4-oxo-4H-1-benzopyran-2-carboxylic acid;

8-[(E)-2-[2-(4'-fluorobenzyloxymethyl)-2,3-dihydrobenzofuran-5-yl]ethen-1-yl]-4-oxo-2-(5-1H-tetrazolyl)-4H-1-benzopyran;

8-[(E)-2-[4-[4-(4-chlorophenyl)butoxy]phenyl]ethen-1-yl]-4-oxo-2-(5-1H-tetrazolyl)-4H-1-benzopyran;

8-[(E)-2-[4-[4-(4-methylphenyl)butoxy]phenyl]ethen-1-yl]-4-oxo-2-(5-1H-tetrazolyl)-4H-1-benzopyran;

8-[(E)-2-[4-[4-(4-methoxyphenyl)butoxy]phenyl]ethen-1-yl]-4-oxo-2-(5-1H-tetrazolyl)-4H-1-benzopyran;

8-[(E)-2-[4-[4-[4-(iso-propyl)phenyl]butoxy]phenyl]-ethen-1-yl]-4-oxo-2-(5-1H-tetrazolyl)-4H-1-benzopyran;

8-[(E)-2-[4-[4-[4-(tert-butyl)phenyl]butoxy]phenyl]-ethen-1-yl]-4-oxo-2-(5-1H-tetrazolyl)-4H-1-benzopyran;

8-[(E)-2-[4-[4-(4-chlorophenyl)propyloxy]phenyl]ethen-1-yl]-4-oxo-2-(5-1H-tetrazolyl)-4H-1-benzopyran;

8-[(E)-2-[4-[4-(4-fluorophenyl)propyloxy]phenyl]ethen-1-yl]-4-oxo-2-(5-1H-tetrazolyl)-4H-1-benzopyran;

8-[(E)-2-[4-[4-(4-methylphenyl)propyloxy]phenyl]ethen-1-yl]-4-oxo-2-(5-1H-tetrazolyl)-4H-1-benzopyran;

8-[(E)-2-[4-[4-(4-methoxyphenyl)propyloxy]phenyl]ethen-1-yl]-4-oxo-2-(5-1H-tetrazolyl)-4H-1-benzopyran;

8-[(E)-2-[4-[4-[4-(iso-propyl)phenyl]propyloxy]phenyl]-ethen-1-yl]-4-oxo-2-(5-1H-tetrazolyl)-4H-1-benzopyran;

8-[(E)-2-[4-[4-[4-(tert-butyl)phenyl]propyloxy]phenyl]-ethen-1-yl]-4-oxo-2 -(5-1H-tetrazolyl)-4H-1-benzopyran;

as well as the carboxylic acid esters described in the examples.

According to the present invention, the compounds of general formula I are obtained through one of the following processes:

a) when in general formula I D is —COOR$^8$, a starting compound of general formula II,

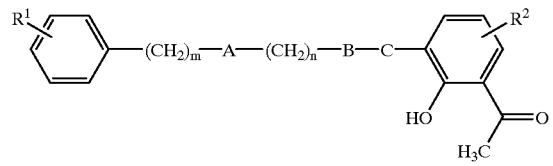

II wherein $R^1$, $R^2$, A, B, C, m and n have the above mentioned meanings, is reacted with a commercial compound III,

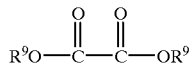

III wherein $R^9$ is thus residue $R^8$ with the exception of hydrogen, in the presence of a metal alkoxide such as sodium methoxide or ethoxide, in a suitable organic solvent such as the conjugated alcohol of the corresponding base, ethyl ether, tetrahydrofuran or mixtures thereof, at a temperature ranging from 50° to 85° C. for a time between 3 and 18 hours. The resulting compound IV,

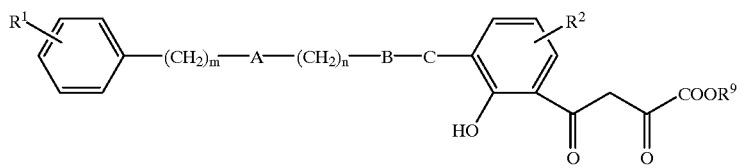

IV is subjected to a treatment with concentrated or diluted hydrochloric acid in a suitable solvent such as ethanol, methanol, tetrahydrofuran or mixtures thereof, at a temperature ranging from 25° C. to the solvent reflux, for a time between 1 and 24 hours, to obtain compound V,

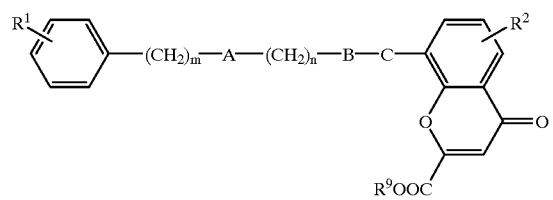

V which coincides with I wherein D is COOR$^8$ or, when D is COOH in formula I, is converted into I removing the group $R^9$ through alkali hydrolysis by treatment with a suitable base, such as lithium, sodium or potassium hydroxide, in aqueous solution in a suitable organic solvent such as methanol, ethanol or tetrahydrofuran, at a temperature ranging between 0° C. and the solvent reflux for a time from 30 min to 18 hours.

b) when in general formula I D is the 5-tetrazolyl group, a starting compound of formula VI,

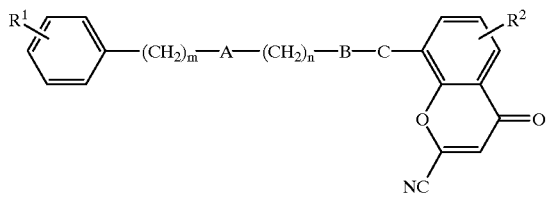

VI wherein $R^1$, $R^2$, A, B, C, m and n have the above mentioned meanings, is reacted with sodium azide in the presence of a mild acid such as ammonium chloride or pyridinium hydrochloride, in a suitable solvent such as N,N-dimethylformamide, at a temperature ranging between 25° and solvent reflux, for a time from 1 to 24 hours, thereby obtaining the compound VII,

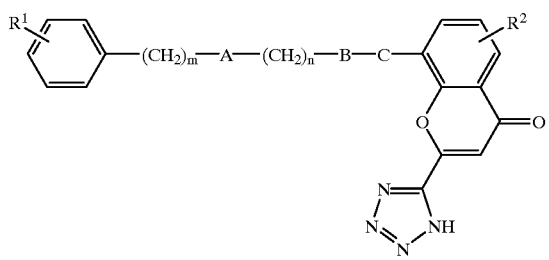

VII
which coincides with I wherein D is the 5-tetrazolyl group.

c) In an alternative process for the preparation of a compound of general formula I wherein C is —CO—$NR^7$—, a starting compound VIII,

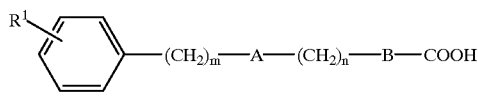

VIII
wherein $R^1$, A, B, m and n have the above mentioned meanings, is reacted with a compound IX,

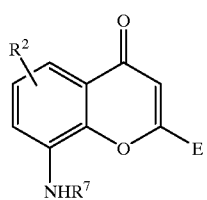

IX
wherein $R^2$ and $R^7$ have the above mentioned meanings and E can be equivalent to the group D in I or, when D in formula I is COOH, then E contains a suitable carboxy-protecting group, for example a methyl, ethyl or benzyl ester. The reaction between VIII and IX is carried out previously preparing the acid chloride of a compound VIII by reaction with an oxalyl chloride excess at a temperature ranging between 50° and 80° C. for a time from 30 minutes to 1,5 hours and subsequently reacting it with a compound IX in the presence of a base such as triethylamine, 4-dimethylaminopyridine or pyridine, in a suitable aprotic solvent such as chloroform, methylene chloride or N,N-dimethylformamide, at a temperature ranging between 0° and 40° C. and for a time from 3 to 24 hours. The resulting compound of formula X,

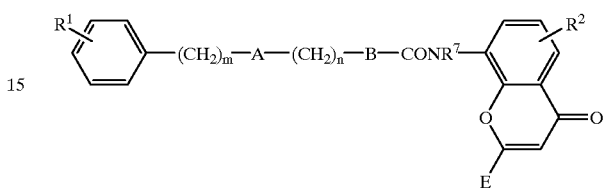

X which coincides with I wherein C is —$CONR^7$— or is converted into I wherein C is —$CONR^7$— by removing any COOH-protecting groups present in E, thus, when E is for example a methyl or ethyl ester, it can be removed by alkali hydrolysis as described above for the preparation of I wherein D=COOH starting from V.

d) In a process for the preparation of a compound of general formula I wherein C is —$CH_2O$—, a starting compound of formula XI,

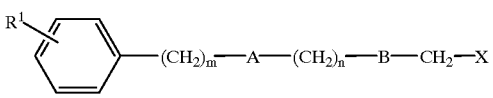

XI wherein $R^1$, A, B, m and n have the above mentioned meanings and X is a chlorine or bromine atom or an alkyl- or aryl-sulfonate group, is reacted with a compound XII,

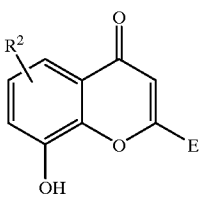

XII wherein $R^2$ and E have the above mentioned meanings, in the presence of a base such as a metal hydroxide, alkoxide or carbonate in a suitable solvent such as ethanol, methanol or N,N-dimethylformamide at a temperature ranging between 25° and 80° C. for a time from 5 to 48 hours. The resulting compound of formula XIII,

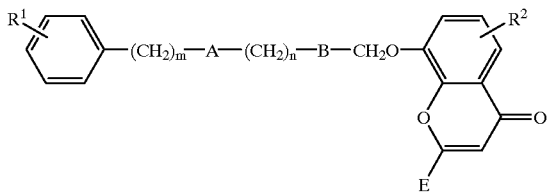

XIII which coincides with I wherein C is —CH$_2$O—, or is converted into I wherein C is —CH$_2$O— by removing any COOH-protecting groups present in E, thus, when E is for example a methyl or ethyl ester, it can be removed by alkali hydrolysis as described above for the preparation of I wherein D=COOH starting from V.

e) In a process of preparation of a compound of general formula I wherein C is —SO$_2$NR$^7$— and A is oxygen or sulfur, a starting compound XIV,

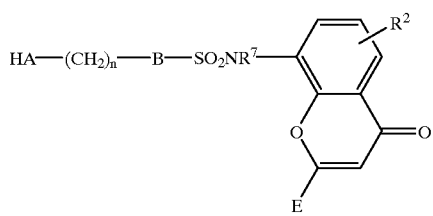

XIV wherein R$^2$, R$^7$, B, E and n have the above mentioned meanings and A is an oxygen or sulfur atom, is reacted with a compound XV,

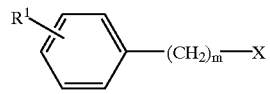

XV wherein R$^1$, X and m have the above mentioned meanings. The reaction between XIV and XV is carried out previously preparing the salt of XIV by reaction with a base suitable for the Pk$_a$ of the alcohol or thiol, such as a metal hydride, alkoxide, hydroxide or carbonate in a suitable solvent such as N,N-dimethylformamide or tetrahydrofuran at a temperature ranging between 25° and 80° C. for a time from 2 to 18 hours. The resulting compound XVI,

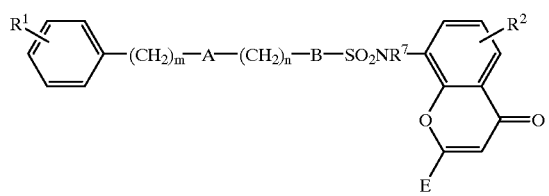

XVI which coincides with I wherein C is —SO$_2$NR$^7$— and A is oxygen or sulfur, or is converted into I wherein C is —SO$_2$NR$^7$— and A is oxygen or sulfur by removing any COOH-protecting groups present in E, thus, when E is for example a methyl or ethyl ester, it can be removed by alkali hydrolysis as described for the preparation of I wherein D=COOH starting from V.

f) The compounds of general formula I wherein C is —CSNR$^7$— are obtained starting from the compounds of formula I wherein A is —CONR$^7$— by treatment with the Lawesson's reactive in the conditions described in literature (Clausen K. et al., *Tetrahedron*, 1981, 37, 3635).

When a specific salt of general formula Ia is desired, a compound I can be treated with a base or ion exchanger suited for this purpose, according to the usual chemical methods. Thus, for example, I can be treated with sodium hydroxide or tris(hydroxymethyl)methylamine in a suitable solvent such as mixtures of water-methanol or ethanol for a time from 15 min to 2 hours, at a temperature ranging between 25° and the solvent reflux.

A starting compound of formula VI can be obtained starting from a compound of formula V through the process shown in scheme 1.

Scheme 1

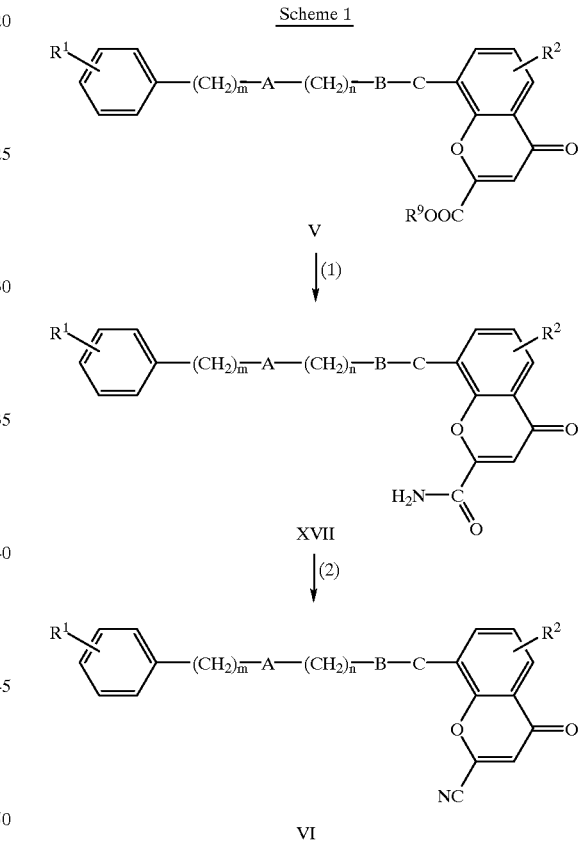

VI

In this sequence, a compound VI can be obtained by dehydration of a carboxamide XVII, for example with phosphorous oxychloride, in a solvent such as N,N-dimethylformamide, at a temperature ranging between 0° and 50° C., for a time from 3 to 24 hours (step 2). The carboxamide XVII can be obtained by aminolysis of an ester V, for example, by treatment with gaseous ammonia in a suitable solvent such as methanol, ethanol, tetrahydrofuran or a mixture thereof, at a temperature ranging from −30° to 25° C., for a time from 15 minutes to 24 hours (step 1).

A starting compound of formula IIa, i.e. of general formula II wherein C is —CO—NR$^7$—, can be obtained, for example, by reaction of a compound VIII with a compound XVIII,

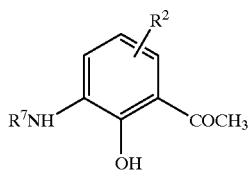

XVIII wherein $R^2$ and $R^7$ have the above mentioned meanings, following the same process as described for the preparation of compound X starting from VIII and IX.

A starting compound of formula IIb, i.e. of general formula II wherein C is —CH=CH—, can be obtained, for example, through the process shown in scheme 2.

Scheme 2

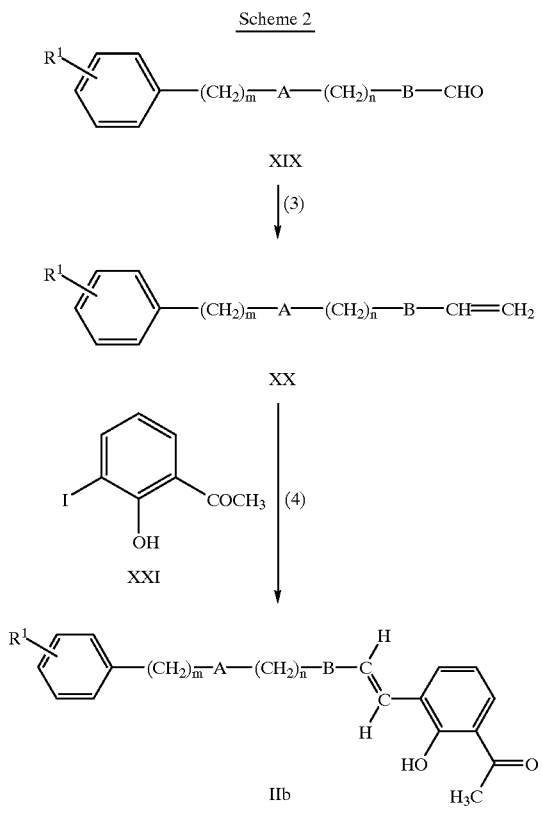

In this sequence, a starting compound XX can be obtained, for example, by Wittig reaction between a compound XIX and a commercial methylphosphonium salt in the presence of a suitable base such as butyl lithium, sodium amide or lithium bis(trimethylsilyl)amide in an inert solvent such as tetrahydrofuran or ethyl ether, at a temperature ranging between 0° and 25° C. and for a time from 45 minutes to 36 hours (step 3).

A compound IIb can be obtained by reaction of a compound XX with a compound XXI in the general conditions for the reaction of insertion of olefins catalyzed by palladium (0) complexes (Heck reaction). Then, the reaction between XX and XXI is carried out in the presence of palladium (II) acetate and triethylamine in a suitable solvent such as acetonitrile, at the temperature of the solvent reflux and for a time from 10 to 48 hours (step 4).

A starting compound of formula VIIIa, i.e. of general formula VIII wherein B is a benzofused heterocycle

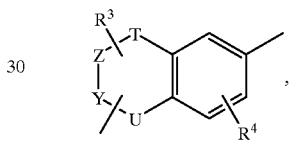

wherein $R^3$, $R^4$, Y—Z and T have the above mentioned meanings, U is an oxygen or sulfur atom and the —COOH group is bound to the benzene ring at the para position to the U atom, can be obtained, for example, starting from a compound XXII, wherein $R^3$, $R^4$, Y—Z, T and n have the above mentioned meanings and G is a hydrogen, chlorine, bromine atom or a group $COOR^9$, wherein $R^9$ represents the groups defined above, following any one of the synthetic processes represented in scheme 3.

Scheme 3

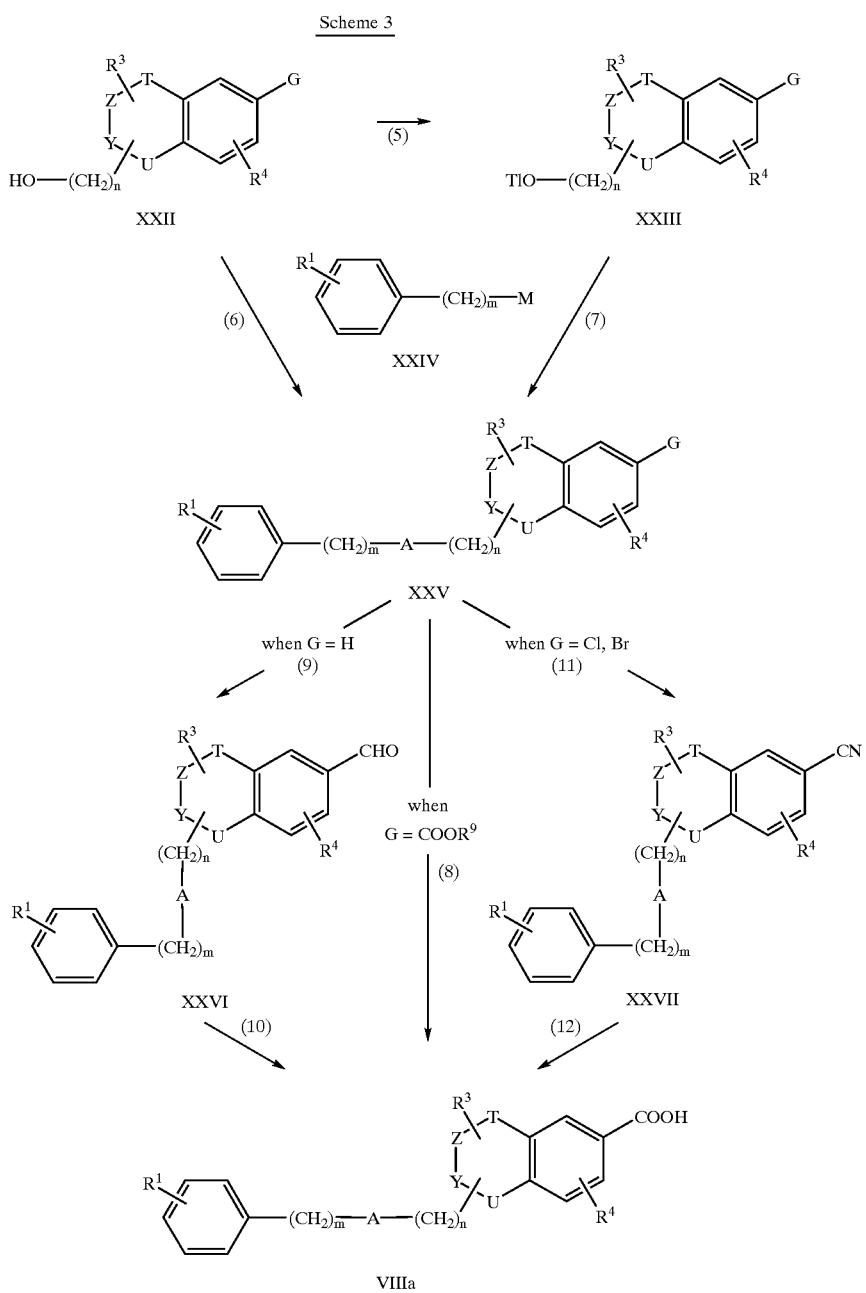

VIIIa

In this sequence a compound XXV with A=oxygen, wherein $R^1$, $R^3$, $R^4$, T, Y—Z, G, m and n represent the groups and the values defined above and U is oxygen or sulfur, is obtained, for example, subjecting a compound XXII to the action of a base such as sodium hydride or potassium hydride and subsequently reacting it with a compound XXIV, commercial or easily available through similar chemical processes, wherein $R^1$ represents the groups defined above and M is, when A is oxygen, a bromine or chlorine atom or an alkyl- or aryl-sulfonate group, in a suitable organic solvent such as benzene, N,N-dimethylformamide or tetrahydrofuran, at a temperature ranging between 0° and 25° C., for a time from 3 to 24 hours (step 6).

A compound XXV wherein A is sulfur can be obtained, for example, by reaction of a compound XXIII, wherein $R^3$, $R^4$, G and n have the above mentioned meanings and TfO represents the trifluoromethanesulfonate group, with a compound XXIV wherein M is an SH group (thiol), commercial or easily available through similar chemical processes, in the presence of a base such as potassium hydroxide, sodium methoxide or sodium ethoxide, in a suitable solvent such as ethanol, methanol, dimethylsulfoxide or N,N-dimethylformamide, at a temperature ranging of 0°–25° C., for a time from 4 to 24 hours (step 7).

A compound XXV wherein A is a methylene group is obtained by reaction of a compound XXIII, wherein $R^3$, $R^4$, G and n have the above mentioned meanings, with a compound XXIV where M is a MgBr group, in the presence of catalytic amounts of a copper (I) salt, in a suitable solvent such as ethyl ether or tetrahydrofuran, at a temperature between 0° C. and the solvent reflux and for a time from 2 to 24 hours (step 7). A compound XXIV with M =MgBr is obtained starting from a commercial bromide and magnesium, following the processes established for the preparation of Grignard reagents.

A compound XXIII is obtained starting from a compound XXII by reaction with trifluoromethanesulfonic anhydride in the presence of pyridine or triethylamine in methylene chloride, at a temperature between –10° and 25° C. and for a time from 4 to 24 hours (step 5).

A compound VIIIa can be obtained starting from XXV with G equal to the group $COOR^9$ (step 8) through alkali hydrolysis as described for the preparation of I with D =COOH starting from V.

A compound VIIIa can be obtained starting from XXV wherein G is hydrogen, subjecting it to the conditions of the Vilsmeier-Haack reaction and subsequently oxidizing the resulting aldehyde XXVI to the corresponding carboxylic acid by means, for example, of the Jones reagent. A compound XXVI is thus obtained by reaction of XXV with phosphorous oxychloride in N,N-dimethylformamide or N-methylformanilide at a temperature between 25° and 100° C. and for a time from 1 to 24 hours (step 9). The treatment of XXVI with chromium trioxide in the presence of sulfuric acid and water in a suitable solvent such as acetone at a temperature between 0° and 25° C. and for a time from 4 to 24 hours allows to obtain the compound VIIIa (step 10).

A compound VIIIa can also be obtained starting from XXV wherein G is chlorine or bromine by substitution of the halogen with a nitrile group in the conditions of the Rosenmund-von Braun reaction and subsequent hydrolysis of the nitrile group to carboxylic acid. Thereby, a compound XXVII is obtained by reaction of a compound XXV wherein G is a chlorine or bromine atom with copper (I) cyanide in a suitable high-boiling solvent such as N-methylpyrrolidinone, at a temperature ranging from 150° to 230° C., for a time from 2 to 18 hours (step 11). Alternatively, a compound XXVII where A is oxygen can be obtained reversing the order in which steps 6 and 11 are carried out. Finally, a compound VIIIa can be obtained starting from XXVII by alkali hydrolysis in the presence of sodium or potassium hydroxide in a suitable solvent such as ethanol, tetrahydrofuran or dioxane at a temperature between 25° and the solvent reflux for a time from 2 to 24 hours (step 12).

A starting compound of formula VIIIb,

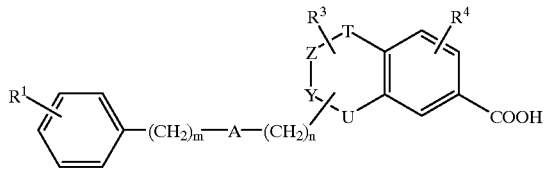

VIIIb
i.e. of general formula VIII wherein B is a benzofused heterocycle

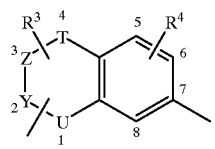

wherein $R^3$, $R^4$, Y—Z and T have the above mentioned meanings, U is an oxygen or sulfur atom and the —COOH group is bound to the 7-position of the benzofused heterocycle, can be obtained starting from a compound XXVIII,

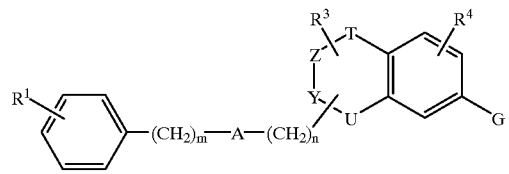

XXVIII wherein G is a chlorine or bromine atom, following the same synthetic process as that described for the preparation of VIIIa starting from XXV according to steps (11) and (12).

A compound of formula XXVIII can be obtained starting from a compound XXIX,

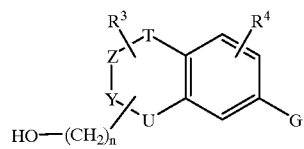

XXIX wherein $R^3$, $R^4$, T, Y—Z and n have the above mentioned meanings, U is oxygen or sulfur and G is a chlorine or bromine atom, through one of the synthetic processes described above for the preparation of XXV starting from XXII.

A starting compound of formula VIIIc, i.e. of general formula VIII where B is a benzofused heterocycle

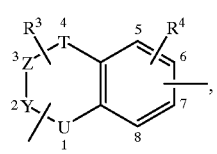

wherein U is a nitrogen atom N-substituted with the substituent containing A, T is a single bond and Y—Z is CH=CH, $R^1$, $R^3$, $R^4$, A, m and n have the above mentioned meanings and $R^3$ is a $(C_1-C_4)$-alkyl at the 3-position of the heterocycle, can be obtained, for example, following the synthetic sequence shown in scheme 4.

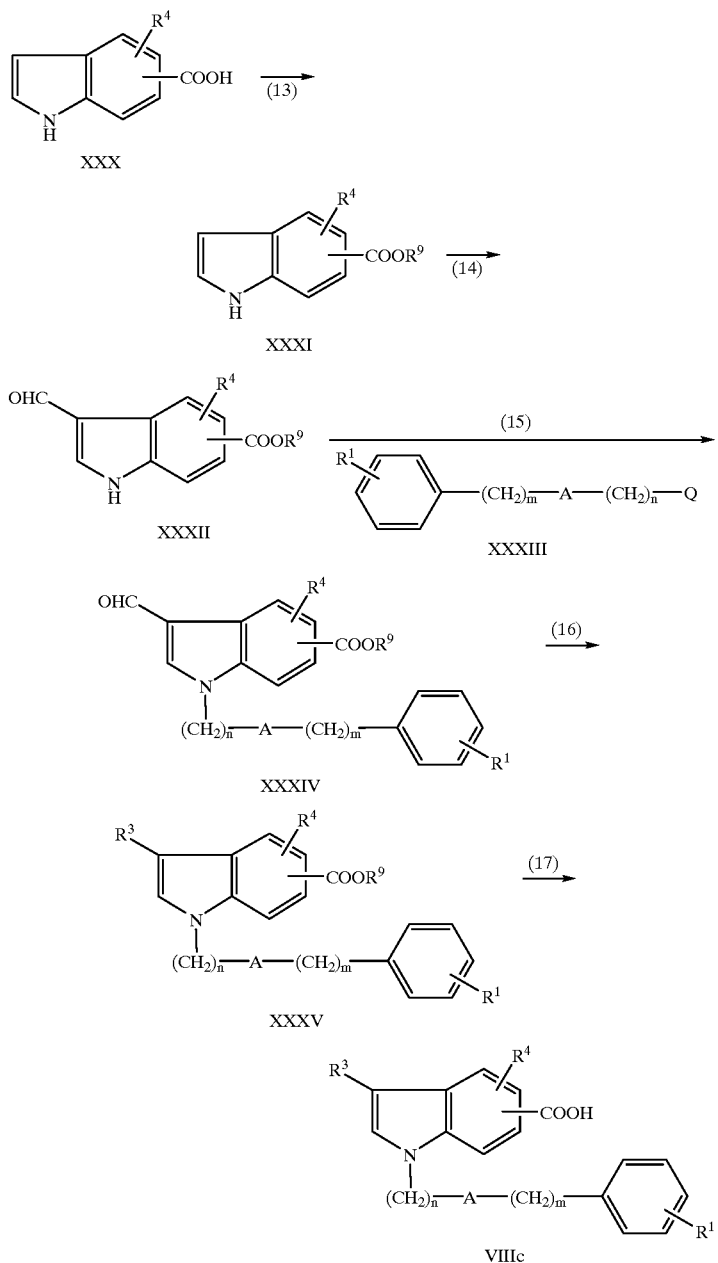

Scheme 4

In this sequence a compound XXXI can be obtained by esterification of a commercial compound XXX following established synthetic processes (step 13). Starting from XXXI, a compound XXXII can be obtained (step 14) by formulation in the (conditions usually described for the Vilsmeier-Haack reaction.

A compound XXXIV can be obtained by N-alkylation of a compound XXXII with a compound XXXIII, commercial or easily available through similar chemical transformations, wherein Q is a good leaving group such as a chlorine or bromine atom or an alkyl- or aryl-sulfonate group, in the presence of a suitable base such as potassium tert-butoxide, in a suitable solvent such as N,N-dimethylformamide, at a temperature between 25° and 100° C., for a time from 2 to 24 hours (step 15).

A compound XXXV wherein $R^3$ is methyl is obtained by reduction of the formyl group of a compound XXXIV (step 16). Said transformation can be carried out, for example, with sodium cyanoborohydride in the presence of zinc iodide in a suitable solvent, at a temperature between 25° and 90° C. and for a time from 1 to 18 h. A compound XXXV wherein $R^3$ is a $(C_1-C_4)$-alkyl group different from the methyl group can be obtained by Wittig reaction with a suitable phosphonium salt followed by reduction of the resulting olefin by hydrogenolysis under hydrogen atmosphere in the presence of a palladium catalyst and in a suitable solvent (step 16).

A compound VIIIc can be obtained starting from XXXV (step 17) through alkali hydrolysis as described for the preparation of I with D=COOH starting from V.

A starting compound of formula VIIId, i.e. of general formula VIII wherein B is a benzofused heterocycle

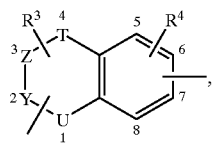

wherein U is a $NR^5$ group, T is a carbonyl group and Y—Z is a CH=CH group, $R^3$ is hydrogen, $R^5$ is a $(C_1-C_4)$-alkyl and $R^1$, $R^2$, X, m and n represent the groups and the values defined above, can be obtained, for example, following the synthetic sequence shown in scheme 5.

In this synthetic sequence a compound XXXVI can be obtained easily by reaction of the commercial Meldrum acid with carbon sulfide followed by methylation with methyl iodide according to processes described in literature. A compound XXXVIII is obtained by reaction of XXXVI with a Grignard reagent XXXVII, prepared starting from the corresponding bromide following the processes established for the preparation of organomagnesium compounds, according to the process described for the preparation of XXV with A=$CH_2$ starting from XXIII (step 18). The reaction of XXXVIII with compound XXXIX allows to prepare the 4-quinolone XL (step 19). A compound XLI is obtained by N-alkylation of a compound XL in the presence of a suitable base such as sodium or potassium hydride, in a suitable solvent such as N,N-dimethylformamide or benzene, at a temperature between 0° and 100° C. and for a time from 4 to 24 hours (step 20). The alkali hydrolysis of a compound XLI according to the processes described

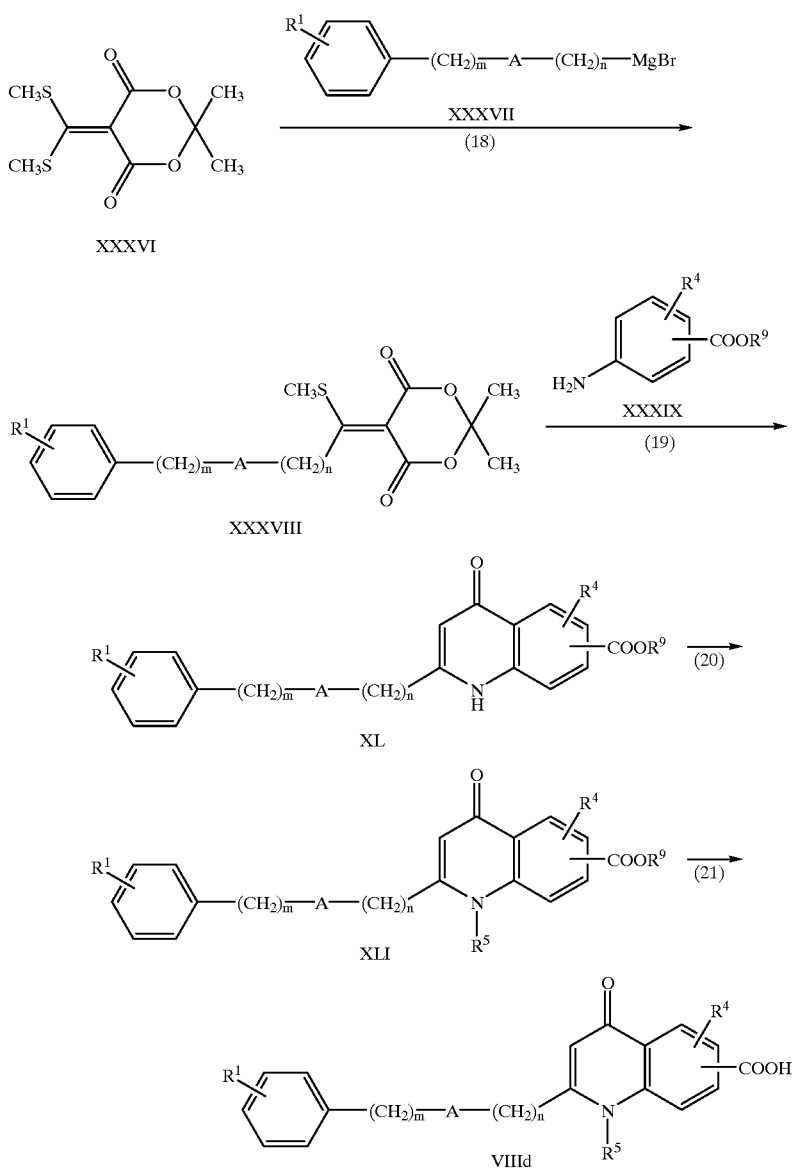

above, for example, in the preparation of I with D=COOH starting from V, allows to prepare a compound VIIId (step 21).

A starting compound of formula VIIIe,

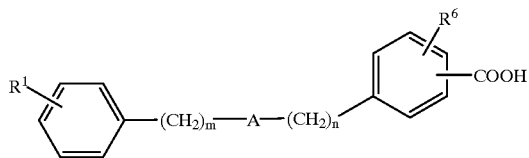

VIIIe i.e. of general formula VIII wherein B is a phenyl group substituted at any one of its free positions with a $R^6$ group, can be prepared starting from a compound XLII,

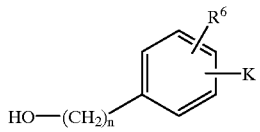

XLII commercial or easily available through similar chemical processes, wherein $R^6$ and n have the above mentioned meanings and K can be G or a formyl group (K=CHO), following one of the synthetic processes used for the preparation of VIIIa starting from XXII.

Specifically, when n is 0, a compound VIIIe can be prepared following a two-step process. The first step involves the reaction of a compound XLII wherein n=0 and k=COOR$^9$, commercial or easily available starting from similar chemical methods, with a compound XXIV wherein M is —OH in the general conditions of the Mitsunobu reaction; i.e. by reaction of XLII (with n=0) with XXIV (with M=OH) in the presence of diethyl azodicarboxylate and triphenylphosphine in a suitable solvent such as tetrahydrofuran at room temperature and for a time from 24 to 72 hours. Alternatively, the Mitsunobu reaction can be replaced by a Williamson O-alkylation reaction, subjecting a compound XLII with n=0 and K=COOR$^9$ to the action of a base such as a metal hydroxide or carbonate and subsequently reacting it with a compound XXIV wherein M is a chlorine or bromine atom or an alkyl- or aryl-sulfonate group in a suitable organic solvent such as N,N-dimethylformamide at a temperature between 0° and 100° C., for a time from 2 to 24 hours. In the second step, compound VIIIe is obtained by hydrolysis of the ester obtained in the preceding step, following the process described for the preparation of I with D=COOH starting from V.

The starting compounds XI and XIX can be obtained, for example, following the synthetic processes shown in scheme 6.

Scheme 6

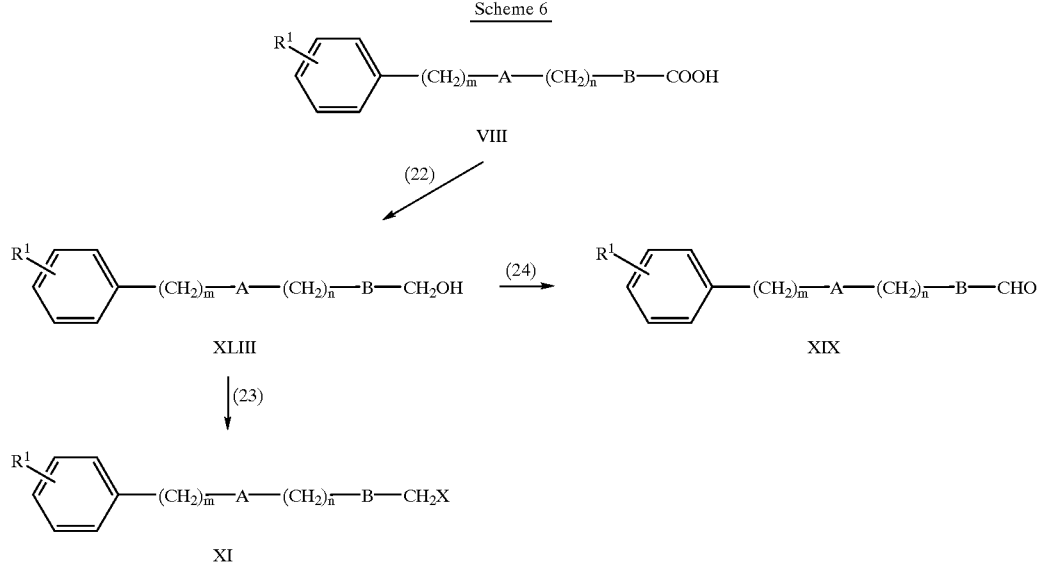

In this sequence, a compound XLIII can be prepared by reduction of a compound VIII, for example, with lithium aluminium hydride or borane in an inert solvent such as ethyl ether or tetrahydrofuran at a temperature ranging from 25° C. to the solvent reflux for a time from 2 to 24 hours (step 22). A compound XI wherein X is alkyl- or aryl-sulfonate group is prepared starting from a compound XLIII by reaction with an alkyl- or aryl-sulfonate chloride, for example mesyl or tosyl chloride, using pyridine as the solvent, or in the presence of triethylamine in a suitable solvent such as chloroform or dichloromethane at a temperature between –20° and 25° C. for a time from 8 to 24 hours (step 23). A compound XIX can be obtained by oxidizing a compound XLIII following chemical processes widely described in literature, for example, by reaction with pyridinium chlorochromate or with manganese dioxide in an inert solvent such as dichloromethane at room temperature for a time from 2 to 24 hours (step 24). Alternatively, a compound XIX wherein A is oxygen can be obtained by reaction of a compound XLII with K=CHO (formyl) with a compound XXIV following one of the processes described for the preparation of VIIIe starting from XLII and XXIV.

A starting compound of formula XLVII, i.e. of general formula XIV wherein E is —COOR$^9$, can be prepared following the synthetic process represented in scheme 7.

Scheme 7

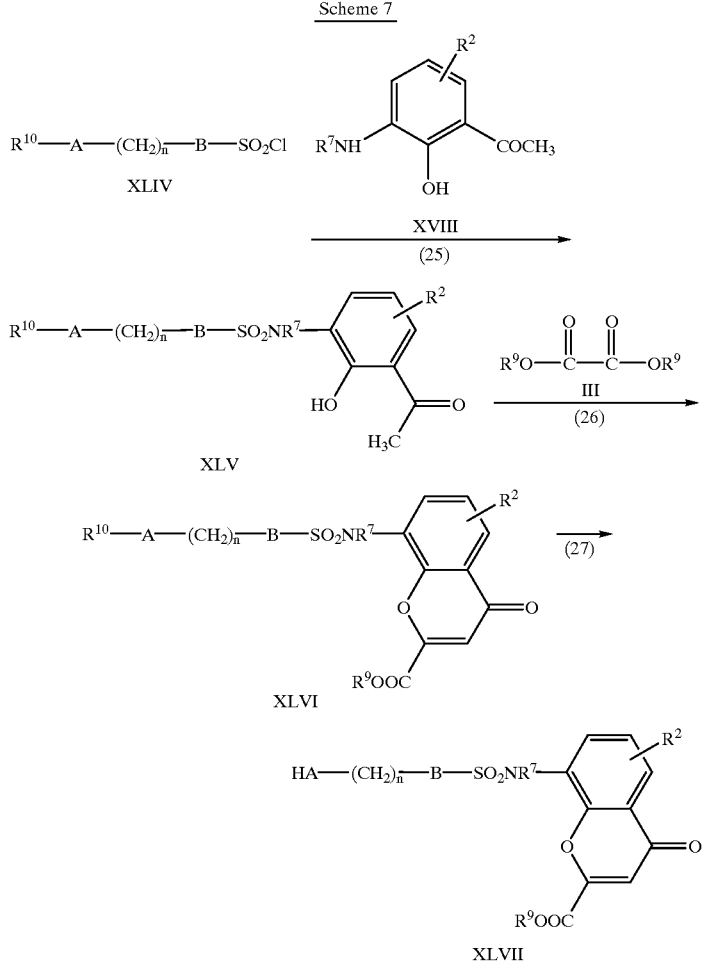

In this sequence, a compound XLIV, wherein B and n have the above mentioned meanings, A is an oxygen or sulfur atom and $R^{10}$ is a suitable hydroxy- or thio-protecting group, for example, when B is a phenyl group and n=0, $R^{10}$ can be a methyl group, is reacted with a compound XVIII (step 25) in the conditions described for the preparation of IIa starting from VIII and XVIII, to obtain a compound XLV. A compound XLVI can be obtained by reaction of a compound XLV with a compound III followed by treatment with hydrochloric acid according to the process described above for the preparation of V starting from II (step 26). The cleavage of the protecting group $R^{10}$ in XLVI (step 27) gives compound XLVII. When B is a phenyl group, n=0 and $R^{10}$ is a methyl group, said transformation is effected by treatment with boron tribromide in a solvent such as dichloromethane or ethyl ether at a temperature ranging from −40° C. to the room temperature and for a time from 4 to 24 hours.

A starting compound XLIV, when no commercially available, can be obtained starting from commercial compounds through similar chemical processes. For example, the chlorosulfonyl group can be obtained by displacing of the corresponding diazonium salt with sulfur dioxide gas according to processes described in literature (Cornish E. J. et al., *J. Pharm. Pharmac.*, 1966, 18, 65). The diazonium salt can be obtained starting from the corresponding aromatic amine prepared, when not commercially available, starting from the corresponding carboxylic acid through the Curtius rearrangement of the acyl azides according to processes described in literature (Campiani G. et al., *J. Org. Chem.*, 1993, 58, 7665).

A starting compound XXIIa,

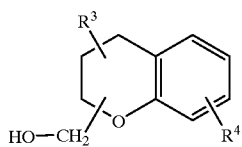

XXIIa

XXIIa
i.e. of general formula XXII with T=$CH_2$, Y—Z=$CH_2CH_2$, U=oxygen, G=hydrogen and n=1, can be obtained starting from a commercial 2-hydroxyacetophenone according to synthetic processes described in literature. Thus, a compound XXIIa with the hydroxymethyl group at the 2-position of the dihydrobenzopyran ring can be prepared according to the processes described, for example, by Augstein J. et al.,*J. Med. Chem.*, 1968, 11, 844 and Urban F. J. et al., *J. Heterocyclic Chem.*, 1991, 29, 431. A compound XXIIa with the hydroxymethyl group at the 3-position of the dihydrobenzopyran ring can be prepared according to the process described, for example, by Okumura K. et al., *Chem. Pharm. Bull.*, 1974, 22, 331. A compound XXIIa with the hydroxymethyl group at the 4-position of the dihydrobenzopyran ring can be prepared according to the process described, for example, by Solladie G. et al., *Synthesis*, 1991, 569.

A starting compound XXIIb,

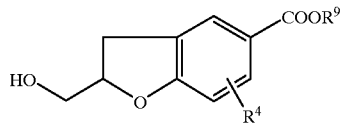

XXIIb i.e. of general formula XXII with T=single bond, Y—Z=CH$_2$CH$_2$, G=COOR$^9$, U=O, n=1 and with the hydroxymethyl group at the 2-position of the dihydrobenzofuran ring, can be obtained starting from a suitable commercial 4-hydroxybenzoic acid ester, following processes described in literature (Eggler J. F. et al., U.S. Pat. No. 4,703,052).

A starting compound XXIIc, i.e. of general formula XXII with T=single bond, Y—Z=CH$_2$CH$_2$, G=Br or Cl, U=O, n=1 and with the hydroxymethyl group at the 3-position of the dihydrobenzofuran ring, can be obtained subjecting a compound XLVIII to the action of a suitable metal hydride, such as sodium borohydride, in a solvent such as methanol, ethanol or tetrahydrofuran, in the presence of a catalytic amount of water, at a temperature between 20° C. and the solvent reflux for a time from 3 to 24 hours (step 28).

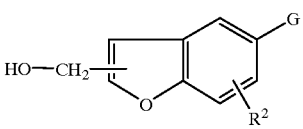

XLVIII

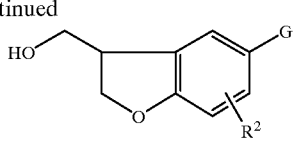

XXIIc

XLVIII XXIIc
A compound XLVIII can be prepared following processes described in literature (Boyle E. A. et al., *J. Med. Chem.*, 1986, 29, 894).

A starting compound XXIId,

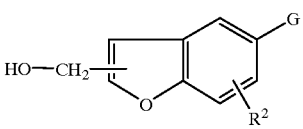

XXIId

XXIId
i.e. of general formula XXII with T=single bond, Y—Z=CH=CH, G=Br or Cl, U=O and n=1, can be obtained according to processes described in literature or through similar transformations of products described in literature. Thereby, a compound XXIId with the hydroxymethyl group at the 2-position of the benzofuran ring can be obtained, for example, according to the process described by Dann O. et al., *Liebigs Ann. Chem.*, 1982, 1836. A compound XXIId with the hydroxymethyl group at the 3-position of the benzofuran ring can be obtained according to the conditions described at step 28, by reduction of a suitable benzofuran-3-carboxylic acid ester, obtainable in its turn according to processes described in literature (Mustafa A., *Chem. Heterocycl. Compd.*, Weissberger-Taylor Eds., John Wiley & Sons, N.Y., 1974, vol. 29, 114–117).

The starting compounds XXIX can be obtained according to one of the processes described above for the preparation of the compounds XXII starting from commercial or easily available compounds through similar synthetic methods.

A starting compound IX wherein R$^7$ is hydrogen can be prepared, for example, according to the synthetic process represented in scheme 8.

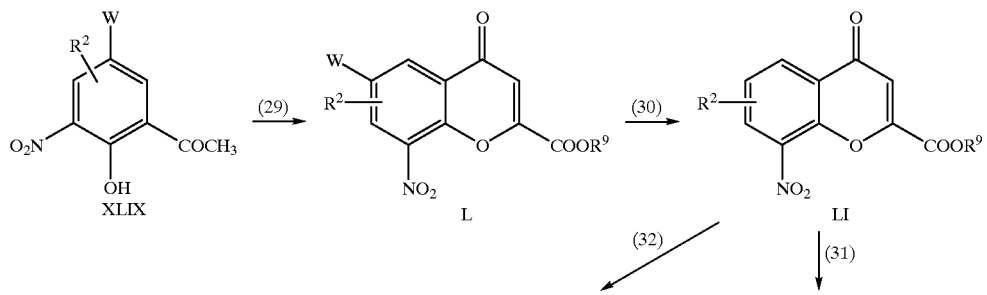

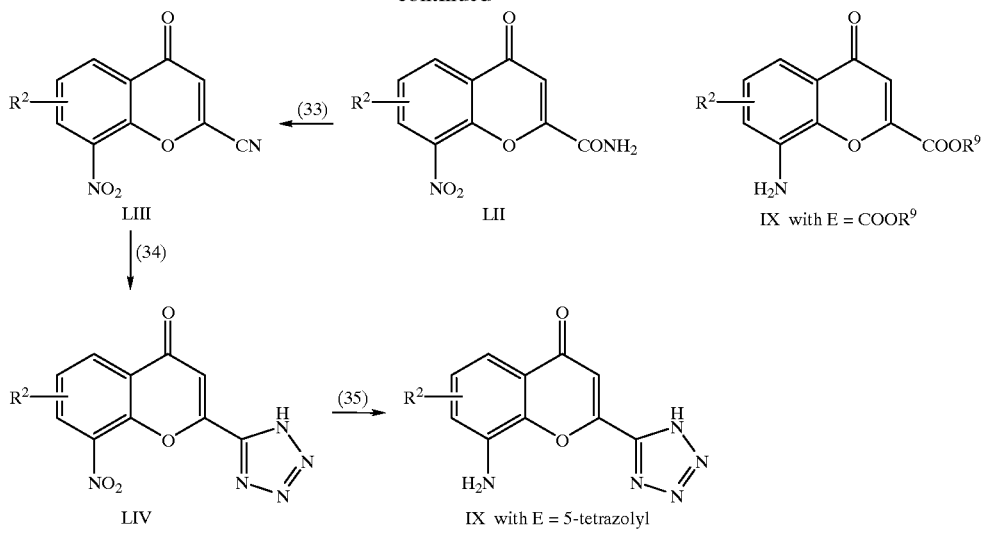

Starting from a compound XLIX, easily available following a synthetic process described in literature (JP 03095144, 1991), wherein $R^2$ represents the groups defined above and W can be a bromine or chlorine atom, a compound L can be prepared by reaction with a compound III (step 29) in the conditions described for the preparation of V starting from II and III. Through dehalogenation of a compound L, for example, with formic acid in the presence of catalytic amounts of 10% palladium-on-charcoal, in a suitable solvent such as N,N-dimethylformamide, at a temperature between 100° C. and the solvent reflux, for a time from 2 to 8 hours, a compound LI can be obtained (step 30). The reduction of the nitro group of a compound LI, for example, by hydrogenation in the presence of catalytic amounts of 5% palladium-on-charcoal, under room pressure and temperature, in a suitable solvent such as methanol, ethanol or methanol and chloroform mixtures, for a time from 1 to 8 hours, leads to a compound IX with $E=COOR^9$ (step 31). The transformation of LI into a tetrazole compound LIV involves a three-step process (32, 33 and 34) identical to the process described above for the preparation VII starting from V. A compound IX wherein E is the 5-tetrazolyl group can be obtained by hydrogenation of a compound LIV in the conditions described above for the preparation of IX with $D=COOR^9$ starting from LI.

A starting compound XVIII, wherein $R^7$ is hydrogen, is obtained according to a process described in literature (JP 03095144, 1991).

A starting compound XXI can be obtained starting from a compound XVIII wherein $R^7$ is hydrogen by reaction first with sodium nitrite in a mixture of concentrated sulfuric acid and water at a temperature between $-10°0$ and 10° C. for a time from 20 minutes to 2 hours, then by treatment of said reaction mixture with potassium iodide in the presence of copper powder at 75° C. for 2 hours.

The compounds IX and XVIII wherein $R^7$ is a methyl group, can be obtained starting from the corresponding compounds wherein $R^7$ is hydrogen according to similar chemical processes for the monoalkylation of primary amines described in literature (Johnstone R. A. W. et al. *J. Chem. Soc. C,* 1969, 2223).

A starting compound XII can be prepared according to processes described in literature (Huan F. C. et al., *J. Med. Chem.,* 1991, 3, 1704).

The compounds of the present invention show a remarkable antagonistic activity of leukotrienes effects and show a good oral bioavailability, and they have therefore anti-inflammatory and anti-allergic properties which make them useful in the treatment of diseases wherein those mediators are involved. Said compounds can be therefore used in human therapy, for the prevention and treatment of allergic rhinitis, bronchial asthma, hypersensitivity reactions such as allergic conjunctivitis, various inflammatory conditions such as rheumatoid arthritis, osteoarthritis, tendinitis, bursitis, psoriasis and related inflammations.

The compound of the present invention may also be used in the treatment of diseases of the cardiovascular system, such as cardiac ischemia, myocardial infarct, coronary spasm, cardiac anaphylaxis, cerebral oedema and endotoxyc schock.

For the intended therapeutic uses, the compounds of the invention are formulated in suitable pharmaceutical compositions, using conventional techniques and methods, as disclosed in Remington's Pharmaceutical Science Handbook, Mack Pub. Co., N.Y. U.S.A. Examples of said formulations include capsules, tablets, syrups and the like, containing from 1 to 1000 mg of active principle per unit dose.

EXAMPLES

The following examples illustrate the preparation of the compounds of the present invention.

Example 1

8-[2-(Benzyloxymethyl)chromane-6-carboxamido]-4-oxo-4H-1-benzopyran-2-carboxylic acid 1A Ethyl 4-oxo-4H-1-benzopyran-2-carboxylate A 2,68 M sodium ethoxide solution in ethanol (21,9 ml) was added slowly to a solution of 2-hydroxyacetophenone (1.76 ml, 14.7 mmol) and diethyl oxalate (3.98 ml, 29.4 mmol) in a mixture of dry ethyl ether (20 ml) and absolute ethanol (20 ml). The mixture was stirred under reflux for 3 h. Afterwards it was diluted with ethyl ether (40 ml), added with 1M HCl (25 ml) and extracted with ethyl ether (3×40 ml). The combined ether phases were dried and the solvents were removed by evaporation under reduced pressure. The obtained residue was dissolved in absolute ethanol (60 ml) and 0.380 ml of concentrated hydrochloric acid were added. The resulting mixture was left under stirring at 75° C. for 1 h. After this time, 50 ml of water were poured on the mixture which was extracted with ethyl acetate (3×50 ml). The organic phase was washed successively with a sodium bicarbonate saturated solution and a NaCl saturated solution, dried and the solvents were evaporated off under reduced pressure, to obtain a crude which was purified by crystallization in ethyl ether, thereby obtaining 2.660 g of the title product (83% yield).

$^1$H N.M.R. (300 MHz, CDCl$_3$) δ ppm: 1.41 (t, 3H); 4.43 (q, 2H); 7.08 (s, 1H); 7.42 (t, 1H); 7.59 (d, 1H); 7.71 (t, 1H); 8.16 (dd, 1H).

1B Ethyl 2-chromanecarboxylate

A solution of ethyl 4-oxo-4H-1-benzopyran-2-carboxylate (2.0 g, 9.17 mmol) in methanol (60 ml), chloroform (25 ml) and glacial acetic acid (20 ml) was added with 10% palladium-on-charcoal and the mixture was left under stirring at room pressure and temperature for 24 h. under hydrogen atmosphere. After that, the catalyst was filtered off and the filtrate was evaporated to dryness. The residue was redissolved in ethyl ether and washed successively with a 5% sodium bicarbonate solution and a sodium chloride saturated solution. The mixture was dried and the solvent was evaporated off under reduced pressure, to obtain 1.575 g of the title product (84% yield).

$^1$H N.M.R. (300 MHz, CDCl$_3$) δ ppm: 1.38 (t, 3H); 2.01–2.29 (sc, 2H); 2.78 (m, 2H); 4.21 (q, 2H); 4.69 (dd, 1H); 6.82 (t, 1H); 6.90 (d, 1H); 7.01 (d, 1H); 7.09 (t, 1H).

1C 2-Chromanemethanol

A solution of ethyl 2-chromanecarboxylate (1.575 g, 7.68 mmol) in a mixture of tetrahydrofuran (75 ml) and water (2 ml) was added with sodium borohydride (0.686 g, 18.2 mmol) in small portions and the mixture was left under stirring at room temperature for 48 h. Afterwards the mixture was cooled at −10° C. and added with acetone (47 ml) stirring at room temperature for 0.5 h. Subsequently water (100 ml) was added and the mixture was extracted with dichloromethane. The combined organic phases were dried and the solvent was removed by evaporation under reduced pressure, thereby obtaining 1.218 g of the title product (97% yield).

$^1$H N.M.R. (300 MHz, CDCl$_3$) δ ppm: 1.87 (m, 1H); 1.94 (m, 1H); 2.18 (broad s, 1H); 2.76 (m, 1H); 2.90 (m, 1H); 3.76 (dd, 1H); 3.85 (dd, 1H); 4.13 (m, 1H); 6.84 (sc, 2H); 7.07 (sc, 2H).

1D 2-(Benzyloxymethyl)chromane

A suspension of 60% sodium hydride dispersion in mineral oil (0.711 g, 17.8 mmol, previously washed with dry petroleum ether) in dry N,N-dimethylformamide (30 ml) was added; under inert atmosphere, with 2-chromanemethanol (1.218 g, 7.43 mmol) dissolved in N,N-dimethylformamide (15 ml) and the mixture was left under stirring at room temperature for 1 h. After that a solution of benzyl hbromide (2.12 ml, 17.8 mmol) in N,N-dimethylformamide (20 ml) and some crystals of tetrabutylammonium iodide were added stirring at room temperature for 18 h. Afterwards, water (10 ml) was added and the solvent was evaporated off under reduced pressure. The obtained residue was partitioned in a mixture of water (70 ml) and ethyl ether (70 ml), the phases were separated and the aqueous one was extracted with ethyl ether (3×70 ml). The combined organic phases were dried and the solvent was evaporated off under reduced pressure, to obtain a crude which was purified by flash chromatography through a silica gel column. Eluting with petroleum ether:ethyl ether, 9:1, 1.569 g of the title product were recovered (83% yield).

$^1$H N.M.R. (300 MHz, CDCl$_3$) δ ppm: 1.85 (m, 1H); 2.04 (m, 1H); 2.74 (m, 1H); 2.87 (m, 1H); 3.61 (dd, 1H); 3.71 (dd, 1H); 4.21 (m, 1H); 4.62 (s, 2H); 6.79–6.85 (sc, 2H); 7.00–7.10 (sc, 2H); 7.25–7.36 (sc, 5H)

1E 2-(Benzyloxymethyl)-6-chromanecarbaldehyde

Phosphorous oxychloride (0.863 ml, 9.26 mmol) was added very slowly and under inert atmosphere on N-methylformanilide (1.14 ml, 9.26 mmol) and the mixture was left under stirring at room temperature for 30 minutes. After that 2-(benzyloxymethyl)chromane (1.569 g, 6.18 mmol) was added stirring at 65° C. for 1.5 h. Subsequently the mixture was diluted with dichloromethane (30 ml), added with a 15% sodium acetate solution (20 ml), the phases were separated and the organic phase was washed successively with a 1M hydrochloric acid solution and a sodium chloride saturated solution. After drying and removing the solvent by evaporation under reduced pressure, a residue was obtained which was purified by flash chromatography through a silica gel column. Eluting with hexane:ethyl acetate, 10:1, 0.921 g of the title product were recovered (53% yield).

$^1$H N.M.R. (300 MHz, CDCl$_3$) δ ppm: 1.92 (m, 1H); 2.04 (m, 1H); 2.89 (m, 2H); 3.70 (dd, 1H); 3.76 (dd, 1H); 4.38 (m, 1H); 4.68 (s, 2H); 6.98 (d, 1H); 7.32–7.41 (sc, 5H); 7.64 (sc, 2H); 9.87 (s, 1H).

1F 2-(Benzyloxymethyl)-6-chromanecarboxylic acid

A solution of 2-(benzyloxymethyl)-6-chromane-carbaldehyde (0.921 g, 3.27 mmol) in acetone (5 ml) was added at 0° C. with Jones reagent, consisting of a mixture of chromium trioxide (0.326 g, 3.27 mmol), water (0.95 ml) and concentrated sulfuric acid (0.27 ml). The mixture was left under stirring at room temperature for 18 h. After that, a mixture of isopropyl alcohol (10 ml) and water (50 ml) was added, extracting with ethyl ether (3×30 ml). The organic phase was dried and the solvents were evaporated off under reduced pressure to obtain a residue which was purified by chromatography through a silica gel column. Eluting with hexane:ethyl acetate, 7:3, 0.580 g of the title compound were obtained (60% yield).

$^1$H N.M.R. (300 MHz, CDCl$_3$) δ ppm: 1.87 (m, 1H); 2.08 (m, 1H); 2.84 (m, 2H); 3.65 (dd, 1H); 3.72 (dd, 1H); 4.29 (m, 1H); 4.62 (s, 2H); 6.88 (d, 1H); 7.32–7.40 (sc, 5H); 7.82 (sc, 2H).

1G 4-Bromophenyl acetate

A solution of 4-bromophenol (25 g, 0.145 mol) in 100 ml of chloroform was added at 0° C. with triethylamine (20.1 ml) and acetic anhydride (16.4 ml) stirring at room temperature for 2 h. After that the mixture was washed with a 0.2M HCl solution, dried and the solvent was evaporated off under reduced pressure, thereby obtaining the title compound as a colourless oil (quantitative yield).

1H 5-Bromo-2-hydroxyacetophenone

A mixture of 4-bromophenyl acetate (31.3 g, 0.145 mol) and AlCl$_3$ (47.3 g) was heated at 120° C. for 2 h. Afterwards the mixture was left to cool at a temperature of about 50° C. and added carefully with a mixture of ice (70 g) and concentrated hydrochloric acid (15 ml). The resulting mixture was heated at 100° C. to prepare a homogeneous solution. After that was cooled at room temperature and extracted with ethyl acetate (4×100 ml). The organic phase was dried and the solvent was evaporated off under reduced pressure, to obtain a crude which was purified by chromatography through a silica gel column, eluting with hexane:chloroform, 9:1, thereby recovering 23.7 g of the title compound (76% yield).

$^1$H N.M.R. (300 MHz, CDCl$_3$) δ ppm: 2.56 (s, 3H); 6.78 (d, 1H); 7.43 (dd, 1H); 7.72 (d, 1H); 12.10 (s, 1H).

1I 5-Bromo-2-hydroxy-3-nitroacetophenone

A solution of 5-bromo-2-hydroxyacetophenone (23.7 g, 0.110 mol) in carbon tetrachloride (90 ml) was added with concentrated nitric acid (17.2 ml). The mixture was left under stirring at 75° C. for 50 minutes, then left to cool at room temperature. The precipitated solid was recovered by filtration washing with cold carbon tetrachloride. After drying under vacuum, 20.9 g of the title product were obtained as a light yellow solid (73% yield).

$^1$H N.M.R. (300 MHz, CDCl$_3$) δ ppm: 2.73 (s, 3H); 8.14 (d, 1H); 8.31 (d, 1H); 12.92 (s, 1H).

1J 3-Amino-2-hydroxyacetophenone

Following the process described at point B, starting from 5-bromo-2-hydroxy-3-nitroacetophenone dissolved in methanol:dichloromethane, 9:1, the title compound was obtained as the hydrobromide (quantitative yield).

$^1$H N.M.R. (300 MHz, CD$_3$OD) δ ppm: 2.72 (s, 3H); 7.13 (t, 1H); 7.69 (dd, 1H); 8.08 (dd, 1H).

1K N-(3-Acetyl-2-hydroxyphenyl)-2-(benzyloxymethyl) chromane-6-carboxamide

A suspension of 2-(benzyloxymethyl)-6-chromanecarboxylic acid (0.700 g, 2.35 mmol) in oxalyl chloride (5.98 ml) was heated at 75° C. for 35 minutes. The oxalyl chloride excess was evaporated off in a nitrogen stream and the resulting residue was dissolved in the minimum amount of dry methylene chloride. This solution was added at 0° C. and under inert atmosphere to a solution of 3-amino-2-hydroxyacetophenone (0.550 g, 2.37 mmol), pyridine (7 ml) and dry methylene chloride (40 ml). The resulting mixture was left under stirring at room temperature for 18 h, then diluted with methylene chloride (40 ml), washed successively with 1M HCl and a sodium chloride saturated solution, dried and the solvent was evaporated off under reduced pressure. A crude was obtained which was purified by chromatography through a silica gel column, eluting with petroleum ether:chloroform mixtures of increasing polarity. At a 40% chloroform proportion, 0.732 g of the title compound were eluted (72% yield).

$^1$H N.M.R. (300 MHz, CDCl$_3$) δ ppm: 1.92 (m, 1H); 2.14 (m, 1H); 2.70 (s, 3H); 2.93 (m, 2H); 3.70 (dd, 1H); 3.78 (dd, 1H); 4.33 (m, 1H); 4.62 (s, 2H); 7.00 (m, 2H); 7.30–7.42 (sc, 5H); 7.51 (d, 1H); 7.70 (sc, 2H); 8.09 (s, 1H); 8.80 (d, 1H); 13.01 (s, 1H).

1L Ethyl 8-[2-(benzyloxymethyl)chromane-6-carboxamido]-4-oxo-4H-1-benzopyran-2-carboxylate Following the process described at point A, starting from N-(3-acetyl-2-hydroxyphenyl)-2-(benzyloxymethyl) chromane-6-carboxamide and diethyl oxalate, the title compound was prepared, which was purified by warm crystallization in ethyl acetate (66% yield).

$^1$H N.M.R. (300 MHz, CDCl$_3$) δ ppm: 1.47 (t, 3H); 1.90 (m, 1H); 2.11 (m, 1H); 2.89 (m, 2H); 3.67 (dd, 1H); 3.75 (dd, 1H); 4.32 (m, 1H); 4.49 (q, 2H); 4.65 (s, 2H); 6.95 (d, 1H); 7.15 (s, 1H); 7.30–7.40 (sc, 5H); 7.47 (t, 1H); 7.70 (dd, 1H); 7.78 (d, 1H); 7.88 (dd, 1H); 8.74 (s, 1H); 8.93 (dd, 1H).

1M 8-[2-(Benzyloxymethyl)chromane-6-carboxamido]-4-oxo-4H-1-benzopyran-2-carboxylic acid A suspension of ethyl 8-[2-(benzyloxymethyl)chromane-6-carboxamido]-4-oxo-4H-1-benzopyran-2-carboxylate (0.240 g, 0.47 mmol) in a mixture of methanol (15 ml) and tetrahydrofuran (15 ml) was added with 0.510 ml of a 1M NaOH solution, stirring at room temperature for 1.30 h. After that the mixture was evaporated to dryness and the resulting residue was suspended in water adding 0.2M hydrochloric acid to slightly acid pH (pH=4–5). The solid was recovered by filtration, washed with methanol and dried on phosphorous pentoxyde under vacuum, thereby obtaining 0.221 g of the title compound as a white solid which decomposes above 283° C. (97% yield).

$^1$H N.M.R. (300 MHz, CD$_3$OD/CDCl$_3$ mixtures) δ ppm: 1.82 (m, 1H); 2.12 (m, 1H); 2.85 (m, 2H); 3.62 (dd, 1H); 3.67 (dd, 1H); 4.23 (m, 1H); 4.57 (s, 2H); 6.85 (d, 1H); 7.01 (s, 1H); 7.20–7.30 (sc, 5H); 7.38 (t, 1H); 7.69 (m, 2H); 7.83 (dd, 1H); 8.48 (dd, 1H).

Example 2

N-[4-Oxo-2-(1H-5-tetrazolyl)-4H-1-benzopyran-8-yl]-2-(benzyloxymethyl)chromane-6-carboxamide

2A Ethyl 6-bromo-8-nitro-4-oxo-4H-1-benzopyran-2-carboxylate

Following the process described in example 1 (point A), starting from 5-bromo-2-hydroxy-3-nitroacetophenone and diethyl oxalate, the title compound was prepared, which was purified by crystallization in tetrahydrofuran:ethanol mixtures (77% yield).

$^1$H N.M.R. (300 MHz, CDCl$_3$) δ ppm: 1.45 (t, 3H); 4.49 (q, 2H); 7.21 (s, 1H); 8.48 (d, 1H); 8.58 (d, 1H).

2B Ethyl 8-nitro-4-oxo-4H-benzopyran-2-carboxylate

A mixture of ethyl 6-bromo-8-nitro-4-oxo-4H-1-benzopyran-2-carboxylate (5.0 g, 14.6 mmol), 10% palladium-on-charcoal (0.541 g), formic acid (7.90 ml) and N,N-dimethylformamide (42 ml) was stirred at 145° C. for 5.75 h under inert atmosphere. After this time the mixture was left to cool and the catalyst was removed by filtration, washing it with N,N-dimethylformamide. The resulting filtrate was evaporated to dryness and the obtained residue was purified by chromatography through a silica gel column. Eluting with hexane:chloroform, 85:15, 2.109 g of the title product were recovered (55% yield).

$^1$H N.M.R. (300 MHz, CDCl$_3$) δ ppm: 1.46 (t, 3H); 4.50 (q, 2H); 7.21 (s, 1H); 7.61 (t, 1H); 8.41 (dd, 1H); 8.49 (dd, 1H).

2C 8-Nitro-4-oxo-4H-1-benzopyran-2-carboxamide

Gas ammonia was bubbled for 30 minutes in a solution of ethyl 8-nitro-4-oxo-4H-1-benzopyran-2-carboxylate (2.109 g, 8.02 mmol) in anhydrous ethanol (50 ml) and anhydrous tetrahydrofuran (50 ml). After that the mixture was evaporated to dryness and the resulting solid residue was suspended in concentrated hydrochloric acid (20 ml) stirring at room temperature for 4 h. Then the mixture was diluted with water, the solid was recovered by filtration, washed repeatedly with water and dried under vacuum on phosphorous pentoxyde, to obtain 1.515 g of the title product (81% yield).

$^1$H N.M.R. (300 MHz, DMSO) δ ppm: 7.01 (s, 1H); 7.75 (t, 1H); 8.01 (broad s, 1H); 8.37 (broad s, 1H); 8.43 (dd, 1H); 8.61 (dd, 1H).

2D 8-Nitro-4-oxo-4H-1-benzopyran-2-carbonitrile

Phosphorous oxychloride (2.86 ml) was added very slowly at 0° C. to dry N,N-dimethylformamide (40 ml) and the mixture was left under stirring at room temperature for 35 minutes. After that a solution of 8-nitro-4-oxo-4H-1-benzopyran-2-carboxamide (1.515 g, 6.47 mmol) in N,N-dimethylformamide (10 ml) was added and the mixture was left under stirring at room temperature for 18 h. After this time, the reaction mixture was poured onto an ice-water mixture (100 ml) and extracted with ethyl acetate (4×40 ml). After drying and removing the solvents under reduced pressure, a residue was obtained which was purified by chromatography through a silica gel column. Eluting with hexane:chloroform, 7:3, 1.094 g of the title product were recovered (78% yield).

$^1$H N.M.R. (300 MHz, DMSO) δ ppm: 7.01 (s, 1H); 7.70 (t, 1H); 8.38 (dd, 1H); 8.56 (dd, 1H).

2E 8-Nitro-4-oxo-2-(5-1H-tetrazolyl)-4H-1-benzopyran

A mixture of 8-nitro-4-oxo-4H-1-benzopyran-2-carbonitrile (1.094 g, 5.06 mmol), sodium azide (1.638 g, 25.3 mmol), ammonium chloride (1.349 g, 25.3 mmol) and dry N,N-dimethylformamide (50 ml) was left under stirring at 100° C. for 1.25 h. After that the mixture was cooled at room temperature and poured onto a 1M hydrochloric acid solution (50 ml) recovering the formed precipitate by filtration. The resulting solid was suspended in concentrated hydrochloric acid (12 ml) stirring at room temperature for 2.5 h. After this time the acid mixture was diluted with water (50 ml) and extracted with ethyl acetate (4×30 ml). The organic phase was dried and the solvent was evaporated off under reduced pressure, thereby obtaining 0.896 g of the title product (69% yield).

$^1$H N.M.R. (300 MHz, DMSO) δ ppm: 7.21 (s, 1H); 7.73 (t, 1H); 8.41 (dd, 1H); 8.55 (dd, 1H).

2F 8-Amino-4-oxo-2-(5-1H-tetrazolyl)-4H-1-benzopyran

Following the process described in example 1 (point B), by hydrogenating for 4 h 8-nitro-4-oxo-2-(5-1H-tetrazolyl)-4H-1-benzopyran (0.896 g, 3.46 mmol) with 5% palladium-on-charcoal (91 mg) in a mixture of methanol (65 ml), chloroform (20 ml) and concentrated hydrochloric acid (2 ml), the title compound was prepared as its corresponding hydrochloride (quantitative yield).

$^1$H N.M.R. (300 MHz, CD$_3$OD) δ ppm: 7.25 (s, 1H); 7.62 (t, 1H); 7.94 (d, 1H); 8.14 (d, 1H).

2G N-[4-Oxo-2-(1H-5-tetrazolyl)-4H-1-benzopyran-8-yl]-2-(benzyloxymethyl)chromane-6-carboxamide Following the process described in example 1 (point K), starting from 2-(benzyloxymethyl)-6-chromanecarboxylic acid and 8-amino-4-oxo-2-(5-1H-tetrazolyl)-4H-1-benzopyran, the title compound was prepared as a white solid with melting point 214–216° C., which was purified by crystallization in methanol (57% yield).

$^1$H N.M.R. (300 MHz, CD$_3$OD/CDCl$_3$ mixtures) δ ppm: 1.82 (m, 1H); 2.12 (m, 1H); 2.85 (m, 2H); 3.62 (dd, 1H); 3.67 (dd, 1H); 4.23 (m, 1H); 4.58 (s, 2H); 6.89 (d, 1H); 7.18 (s, 1H); 7.20–7.34 (sc, 5H); 7.44 (t, 1H); 7.72 (dd, 2H); 7.87 (dd, 1H); 8.59 (dd, 1H); 8.80 (broad s, 1H).

Example 3

8-[2-(3-Phenylpropyl)chromane-6-carboxamido]-4-oxo-4H-1-benzopyran-2-carboxylic acid 3A 2-Chromanemethyl trifluoromethanesulfonate A mixture of 2-chromanemethanol (0.765 g, 4.67 mmol) and pyridine (1.05 ml) in dry dichloromethane (25 ml) at 0° C. and under inert atmosphere was added with trifluoromethanesulfonic anhydride (1.10 ml, 6.53 mmol) and the mixture was left under stirring for 18 h at 0° C., then it was diluted with dichloromethane (20 ml), added with water (25 ml) and the aqueous phase was extracted with dichloromethane (3×20 ml). The combined organic phases were washed successively with 1N HCl, 5% NaHCO$_3$ and a NaCl saturated solution. After drying and removing the solvents, a residue was obtained which was purified by chromatography through a silica gel column, eluting with a hexane:ethyl acetate 9:1 mixture, thereby obtaining 1.381 g of the title compound (82% yield).

$^1$H N.M.R. (300 MHz, CDCl$_3$) δ ppm: 1.90 (m, 1H); 2.05 (m, 1H); 2.82 (m, 1H); 2.93 (m, 1H); 4.33 (m, 1H); 4.64 (d, 2H); 6.86 (m, 2H); 7.07 (m, 2H).

3B 2-(3-Phenylpropyl)chromane

A suspension of magnesium (0.304 g, 12.6 mmol) in dry tetrahydrofuran (5 ml) with a iodine crystal was added drop by drop and under inert atmosphere with a solution of 2-bromoethylbenzene (1.72 ml, 12.6 mmol) in dry tetrahydrofuran (12 ml). The reaction, started during the bromide addition, was left at room temperature for 2.5 h. After that a solution of CuBr.(CH$_3$)$_2$S (163 mg, 0.79 mmol) in tetrahydrofuran (2 ml) and a solution of 2-chromanemethyl trifluoromethanesulfonate (1.381 g, 4.67 mmol) in tetrahydrofuran (5 ml) were added successively at 0° C. and the mixture was left under stirring at 0° C. for 2.5 h. After this time, the mixture was poured slowly onto a mixture of dichloromethane (25 ml) and an ammonium chloride saturated aqueous solution (20 ml). The phases were separated and the aqueous phase was extracted with dichloromethane (4×25 ml). The combined organic extracts were dried and the solvent was evaporated off under reduced pressure, to obtain a crude which was purified by chromatography through a silica gel column, eluting with hexane:dichloromethane, 9:1, to recover 0.990 g of the title product (85% yield).

$^1$H N.M.R. (300 MHz, CDCl$_3$) δ ppm: 1.60–2.00 (sc, 6H); 2.67 (t, 2H); 2.70–2.88 (sc, 2H); 3.98 (m, 1H); 6.80 (m, 2H); 7.03 (m, 2H); 7.17–7.28 (sc, 5H).

3C 2-(3-Phenylpropyl)-6-chromanecarbaldehyde

Following the process described in example 1 (point E), starting from 2-(3-phenylpropyl)chromane, the title compound was prepared (66% yield).

$^1$H N.M.R. (300 MHz, CDCl$_3$) δ ppm: 1.60–2.00 (sc, 6H); 2.68 (t, 2H); 2.82 (m, 2H); 4.08 (m, 1H); 6.88 (d, 1H); 7.18 (m, 3H); 7.26 (m, 2H); 7.60 (m, 2H); 9.81 (s, 1H).

3D 2-(3-Phenylpropyl)-6-chromanecarboxylic acid

Following the process described in example 1 (point F), starting from 2-(3-phenylpropyl)-6-chromanecarbaldehyde, the title compound was prepared (66% yield).

$^1$H N.M.R. (300 MHz, CDCl$_3$) δ ppm: 1.70–2.10 (sc, 6H); 2.73 (t, 2H); 2.88 (m, 2H); 4.12 (m, 1H); 6.87 (d, 1H); 7.20 (m, 3H); 7.31 (m, 2H); 7.88 (m, 2H).

3E N-(3-Acetyl-2-hydroxyphenyl)-2-(3-phenylpropyl) chromane-6-carboxamide

Following the process described in example 1 (point K), starting from 2-(3-phenylpropyl)-6-chromanecarboxylic acid and 3-amino-2-hydroxyacetophenone, the title compound was prepared (45% yield).

$^1$H N.M.R. (300 MHz, CDCl$_3$) δ ppm: 1.65–2.10 (sc, 6H); 2.70 (s, 3H); 2.73 (m, 2H); 2.88 (m, 2H); 4.10 (m, 1H); 6.89 (d, 1H); 6.99 (t, 1H); 7.20–7.35 (sc, 5H); 7.51 (d, 1H); 7.68 (m, 2H); 8.58 (broad s, 1H); 8.79 (d, 1H); 13.01 (s, 1H).

3F Ethyl 8-[2-(3-phenylpropyl)chromane-6-carboxamido]-4-oxo-4H-1-benzopyran-2-carboxylate Following the process described in example 1 (point A), starting from N-(3-acetyl-2-hydroxyphenyl)-2-(3-phenylpropyl)chromane-6-carboxamide and diethyl oxalate, the title compound was prepared, which was purified by chromatography through a silica gel column, eluting with chloroform (47% yield).

$^1$H N.M.R. (300 MHz, CDCl$_3$) δ ppm: 1.48 (t, 3H); 1.65–2.10 (sc, 6H); 2.71 (t, 2H); 2.89 (m, 2H); 4.10 (m, 1H); 4.50 (q, 2H); 6.90 (d, 1H); 7.17 (s, 1H); 7.20–7.35 (sc, 5H); 7.48 (t, 1H); 7.70 (dd, 1H); 7.79 (d, 1H); 7.88 (dd, 1H); 8.74 (s, 1H); 8.93 (dd, 1H).

3H 8-[2-(3-Phenylpropyl)chromane-6-carboxamido]-4-oxo-4H-1-benzopyran-2-carboxylic acid Following the process described in example 1 (point M), starting from ethyl 8-[2-(3-phenylpropyl)chromane-6-carboxamido]-4-oxo-4H-1-benzopyran-2-carboxylate, the title compound was prepared as a white solid with melting point 325–326° C. (80% yield).

$^1$H N.M.R. (300 MHz, CD$_3$OD/CDCl$_3$ mixtures) δ ppm: 1.65–2.10 (sc, 6H); 2.73 (t, 2H); 2.90 (m, 2H); 4.10 (m, 1H); 6.89 (d, 1H); 7.09 (s, 1H); 7.20–7.35 (sc, 5H); 7.47 (t, 1H); 7.77 (m, 2H); 7.92 (dd, 1H); 8.56 (dd, 1H).

Example 4

N-[4-Oxo-2-(1H-5-tetrazolyl)-4H-1-benzopyran-8-yl]-2-(3-phenylpropyl)chromane-6-carboxamide Following the process described in example 2 (point K), starting from 2-(3-phenylpropyl)-6-chromanecarboxylic acid and 8-amino-4-oxo-2-(5-1H-tetrazolyl)-4H-1-benzopyran, the title compound was prepared as a white solid which decomposes at temperatures higher than 370° C. and which was purified by crystallization in methanol (65% yield).

$^1$H N.M.R. (300 MHz, CD$_3$OD/CDCl$_3$ mixtures) δ ppm: 1.65–2.10 (sc, 6H); 2.71 (t, 2H); 2.90 (m, 2H); 4.11 (m, 1H); 6.89 (d, 1H); 7.15–7.35 (sc, 6H); 7.49 (t, 1H); 7.79 (m, 2H); 7.95 (d, 1H); 8.60 (d, 1H).

Example 5

8-[2-(Benzyloxymethyl)benzofuran-5-carboxamido[-4-oxo-4H-1-benzopyran-2-carboxylic acid

5A (4-Bromo-2-formyl)phenyloxyacetonitrile

A mixture of 5-bromosalicylaldehyde (5 g, 24.8 mmol), potassium carbonate (3.78 g, 26.8 mmol) and N,N-dimethylformamide (70 ml) was added with a solution of chloroacetonitrile (1.87 g, 24.8 mmol) in N,N-dimethylformamide (10 ml), then with a catalytic amount of potassium iodide. The resulting mixture was left under stirring at 80° C. for 1.5 h, then was added with water (50 ml) and extracted with ethyl acetate (4×75 ml). The combined organic phases were dried and the solvents were removed under reduced pressure, to obtain 5.126 g of the title compound (98% yield).

$^1$H N.M.R. (300 MHz, CDCl$_3$) δ ppm: 4.93 (s, 2H); 7.01 (d, 1H); 7.73 (dd, 1H); 8.00 (d, 1H).

5B 5-Bromo-2-benzofurancarboxylic acid

A mixture of (4-bromo-2-formyl)phenyloxy-acetonitrile (5.11 g, 21.1 mmol), potassium hydroxide (6.0 g) and absolute ethanol (250 ml) was refluxed for 24 h, after that was diluted with water (75 ml) and acidified with 1M hydrochloric acid. The volatiles were evaporated off under reduced pressure and the resulting aqueous residue was extracted with ethyl acetate (4×100 ml). The combined organic phases were dried and the solvent was evaporated off under reduced pressure, to obtain the title compound as a yellow solid with melting point 249–252° C. (98% yield).

$^1$H N.M.R. (300 MHz, CD$_3$OD/CDCl$_3$ mixtures) δ ppm: 7.50 (m, 3H); 7.80 (s, 1H).

5C Ethyl 5-bromo-2-benzofurancarboxylate

A solution of 5-bromo-2-benzofurancarboxylic acid (5.01 g, 20.8 mmol) in absolute ethanol (150 ml) was added with concentrated sulfuric acid (15 ml) and the mixture was refluxed under stirring for 2 h. After this time, the volatiles were evaporated off under reduced pressure and the resulting residue was neutralized with a sodium bicarbonate saturated solution and extracted with ethyl ether (4×100 ml). The mixture was dried and the solvent was evaporated off under reduced pressure, to obtain 5.19 g of the title compound as a white solid with melting point 58–60° C. (93% yield).

$^1$H N.M.R. (300 MHz, CDCl$_3$) δ ppm: 1.34 (t, 3H); 4.35 (q, 2H); 7.39 (m, 3H); 7.71 (d, 1H).

5D (5-Bromo-2-benzofuranyl)methanol

A solution of ethyl 5-bromo-2-benzofurancarboxylate (2.20 g, 8.19 mmol) in tetrahydrofuran (75 ml) was added with sodium borohydride (1.24 g) and some drops of water. The mixture was refluxed under stirring for 18 h and, after that, was added with some drops of concentrated HCl. The volatiles were evaporated off and the resulting residue was diluted with water and extracted with ethyl ether (3×75 ml). After drying and evaporating off the solvent under reduced pressure, a crude was obtained which was purified by chromatography through a silica gel column, eluting with petroleum ether:chloroform, 60:40. 1.19 g of the title product were recovered as a white solid with melting point 101–103° C. (64% yield).

$^1$H N.M.R. (300 MHz, CDCl$_3$) δ ppm: 2.10 (broad s, 1H); 4.76 (s, 2H); 6.60 (s, 1H); 7.33 (m, 2H); 7.66 (s, 1H).

5E 2-(Hydroxymethyl)benzofuran-5-carbonitrile

A solution of 5-bromo-2-benzofuranylmethanol (1.19 g, 5.24 mmol), copper (I) cyanide (0.470 g, 5.25 mmol) and N-methylpyrrolidinone (15 ml) was left under stirring at 200° C. for 3.5 h, then was poured onto a solution of ethylenediamine (6 g) in water (80 ml) and extracted with ethyl acetate (3×75 ml). The organic phase was dried and the solvents were evaporated off under reduced pressure. The resulting crude was purified by chromatography through a silica gel column, eluting with n-hexane:ethyl acetate mixtures of increasing polarity, thereby obtaining 0.671 g of title product as a yellow solid with melting point 113–114° C. (74% yield).

$^1$H N.M.R. (300 MHz, CDCl$_3$) δ ppm: 4.82 (s, 2H); 6.74 (s, 1H); 7.54 (m, 2H); 7.87 (s, 1H).

5F 2-(Benzyloxymethyl)benzofuran-5-carbonitrile

A dispersion of potassium hydride (0.990 g, 5.04 mmol) in 20% mineral oil was washed by decantation with anhydrous hexane, then was resuspended in anhydrous benzene (25 ml). This suspension was added at 0° C. and under inert atmosphere with a solution of 2-(hydroxymethyl) benzofuran-5-carbonitrile (0.671 mg, 3.89 mmol) in benzene (10 ml) stirring at room temperature for 15 min, then with benzyl bromide (0.825 ml) and a catalytic amount of tetrabutylammonium iodide. The mixture was left under stirring at room temperature for 4 h, then added with water (50 ml) and extracted with ethyl acetate (4×50 ml). The organic phase was dried and the solvent removed, to obtain a crude which was purified by chromatography through a silica gel column, eluting with n-hexane:ethyl acetate mixtures of increasing polarity, thereby recovering 1.087 g of the title compound as a yellowish oil (82% yield).

$^1$H N.M.R. (300 MHz, CDCl$_3$) δ ppm: 4.54 (s, 2H); 4.55 (s, 2H); 6.66 (s, 1H); 7.28 (m, 5H); 7.45 (s, 2H); 7.79 (s, 1H).

5G 2-(Benzyloxymethyl)benzofuran-5-carboxylic acid

A solution of 2-(benzyloxymethyl)benzofuran-5-carbonitrile (1.087 g, 4.13 mmol) in ethanol (150 ml) was added with 35% NaOH (55 ml) and refluxed under stirring for 3 h. After that the mixture was acidified with 1M HCl, the volatiles were evaporated off and the residue was extracted with ethyl acetate (4×100 ml). The organic phase was dried and the solvent was evaporated off under reduced pressure, to obtain 1.165 g of the title compound as a white solid with melting point 129–132° C. (quantitative yield).

$^1$H N.M.R. (300 MHz, CDCl$_3$) δ ppm: 4.67 (s, 4H); 6.81 (s, 1H); 7.40 (m, 5H); 7.56 (d, 1H); 8.12 (d, 1H); 8.41 (s, 1H).

5H N-(3-Acetyl-2-hydroxyphenyl)-2-(benzyloxymethyl)benzofuran-5-carboxamide

Following the process described in example 1 (point K), starting from 2-(benzyloxymethyl)benzofuran-5-carboxylic acid and 3-amino-2-hydroxyacetophenone, the title compound was prepared as a yellowish solid with melting point 92–94° C., which was purified by chromatography through a silica gel column (98% yield).

$^1$H N.M.R. (300 MHz, CDCl$_3$) δ ppm: 2.58 (s, 3H); 4.60 (s, 4H); 6.74 (d, 1H); 6.91 (t, 1H); 7.34 (m, 5H); 7.41 (d, 1H); 7.51 (d, 1H); 7.82 (d, 1H); 8.10 (d, 1H); 8.63 (s, 1H); 8.73 (d, 1H).

5I 8-[2-(Benzyloxymethyl)benzofuran-5-carboxamido]-4-oxo-4H-1-benzopyran-2-carboxylic acid Following the process described in example 1 (point A), starting from N-(3-acetyl-2-hydroxyphenyl)-2-(benzyloxymethyl)benzofuran-5-carboxamide and diethyl oxalate, ethyl 8-[2-(benzyloxymethyl)benzofuran-5-carboxamido]-4-oxo-4H-1-benzopyran-2-carboxylate was prepared which was subsequently hydrolysed according to the process described in example 1 (point M) to yield the title compound as a white solid with melting point 215–218° C. (65% global yield).

$^1$H N.M.R. (300 MHz, DMSO) δ ppm: 4.61 (s, 2H); 4.72 (s, 2H); 6.97 (s, 1H); 7.11 (s, 1H); 7.38 (m, 5H); 7.57 (t, 1H); 7.76 (d, 1H); 7.93 (d, 1H); 8.02 (d, 1H); 8.09 (d, 1H); 8.38 (s, 1H).

Example 6

8-(2-Benzyloxymethyl-2,3-dihydrobenzofuran-5-carboxamido)-4-oxo-4H-1-benzopyran-2-carboxylic acid

6A Ethyl 4-allyloxybenzoate

A mixture of ethyl 4-hydroxybenzoate (10.0 g, 60.2 mmol) and potassium carbonate (8.32 g, 60.2 mmol) in acetone (50 ml) was added with allyl bromide (7.22 ml, 66.2 mmol) and the mixture was refluxed for 18 h. After that potassium carbonate was filtered off and the solvent was evaporated under reduced pressure, thereby obtaining 12.3 g of a crude containing only the title compound (99% yield).

$^1$H N.M.R. (300 MHz, CDCl$_3$) δ ppm: 1.36 (t, 3H); 4.32 (q, 2H); 4.54 (d, 2H); 5.28 (dd, 1H); 5.40 (dd, 1H); 6.03 (m, 1H); 6.90 (d, 2H); 7.98 (d, 2H).

6B Ethyl 3-allyl-4-hydroxybenzoate

A mixture of ethyl 4-allyloxybenzoate (10.0 g, 48.5 mmol) and N,N-dimethylaniline (20 ml) was left under stirring at 200° C. for 48 h, then diluted with ethyl acetate (150 ml) and washed with 1M HCl. After drying and evaporating off the solvent, a crude was obtained which was purified by chromatography through a silica gel column, eluting with n-hexane:ethyl acetate, 95:5, thereby recovering 6.85 g of the title compound (69% yield).

$^1$H N.M.R. (300 MHz, CDCl$_3$) δ ppm: 1.37 (t, 3H); 3.45 (d, 2H); 4.35 (q, 2H); 5.14 (d, 2H); 6.02 (m, 1H); 6.89 (d, 1H); 7.81 (dd, 1H); 7.83 (s, 1H).

6C Ethyl 2-hydroxymethyl-2,3-dihydrobenzofuran-5-carboxylate

A solution of ethyl 3-allyl-4-hydroxybenzoate (6.74 g, 32.7 mmol) in chloroform (105 ml) was added with meta-chloroperbenzoic acid (11.40 g, 66.1 mmol) and the mixture was refluxed under stirring for 4 h. Afterwards, the solvent was evaporated, the crude was redissolved in ethyl acetate and washed with a 1M NaOH solution. After drying and removing the solvent, a crude was obtained which was purified by chromatography through a silica gel column, eluting with n-hexane:ethyl acetate, 90:10, to recover 5.95 g of the title compound (82% yield).

$^1$H N.M.R. (300 MHz, CDCl$_3$) δ ppm: 1.35 (t, 3H); 3.02 (dd, 1H); 3.20 (dd, 1H); 3.74 (dd, 1H); 3.84 (dd, 1H); 4.29 (q, 2H); 4.95 (m, 1H); 6.69 (d, 1H); 7.78 (s, 1H); 7.79 (d, 1H).

6D Ethyl 2-benzyloxymethyl-2,3-dihydrobenzofuran-2-carboxylate

Following the process described in example 1 (point D), starting from ethyl 2-hydroxymethyl-2,3-dihydrobenzofuran-5-carboxylate and benzyl bromide, the title compound was prepared, which was purified by chromatography through a silica gel column, eluting with n-hexane:ethyl acetate, 95:5 (65% yield).

$^1$H N.M.R. (300 MHz, CDCl$_3$) δ ppm: 1.32 (t, 3H); 2.93 (dd, 1H); 3.13 (dd, 1H); 3.55 (dd, 1H); 3.59 (dd, 1H); 4.27

(q, 2H); 4.51 (dd, 2H); 4.94 (m, 1H); 6.75 (d, 1H); 7.19–7.27 (sc, 5H), 7.78 (s, 1H); 7.85 (dd, 1H).

6E 2-Benzyloxymethyl-2,3-dihydrobenzofuran-2-carboxylic acid

A solution of ethyl 2-benzyloxymethyl-2,3-dihydrobenzofuran-2-carboxylate (1.62 g, 5.47 mmol) in methanol (70 ml) was added with a solution of 1M lithium hydroxide (54.7 ml). The mixture was refluxed under stirring for 3 h, after that was neutralized with 1M HCl and methanol was evaporated off under reduced pressure. The resulting crude was suspended in water (20 ml) and extracted with ethyl acetate (4×25 ml). The organic phase was dried and the solvent was evaporated off under reduced pressure, to obtain 1.436 g of the title compound, which was purified by crystallization in methanol (97% yield).

$^1$H N.M.R. (300 MHz, CDCl$_3$) δ ppm: 3.02 (dd, 1H); 3.26 (dd, 1H); 3.65 (dd, 1H); 3.68 (dd, 1H); 4.60 (dd, 2H); 5.05 (m, 1H); 6.82 (d, 1H); 7.22–7.33 (sc, 5H); 7.90 (s, 1H); 7.94 (d, 1H).

6F N-(3-Acetyl-2-hydroxyphenyl)-2-benzyloxymethyl-2,3-dihydrobenzofuran-5-carboxamide Following the process described in example 1 (point K), starting from 2-benzyloxymethyl-2,3-dihydrobenzofuran-2-carboxylic acid and 3-amino-2-hydroxyacetophenone, the title compound was prepared as a yellowish solid with melting point 103–105° C. and purified by chromatography through a silica gel column (74% yield).

$^1$H N.M.R. (300 MHz, CDCl$_3$) δ ppm: 2.64 (s, 3H); 3.06 (dd, 1H); 3.31 (dd, 1H); 3.66 (dd, 1H); 3.70 (dd, 1H); 4.61 (dd, 2H); 5.06 (m, 1H); 6.86 (d, 1H); 6.85 (t, 1H); 7.26–7.34 (sc, 5H); 7.46 (d, 1H); 7.72 (d, 1H); 7.74 (s, 1H); 8.53 (s, 1H); 8.74 (d, 1H), 12.96 (s, 1H).

6G Ethyl 8-(2-benzyloxymethyl-2,3-dihydrobenzofuran-5-carboxamido)-4-oxo-4H-1-benzopyran-2-carboxylate Following the process described in example 1 (point A), starting from N-(3-acetyl-2-hydroxyphenyl)-2-benzyloxymethyl- 2,3-dihydrobenzofuran-5-carboxamide and diethyl oxalate, the title compound was prepared as a yellow solid with melting point 166–168° C. and purified by crystallization in ethanol (73% yield).

$^1$H N.M.R. (300 MHz, CDCl$_3$) δ ppm: 1.47 (t, 3H); 3.12 (dd, 1H); 3.36 (dd, 1H); 3.70 (dd, 1H); 3.73 (dd, 1H); 4.50 (q, 2H); 4.63 (dd, 2H); 5.11 (m, 1H); 6.91 (d, 1H); 7.15 (s, 1H); 7.30–7.38 (sc, 5H); 7.47 (t, 1H); 7.79 (d, 1H); 7.87 (s, 1H); 7.88 (d, 1H); 8.73 (s, 1H); 8.92 (d, 1H).

6H 8-(2-Benzyloxymethyl-2,3-dihydrobenzofuran-5-carboxamido)-4-oxo-4H-1-benzopyran-2-carboxylic acid Following the process described in example 1 (point M), starting from ethyl 8-(2-benzyloxymethyl-2,3-dihydrobenzofuran-5-carboxamido)-4-oxo-4H-1-benzopyran-2-carboxylate, the title compound was prepared as a yellow solid with melting point 184–188° C. (60% yield).

$^1$H N.M.R. (300 MHz, CD$_3$OD/CDCl$_3$ mixtures) δ ppm: 3.12 (dd, 1H); 3.36 (dd, 1H); 3.70 (dd, 1H); 3.73 (dd, 1H); 4.63 (s, 2H); 5.11 (m, 1H); 6.91 (d, 1H); 7.10 (s, 1H); 7.30–7.38 (sc, 5H); 7.49 (t, 1H); 7.82 (s, 1H); 7.85 (s, 1H); 7.90 (dd, 1H); 8.73 (dd, 1H).

Example 7

N-[4-Oxo-2-(1H-5-tetrazolyl)-4H-1-benzopyran-8-yl]-2-benzyloxymethyl-2,3-dihydrobenzofuran-5-carboxamide

7A N-[4-Oxo-2-carbamoyl-4H-1-benzopyran-8-yl]-2-benzyloxymethyl-2,3-dihydrobenzofuran-5-carboxamide In a solution of ethyl 8-(2-benzyloxymethyl-2,3-dihydrobenzofuran-5-carboxamido)-4-oxo-4H-1-benzopyran-2-carboxylate (528 mg, 1.06 mmol) in methanol (25 ml) and anhydrous tetrahydrofuran (25 ml), ammonia gas was bubbled for 30 minutes. After evaporation to dryness, the resulting solid residue was dissolved in a tetrahydrofuran:methanol 1:1 mixture (15 ml) and added with concentrated HCl (0.5 ml). The mixture was refluxed under stirring for 1.5 h, then the solvents were evaporated off under reduced pressure. The resulting crude was suspended in water and the insoluble solid was recovered by filtration, washed repeatedly with water and dried under vacuum on phosphorous pentoxyde, thereby obtaining 527 mg of the title compound (quantitative yield).

$^1$H N.M.R. (300 MHz, DMSO) δ ppm: 3.08 (dd, 1H); 3.36 (dd, 1H); 3.70 (m, 2H); 4.57 (s, 2H); 5.12 (m, 1H); 6.84 (s, 1H); 6.92 (d, 1H); 7.28–7.38 (sc, 5H); 7.53 (t, 1H); 7.83–7.89 (sc, 4H); 8.24 (broad s, 1H); 8.32 (d, 1H); 8.65 (broad s, 1H).

7B N-[4-Oxo-2-cyano-4H-1-benzopyran-8-yl]-2-benzyloxymethyl-2,3-dihydrobenzofuran-5-carboxamide Following the process described in example 2 (point D), starting from N-[4-oxo-2-carbamoyl-4H-1-benzopyran-8-yl]-2-benzyloxymethyl-2,3-dihydrobenzofuran-5-carboxamide, the title compound was prepared, which was purified by chromatography through a silica gel column, eluting with petroleum ether:chloroform mixtures of increasing polarity (56% yield).

$^1$H N.M.R. (300 MHz, CDCl$_3$) δ ppm: 3.12 (dd, 1H); 3.35 (dd, 1H); 3.71 (m, 2H); 4.64 (dd, 2H); 5.10 (m, 1H); 6.85 (s, 1H); 6.92 (d, 1H); 7.28–7.35 (sc, 5H); 7.50 (t, 1H); 7.73 (d, 1H); 7.77 (s, 1H); 7.88 (dd, 1H); 8.30 (s, 1H); 8.83 (d, 1H).

7C N-[4-Oxo-2-(1H-5-tetrazolyl)-4H-1-benzopyran-8-yl]-2-benzyloxymethyl- 2,3-dihydrobenzofuran-5-carboxamide A mixture of N-[4-oxo-2-cyano-4H-1-benzopyran-8-yl]-2-benzyloxymethyl-2,3-dihydrobenzofuran-5-carboxamide (300 mg, 0.66 mmol), sodium azide (129 mg, 1.99 mmol), ammonium chloride (107 mg, 1.99 mmol) and dry N,N-dimethylformamide (10 ml) was left under stirring at 100° C. for 1.25 h. After that the mixture, cooled at room temperature, was poured onto a 1M hydrochloric acid solution (10 ml), recovering by filtration the formed precipitate, thereby obtaining 111 mg of the title compound as a white solid with melting point 200–202° C., which was purified by crystallization in methanol:dichloromethane mixtures (68% yield).

$^1$H N.M.R. (300 MHz, DMSO) δ ppm: 3.09 (dd, 1H); 3.37 (dd, 1H); 3.70 (m, 2H); 4.58 (s, 2H); 5.13 (m, 1H); 6.94 (d, 1H); 7.14 (s, 1H); 7.28–7.35 (sc, 5H); 7.57 (t, 1H); 7.87–7.95 (m, 3H); 8.25 (dd, 1H); 10.00 (s, 1H).

Example 8

8-[2-(3-Phenylpropyl)-2,3-dihydrobenzofuran-5-carboxamido]-4-oxo-4H-1-benzopyran-2-carboxylic acid

8A Ethyl 2-trifluoromethanesulfonyloxymethyl-2,3-dihydrobenzofuran-5-carboxylate Following the process described in example 3 (point A), starting from ethyl 2-hydroxymethyl-2,3- dihydrobenzofuran-5-carboxylate, the title compound was prepared (88% yield).

$^1$H N.M.R. (300 MHz, CDCl$_3$) δ ppm: 1.38 (t, 3H); 3.07 (dd, 1H); 3.44 (dd, 1H); 4.34 (q, 2H); 4.60 (dd, 1H); 4.67 (dd, 1H); 5.17 (m, 1H); 6.84 (d, 1H); 7.90 (s, 1H); 7.91 (d, 1H).

8B Ethyl 2-(3-phenylpropyl)-2,3-dihydrobenzofuran-5-carboxylate

Following the process described in example 3 (point B), starting from ethyl 2-trifluoromethanesulfonyloxymethyl-2,3-dihydrobenzofuran-5-carboxylate and 2-bromoethylbenzene, the title compound was prepared, which was purified by chromatography through a silica gel column, eluting with n-hexane:ethyl acetate, 95:5 (75% yield).

$^1$H N.M.R. (300 MHz, CDCl$_3$) δ ppm: 1.31 (t, 3H); 1.60–1.83 (m, 4H); 2.60 (t, 2H), 2.73 (dd, 1H); 3.15 (dd, 1H); 4.29 (q, 2H); 4.74 (m, 1H); 6.70 (d, 1H); 7.10–7.29 (sc, 5H); 7.80 (s, 1H); 7.82 (d, 1H).

8C 2-(3-Phenylpropyl)-2,3-dihydrobenzofuran-5-carboxylic acid

Following the process described in example 6 (point E), starting from ethyl 2-(3-phenylpropyl)-2,3-dihydrobenzofuran-5-carboxylate, the title compound was prepared (98% yield).

$^1$H N.M.R. (300 MHz, CD$_3$OD) δ ppm: 1.60–1.85 (m, 4H); 2.62 (t, 2H), 2.76 (dd, 1H); 3.21 (dd, 1H); 4.78 (m, 1H); 6.65 (d, 1H); 7.10–7.29 (sc, 5H); 7.81 (sc, 2H).

8D N-(3-Acetyl-2-hydroxyphenyl)-2-(3-phenylpropyl)2,3-dihydrobenzofuran-5-carboxamide Following the process described in example 1 (point K), starting from 2-(3-phenylpropyl)-2,3-dihydrobenzofuran-5-carboxylic acid and 3-amino-2-hydroxyacetophenone, the title compound was prepared (60% yield).

$^1$H N.M.R. (300 MHz, CDCl$_3$) δ ppm: 1.60–1.85 (m, 4H); 2.55 (s, 3H); 2.63 (t, 2H); 2.80 (dd, 1H); 3.22 (dd, 1H); 4.79 (m, 1H); 6.71 (d, 1H); 6.86 (t, 1H); 7.11–7.25 (sc, 5H); 7.38 (d, 1H); 7.62 (d, 1H); 7.64 (s, 1H); 8.34 (s, 1H); 8.66 (d, 1H).

8E Ethyl 8-[2-(3-phenylpropyl)-2,3-dihydrobenzofuran-5-carboxamido]-4-oxo-4H-1-benzopyran-2-carboxylate Following the process described in example 1 (point A), starting from N-(3-acetyl-2-hydroxyphenyl)-2-(3-phenylpropyl)-2,3-dihydrobenzofuran-5-carboxamide and diethyl oxalate, the title compound was prepared, which was purified by crystallization in hot ethanol (67% yield).

$^1$H N.M.R. (300 MHz, CDCl$_3$) δ ppm: 1.45 (t, 3H); 1.70–1.92 (m, 4H); 2.71 (t, 2H); 2.93 (dd, 1H); 3.38 (dd, 1H); 4.50 (q, 2H); 4.93 (m, 1H); 6.85 (d, 1H); 7.16 (s, 1H); 7.18–7.32 (sc, 5H); 7.47 (t, 1H); 7.77 (dd, 1H); 7.84 (s, 1H); 7.87 (dd, 1H); 8.71 (s, 1H); 8.93 (dd, 1H).

8F 8-[2-(3-Phenylpropyl)-2,3-dihydrobenzofuran-5-carboxamido]-4-oxo-4H-1-benzopyran-2-carboxylic acid Following the process described in example 1 (point M), starting from ethyl 8-[2-(3-phenylpropyl)-2,3-dihydrobenzofuran-5-carboxamido]-4-oxo-4H-1-benzopyran-2-carboxylate, the title compound was prepared as a yellow solid with melting point 184–185° C., which was purified by digestion in methanol (41% yield).

$^1$H N.M.R. (300 MHz, DMSO) δ ppm: 1.65–1.85 (m, 4H); 2.68 (t, 2H); 2.91 (dd, 1H); 3.38 (dd, 1H); 4.95 (m, 1H); 6.88 (d, 1H); 6.94 (s, 1H); 7.15–7.32 (sc, 5H); 7.54 (t, 1H); 7.83 (dd, 1H); 7.88 (m, 2H); 8.07 (dd, 1H); 10.01 (s, 1H).

Example 9

N-[4-Oxo-2-(1H-5-tetrazolyl)-4H-1-benzopyran-8-yl]-2-(3-phenylpropyl)-2,3-dihydrobenzofuran-5-carboxamide

9A N-[4-Oxo-2-carbamoyl-4H-1-benzopyran-8-yl]-2-(3-phenylpropyl)-2,3-dihydrobenzofuran-5-carboxamide Following the process described in example 7 (point A), starting from ethyl 8-[2-(3-phenylpropyl)-2,3-dihydrobenzofuran-5-carboxamido]-4-oxo-4H-1-benzopyran-2-carboxylate, the title compound was prepared (quantitative yield).

$^1$H N.M.R. (300 MHz, DMSO) δ ppm: 1.65–1.85 (m, 4H); 2.68 (t, 2H); 2.91 (dd, 1H); 3.38 (dd, 1H); 4.95 (m, 1H); 6.85 (s, 1H); 6.88 (d, 1H); 7.15–7.32 (sc, 5H); 7.55 (t, 1H); 7.82–7.95 (m, 3H); 8.24 (broad s, 1H); 8.30 (d, 1H); 8.75 (broad s, 1H).

9B N-[4-Oxo-2-cyano-4H-1-benzopyran-8-yl]-2-(3-phenylpropyl)-2,3-dihydrobenzofuran-5-carboxamide Following the process described in example 2 (point D), starting from N-[4-oxo-2-carbamoyl-4H-1-benzopyran-8-yl]-2-(3-phenylpropyl)-2,3-dihydrobenzofuran-5-carboxamide, the title compound was prepared, which was purified by chromatography through a silica gel column, eluting with petroleum ether:ethyl ether mixtures of increasing polarity (55% yield).

$^1$H N.M.R. (300 MHz, CDCl$_3$) δ ppm: 1.70–1.95 (m, 4H); 2.71 (t, 2H); 2.90 (dd, 1H); 3.34 (dd, 1H); 5.00 (m, 1H); 6.80 (s, 1H); 6.84 (d, 1H); 7.15–7.32 (sc, 5H); 7.48 (t, 1H); 7.70 (d, 1H); 7.74 (s, 1H); 7.86 (d, 1H); 8.32 (s, 1H); 8.80 (d, 1H).

9C N-[4-Oxo-2-(1H-5-tetrazolyl)-4H-1-benzopyran-8-yl]-2-(3-phenylpropyl)-2,3-dihydrobenzofuran-5-carboxamide Following the process described in example 7 (point C), starting from N-[4-oxo-2-cyano-4H-1-benzopyran-8-yl]-2-(3-phenylpropyl)-2,3-dihydrobenzofuran-5-carboxamide, the title compound was prepared as a yellowish solid with melting point 234–235° C., which was purified by crystallization in methanol:dichloromethane mixtures (61% yield).

$^1$H N.M.R. (300 MHz, DMSO) δ ppm: 1.65–1.85 (m, 4H); 2.66 (t, 2H); 2.92 (dd. 1H); 3.39 (dd, 1H); 4.96 (m, 1H); 6.90 (d, 1H); 7.14 (s, 1H); 7.15–7.32 (sc, 5H); 7.56 (t, 1H); 7.87 (dd, 1H); 7.90 (d, 1H); 7.92 (s, 1H); 8.24 (dd, 1H); 9.98 (s, 1H).

Example 10

8-(2-Benzylthiomethyl-2-dihydrobenzofuran-5-carboxamido)-4-oxo-4H-1-benzopyran-2-carboxylic acid

10A Ethyl 2-benzylthiomethyl-2,3-dihydrobenzofuran-2-carboxylate

A solution of benzylmercaptan (0.992 ml, 8.47 mmol) in absolute ethanol (10 ml) under inert atmosphere was added with a solution of potassium hydroxide (0.712 g, 12.7 mmol) in absolute ethanol (10 ml). After 15 min. under stirring at room temperature, a solution of ethyl trifluoromethanesulfonyloxymethyl-2,3-dihydrobenzofuran-5-carboxylate (3.00 g, 8.47 mmol) in ethanol (15 ml) was added. The resulting mixture was left under stirring at room temperature for 24 h. After that the volatiles were evaporated off under reduced pressure, the resulting residue was partitioned in a mixture of water (50 ml) and ethyl acetate (50 ml) and the aqueous phase was extracted with ethyl acetate (3×40 ml). The combined organic phases were dried and the solvent was evaporated off under reduced pressure, to obtain 2.810 g of the title compound as a dark oil (quantitative yield).

$^1$H N.M.R. (300 MHz, CDCl$_3$) δ ppm: 1.34 (t, 3H); 2.68 (dd, 1H); 2.77 (dd, 1H); 2.98 (dd, 1H); 3.25 (dd, 1H); 3.78 (s, 2H); 4.31 (q, 2H); 4.92 (m, 1H); 6.76 (d, 1H); 7.19–7.27 (sc, 5H); 7.82 (s, 1H); 7.86 (dd, 1H).

10B 2-Benzylthiomethyl-2,3-dihydrobenzofuran-2-carboxylic acid

A solution of ethyl 2-benzylthiomethyl-2,3-dihydrobenzofuran-2-carboxylate (2.70 g, 8.53 mmol) in ethanol (100 ml) was added with a solution of 1M potassium hydroxide. (42.6 ml). The mixture was refluxed under stirring for 3 h, after that was neutralized with 1M HCl and ethanol was evaporated off under reduced pressure. The resulting crude was suspended in water (30 ml) and extracted with ethyl acetate (4×30 ml). The organic phase was dried and the solvent was evaporated off under reduced pressure, to obtain 2.172 g of the title compound as a brown solid with melting point 125–127° C. (85% yield).

$^1$H N.M.R. (300 MHz, CDCl$_3$) δ ppm: 2.70 (dd, 1H); 2.81 (dd, 1H); 3.02 (dd, 1H); 3.32 (dd, 1H); 3.79 (s, 2H); 4.98 (m, 1H); 6.80 (d, 1H); 7.20–7.27 (sc, 5H); 7.89 (s, 1H); 7.97 (d, 1H).

10C N-(3-Acetyl-2-hydroxyphenyl)-2-benzylthiomethyl-2,3-dihydrobenzofuran-5-carboxamide Following the process described in example 1 (point K), starting from 2-benzylthiomethyl-2,3-dihydrobenzofuran-2-carboxylic acid and 3-amino-2-hydroxyacetophenone, the title compound was prepared as a yellow solid with melting point 119–121° C., which was purified by chromatography through a silica gel column, eluting with n-hexane:ethyl acetate, 90:10 (86% yield).

$^1$H N.M.R. (300 MHz, CDCl$_3$) δ ppm: 2.61 (s, 3H); 2.68 (dd, 1H); 2.80 (dd, 1H); 3.06 (dd, 1H); 3.34 (dd, 1H); 3.79 (s, 3H); 4.95 (m, 1H); 6.83 (d, 1H); 6.93 (t, 1H); 7.21–7.35 (sc, 5H); 7.46 (d, 1H); 7.72 (d, 1H); 7.73 (s, 1H); 8.53 (s, 1H); 8.74 (d, 1H).

10D Ethyl 8-(2-benzylthiomethyl-2,3-dihydrobenzofuran-5-carboxamido)-4-oxo-4H-1-benzopyran-2-carboxylate Following the process described in example 1 (point A), starting from N-(3-acetyl-2-hydroxyphenyl)-2-benzylthiomethyl-2,3-dihydrobenzofuran-5-carboxamide and diethyl oxalate, the title compound was prepared as a slightly yellow solid with melting point 175–177° C., which was purified by chromatography through a silica gel column, eluting with chloroform (81% yield).

$^1$H N.M.R. (300 MHz, CDCl$_3$) δ ppm: 1.47 (t, 3H); 2.72 (dd, 1H); 2.34 (dd, 1H); 3.09 (dd, 1H); 3.38 (dd, 1H); 3.80 (s, 3H); 4.49 (q, 2H); 4.99 (m, 1H); 6.85 (d, 1H); 7.12 (s, 1H); 7.21–7.35 (sc, 5H); 7.43 (t, 1H); 7.76 (d, 1H); 7.80 (s, 1H); 7.85 (d, 1H); 8.70 (s, 1H); 8.89 (d, 1H).

10 E 8-(2-Benzylthiomethyl-2,3-dihydrobenzofuran-5-carboxamido)-4-oxo-4H-1-benzopyran-2-carboxylic acid Following the process described in example 1 (point M), starting from ethyl 8-(2-benzylthiomethyl-2,3-dihydrobenzofuran-5-carboxamido)-4-oxo-4H-1-benzopyran-2-carboxylate, the title compound was prepared as a yellow solid with melting point 122–125° C. (81% yield).

$^1$H N.M.R. (300 MHz, DMSO) δ ppm: 2.80 (d, 2H); 3.05 (dd, 1H); 3.20 (dd, 1H); 3.85 (s, 3H); 5.08 (m, 1H); 6.91 (s, 1H); 6.92 (d, 1H); 7.27 (m, 1H); 7.34 (d, 4H); 7.54 (t, 1H); 7.86 (d, 1H); 7.88 (d, 1H); 7.90 (s, 1H); 8.08 (dd, 1H); 10.04 (s, 1H).

Example 11

8-[2-4'-Fluorobenzyloxymethyl)-2,3-dihydrobenzofuran-5-carboxamido]-4-oxo-4H-1-benzopyran-2-carboxylic acid

11A Ethyl 2-(4'-fluorobenzyloxymethyl)-2,3-dihydrobenzofuran-2-carboxylate

Following the process described in example 1 (point D), starting from ethyl 2-hydroxymethyl-2,3-dihydrobenzofuran-5-carboxylate and 4'-fluorobenzyl bromide, the title compound was prepared, which was purified by chromatography through a silica gel column, eluting with n-hexane:ethyl acetate, 95:5 (68% yield).

$^1$H N.M.R. (300 MHz, CDCl$_3$) δ ppm: 1.34 (t, 3H); 2.99 (dd, 1H); 3.23 (dd, 1H); 3.62 (dd, 1H); 3.68 (dd, 1H); 4.30 (q, 2H); 4.52 (dd, 2H); 5.03 (m, 1H); 6.79 (d, 1H); 7.00 (t, 2H); 7.26 (dd, 2H); 7.83 (s, 1H); 7.87 (dd, 1H).

11B 2-(4'-Fluorobenzyloxymethyl)-2,3-dihydrobenzofuran-2-carboxylic acid

Following the process described in example 6 (point E), starting from ethyl 2-(4'-fluorobenzyloxymethyl)-2,3-dihydrobenzofuran-2-carboxylate, the title compound was prepared, which was purified by crystallization in methanol (94% yield).

$^1$H N.M.R. (300 MHz, CDCl$_3$) δ ppm: 3.01 (dd, 1H); 3.27 (dd, 1H); 3.65 (m, 2H); 4.58 (dd, 2H); 5.05 (m, 1H); 6.81 (d, 1H); 7.00 (t, 2H); 7.27 (dd, 2H); 7.86 (s, 1H); 7.92 (dd, 1H); 12.20 (broad signal, 1H).

11C N-(3-Acetyl-2-hydroxyphenyl)-2-(4'-fluorobenzyloxymethyl)-2,3-dihydrobenzofuran-5-carboxamide Following the process described in example 1 (point K), starting from 2-(4'-fluorobenzyloxymethyl)-2,3-dihydrobenzofuran-2-carboxylic acid, the title compound was prepared which was purified by chromatography through a silica gel column, eluting with n-hexane:chloroform, 1:1 (81% yield).

$^1$H N.M.R. (300 MHz, CDCl$_3$) δ ppm: 2.60 (s, 3H); 3.05 (dd, 1H); 3.30 (dd, 1H); 3.65 (m, 2H); 4.58 (dd, 2H); 5.05 (m, 1H); 6.84 (d, 1H); 6.92 (t, 1H); 7.01 (t, 2H); 7.27 (m, 2H); 7.43 (d, 1H); 7.71 (d, 1H); 7.73 (s, 1H); 8.51 (s, 1H); 8.71 (d, 1H); 12.96 (s, 1H).

11D Ethyl 8-[2-(4'-fluorobenzyloxymethyl)-2,3-dihydrobenzofuran-5-carboxamido)-4-oxo-4H-1-benzopyran-2-carboxylate Following the process described in example 1 (point A), starting from N-(3-acetyl-2-hydroxyphenyl)-2-(4'- fluorobenzyloxymethyl)-2,3-dihydrobenzofuran-5-carboxamide and diethyl oxalate, the title compound was prepared, which was purified by chromatography through a silica gel column, eluting with n-hexane:chloroform, 1:2 (53% yield).

$^1$H N.M.R. (300 MHz,: CDCl$_3$) δ ppm: 1.46 (t, 3H); 3.10 (dd, 1H); 3.35 (dd, 1H); 3.70 (m, 2H); 4.49 (q, 2H); 4.58 (dd, 2H); 5.10 (m, 1H); 6.88 (d, 1H); 7.01 (t, 2H); 7.13 (s, 1H); 7.30 (m, 2H); 7.44 (t, 1H); 7.77 (dd, 1H); 7.83 (s, 1H); 7.87 (d, 1H); 8.71 (s, 1H); 8.90 (d, 1H).

11E 8-[2-(4'-Fluorobenzyloxymethyl)-2,3-dihydrobenzofuran-5-carboxamido]-4-oxo-4H-1-benzopyran-2-carboxylic acid Following the process described in example 1 (point M), starting from ethyl 8-[2-(4'-fluorobenzyloxymethyl)-2,3-dihydrobenzofuran-5-carboxamido)-4-oxo-4H-1-benzopyran-2-carboxylate, the title compound was prepared as a yellow solid with melting point 195–197° C., which was purified by crystallization in methanol.

$^1$H N.M.R. (300 MHz, DMSO) δ ppm: 3.10 (dd, 1H); 3.37 (dd, 1H); 3.68 (d, 2H); 4.56 (s, 2H); 5.12 (m, 1H); 6.91 (d, 1H); 6.95 (s, 1H); 7.17 (t, 2H); 7.38 (t, 2H); 7.54 (t, 1H); 7.88 (sc, 3H); 8.08 (dd, 1H); 10.03 (s, 1H).

Example 12

N-[4-Oxo-2-(1H-5-tetrazolyl)-4H-1-benzopyran-8-yl]-2-(4'-fluorobenzyloxymethyl)-2,3-dihydrobenzofuran-5-carboxamide, 12A N-[4-Oxo-2-carbamoyl-4H-1-benzopyran-8-yl]-2-(4'-fluorobenzyloxymethyl)-2,3-dihydrobenzofuran-5-carboxamide A solution of ethyl 8-[2-(4'-fluorobenzyloxymethyl)-2,3-dihydrobenzofuran-5-carboxamido]-4-oxo-4H-1-benzopyran-2-carboxylate (1.219 g, 2.36 mmol) in dry tetrahydrofuran (1.00 ml) at −20° C. was added with a saturated ammonia solution in methanol (12 ml, approximately 4M solution). The resulting mixture was left under stirring at0° C. for 4 h, then the solvents were removed, to obtain 1.158 g of the title compound (quantitative yield).

$^1$H N.M.R. (300 MHz, DMSO) δ ppm: 3.09 (dd, 1H); 3.35 (dd, 1H); 3.67 (s, 2H); 4.56 (s, 2H); 5.11 (m, 1H); 6.87 (s, 1H); 6.92 (d, 1H); 7.18 (t, 2H); 7.38 (t, 2H); 7.53 (t, 1H); 7.84 (sc, 3H); 8.25 (broad s, 1H); 8.38 (d, 1H); 8.60 (broad s, 1H); 10.25 (s, 1H).

12B N-[4-Oxo-2-cyano-4H-1-benzopyran-8-yl]-2-(4'-fluorobenzyloxymethyl-2,3-dihydrobenzofuran-5-carboxamide Following the process described in example 2 (point D), by reacting N-[4-oxo-2-carbamoyl-4H-1-benzopyran-8yl]-2-(4'-fluorobenzyloxymethyl)-2,3-dihydrobenzofuran-5-carboxamide with phosphorous oxychloride in DMF for 0.5 h at 0° C., the title compound was prepared, which was purified by chromatography through a silica gel column, eluting with petroleum ether:chloroform, 1:1 (77% yield).

$^1$H N.M.R. (300 MHz, CDCl$_3$) δ ppm: 3.10 (dd, 1H); 3.33 (dd, 1H); 3.70 (m, 2H); 4.59 (dd, 2H); 5.10 (m, 1H); 6.82 (s, 1H); 6.89 (d, 1H); 7.02 (t, 2H); 7.38 (m, 2H); 7.48 (t, 1H); 7.72 (dd, 1H); 7.78 (s, 1H); 7.88 (d, 1H); 8.35 (s, 1H); 8.79 (d, 1H).

12C N-[4-Oxo-2-(1H-5-tetrazolyl)-4H-1-benzopyran-8-yl]-2-(4'-fluorobenzyloxymethyl)-2,3-dihydrobenzofuran-5-carboxamide Following the process described in example 7 (point C), starting from N-[4-oxo-2-cyano-4H-1-benzopyran-8-yl]-2-(4'-fluorobenzyloxymethyl)-2,3-dihydrobenzofuran-5-carboxamide, the title compound was prepared as a white solid with melting point 229–232° C., which was purified by digestion in ethyl ether (77% yield).

$^1$H N.M.R. (300 MHz, DMSO) δ ppm: 3.12 (dd, 1H); 3.40 (dd, 1H); 3.72 (d, 2H); 4.60 (dd, 2H); 5.12 (m, 1H); 6.93 (d, 1H); 7.05 (t, 2H); 7.25 (s, 1H); 7.33 (m, 2H); 7.52 (t, 1H); 7.89 (d, 1H); 7.92 (s, 1H); 7.96 (dd, 1H); 8.73 (d, 1H); 10.05 (s, 1H).

Example 13

8-[7Chloro-2-(3-phenylpropyl)-2,3-dihydrobenzofuran-5-carboxamido]-4-oxo-4H-1-benzopyran-2-carboxylic acid 13A Methyl 3-chloro-4-hydroxybenzoate Following the process described in example 5 (point C), starting from 3-chloro-4-hydroxybenzoic acid, the title compound was prepared (87% yield).

$^1$H N.M.R. (300 MHz, CDCl$_3$) δ ppm: 1.39 (t, 3H); 4.37 (q, 2H); 7.04 (d, 1H); 7.89 (dd, 1H); 8.06 (d, 1H).

13B Ethyl 4-allyloxy-3-chlorobenzoate

Following the process described in example 6 (point A), starting from ethyl 3-chloro-4-hydroxybenzoate, the title compound was prepared (91% yield).

$^1$H N.M.R. (300 MHz, CDCl$_3$) δ ppm: 1.39 (t, 3H); 4.37 (q, 2H); 4.69 (d, 2H); 5.35 (dd, 1H); 5.49 (dd, 1H); 6.07 (m, 1H); 6.94 (d, 1H); 7.91 (dd, 1H); 8.07 (d, 1H).

13C Ethyl 3-allyl-5-chloro-4-hydroxybenzoate

Following the process described in example 6 (point B), starting from ethyl 4-allyloxy-3-chlorobenzoate, the title compound was prepared, which was purified by distillation under reduced pressure (0.2 torr) (quantitative yield).

$^1$H N.M.R. (300 MHz, CDCl$_3$) δ ppm: 1.38 (t, 3H); 3.45 (d, 2H); 4.35 (q, 2H); 5.09 (d, 1H); 5.14 (d, 1H); 6.01 (m, 1H); 7.76 (d, 1H); 7.92 (d, 1H).

13D Ethyl 7-chloro-2-hydroxymethyl-2,3-dihydrobenzofuran-5-carboxylate

Following the process described in example 6 (point C), starting from ethyl 3-allyl-5-chloro-4-hydroxybenzoate, the title compound was prepared (80% yield).

$^1$H N.M.R. (300 MHz, CDCl$_3$) δ ppm: 1.37 (t, 3H); 3.19 (dd, 1H); 3.33 (dd, 1H); 3.78 (dd, 1H); 3.97 (dd, 1H); 4.33 (q, 2H); 5.09 (m, 1H); 7.74 (d, 1H); 7.85 (d, 1H).

13E Ethyl 7-chloro-2-trifluoromethansulfonyloxymethyl-2,3-dihydrobenzofuran-5-carboxylate Following the process described in example 3 (point A), starting from ethyl 7-chloro-2-hydroxymethyl-2,3-dihydrobenzofuran-5-carboxylate, the title compound was prepared (quantitative yield).

$^1$H N.M.R. (300 MHz, CDCl$_3$) δ ppm: 1.38 (t, 3H); 3.20 (dd, 1H); 3.53 (dd, 1H); 4.32 (q, 2H); 4.67 (dd, 1H); 4.77 (dd, 1H); 5.28 (m, 1H); 7.76 (d, 1H); 7.88 (d, 1H).

13F Ethyl 7-chloro-2-(3-phenylpropyl)-2,3-dihydrobenzofuran-5-carboxylate

Following the process described in example 3 (point B), starting from ethyl 7-chloro-2- trifluoromethanesulfonyloxymethyl-2,3-dihydrobenzofuran-5-carboxylate and 2-bromoethylbenzene, the title compound was prepared, which was purified by chromatography through a silica gel column, eluting with petroleum ether:ethyl acetate, 95:5 (58% yield).

$^1$H N.M.R. (300 MHz, CDCl$_3$) δ ppm: 1.36 (t, 3H); 1.70–1.92 (m, 4H); 2.68 (t, 2H), 2.91 (dd, 1H); 3.34 (dd, 1H); 4.32 (q, 2H); 4.95 (m, 1H); 7.15–7.30 (sc, 5H); 7.71 (d, 1H); 7.86 (d, 1H).

13G 2-(3-Phenylpropyl-2,3-dihydrobenzofuran-5-carboxylic acid

Following the process described in example 6 (point E), starting from ethyl 7-chloro-2-(3-phenylpropyl)-2,3-dihydrobenzofuran-5-carboxylate, the title compound was prepared (92% yield).

$^1$H N.M.R. (300 MHz, CD$_3$OD) δ ppm: 1.70–1.92 (m, 4H); 2.70 (t, 2H), 2.95 (dd, 1H); 3.40 (dd, 1H); 4.99 (m, 1H); 7.15–7.30 (sc, 5H); 7.73 (d, 1H); 7.,83 (d, 1H).

13H N-(3-Acetyl-2-hydroxyphenyl)-7-chloro-2-(3-phenylpropyl)-2,3-dihydrobenzofuran-5-carboxamide Following the process described in example 1 (point K), starting from 7-chloro-2-(3-phenylpropyl)-2,3-dihydrobenzofuran-5-carboxylic acid, the title compound was prepared, which was purified by chromatography through a silica gel column, eluting with petroleum ether:chloroform, 1:1 (84% yield).

$^1$H N.M.R. (300 MHz, CDCl$_3$) δ ppm: 1.60–1.88 (m, 4H); 2.50 (s, 3H); 2.63 (t, 2H); 2.82 (dd, 1H); 3.24 (dd, 1H); 4.84 (m, 1H); 6.79 (t, 1H); 7.11–7.25 (sc, 5H); 7.29 (d, 1H); 7.45 (s, 1H); 7.63 (s, 1H); 8.38 (s, 1H); 8.58 (d, 1H).

13I Ethyl 8-[7-chloro-2-(3-phenylpropyl)-2,3-dihydrobenzofuran-5-carboxamido]-4-oxo-4H-1-benzopyran-2-carboxylate Following the process described in example 1 (point A), starting from N-(3-acetyl-2-hydroxyphenyl)-7-chloro-2-(3-phenylpropyl)-2,3-dihydrobenzofuran-5-carboxamide, the title compound was prepared, which was purified by chromatography through a silica gel column, eluting with petroleum ether:chloroform mixtures of increasing polarity (57% yield).

$^1$H N.M.R. (300 MHz, CDCl$_3$)u δ ppm: 1,47 (t, 3H); 1.76–1.96 (m, 4H); 2.72 (t, 2H); 3.01 (dd, 1H); 3.44 (dd, 1H); 4.51 (q, 2H); 5.03 (m, 1H); 7.16 (s, 1H); 7.19–7.33 (sc, 5H); 7.47 (t, 1H); 7.71 (s, 1H); 7.79 (s, 1H); 7.89 (dd, 1H); 8.66 (s, 1H); 8.88 (dd, 1H).

13J 8-[7Chloro-2-(3phenylpropyl)-2,3-dihydrobenzofuran-5-carboxamido]-4-oxo-4H-1-benzopyran-2-carboxylic acid Following the process described in example 1 (point M), starting from ethyl 8-[7-chloro-2-(3-phenylpropyl)-2,3-dihydrobenzofuran-5-carboxamido]-4-oxo-4H-1-benzopyran-2-carboxylate, the title compound was prepared as a white solid with melting point 224–225° C., which was purified by chromatography through a silica gel column, eluting with chloro:form:methanol, 98:2 (54% yield).

$^1$H N.M.R. (300 MHz, CD$_3$OD/CDCl$_3$ mixtures) δ ppm: 1.75– 1.95 (m, 4H); 2.73 (t, 2H); 3.02 (dd, 1H); 3.46 (dd, 1H); 5.04 (m, 1H); 7.15 (s, 1H); 7.19–7.32 (sc, 5H); 7.50 (t, 1H); 7.74 (d, 1H); 7.85 (d, 1H); 7.94 (dd, 1H); 8.53 (dd, 1H).

Example 14

8-[2-(3-Phenylpropyl)-2,3-dihydrobenzofuran-5-carboxamido]-6-fluoro-4-oxo-4H-1-benzopyran-2-carboxylic acid

14A 4-Fluorophenyl acetate

Following the process described in example 1 (point G), starting from 4-fluorophenol, the title compound was prepared as a colourless oil (94% yield).

$^1$H N.M.R. (300 MHz, CDCl$_3$) δ ppm: 2.29 (s, 3H); 7.06 (d, 4H).

14B 5-Fluoro-2-hydroxyacetophenone

Following the process described in example 1 (point H), starting from 4-fluorophenyl acetate, the title compound was prepared as a white solid with melting point 55–58° C., which was purified by chromatography through a silica gel column, eluting with petroleum ether:chloroform, 9:1 (78% yield).

$^1$H N.M.R. (300 MHz, CDCl$_3$) δ ppm: 2.62 (s, 3H); 6.95 (dd, 1H); 7.22 (dt, 1H); 7.40 (dd, 1H); 11.98 (s, 1H).

14C 5-Fluoro-2-hydroxy-3-nitroacetophenone

Following the process described in example 1 (point I), starting from 5-fluoro-2-hydroxyacetophenone, the title compound was prepared as a yellow solid which was purified by chromatography through a silica gel column, eluting with petroleum ether:chloroform, 1:1 (52% yield).

$^1$H N.M.R. (300 MHz, CDCl$_3$) δ ppm: 2.72 (s, 3H); 7.81 (dd, 1H); 7.96 (d, 1H); 12.62 (s, 1H).

14D 3-Amino-5-fluoro-2-hydroxyacetophenone

Following the process described in example 1 (point B), starting from 5-fluoro-2-hydroxy-3-nitroacetophenone, the title compound was prepared (quantitative yield).

$^1$H N.M.R. (300 MHz, CD$_3$OD) δ ppm: 2.55 (s, 3H); 6.68 (dd, 1H); 7.84 (dd, 1H).

14E N-(3-Acetyl-5-fluoro-2-hydroxyphenyl)-2-(3-phenylpropyl)-2,3-dihydrobenzofuran-5-carboxamide Following the process described in example 1 (point K), starting from 2-(3-phenylpropyl)-2,3-dihydrobenzofuran-5-carboxylic acid and 3-amino-5-fluoro-2-hydroxyacetophenone, the title compound was prepared, which was purified by chromatography through a silica gel column, eluting with petroleum ether:chloroform, 1:1 (79% yield).

$^1$H N.M.R. (300 MHz, CDCl$_3$) δ ppm: 1.70–1.95 (m, 4H); 2.58 (s, 3H); 2.70 (t, 2H); 2.89 (dd, 1H); 3.31 (dd, 1H); 4.79 (m, 1H); 6.72 (d, 1H); 7.11–7.25 (sc, 5H); 7.40 (d, 1H); 7.62 (d, 1H); 7.65 (s, 1H); 8.19 (s, 1H); 8.66 (d, 1H).

14F Ethyl 8-[2-(3-phenylpropyl)-2,3-dihydrobenzofuran-5-carboxamido]-6-fluoro-4-oxo-4H-1-benzopyran-2-carboxylate Following the process described in example 1 (point A), starting from N-(3-acetyl-5-fluoro-2-hydroxyphenyl)-2-(3-phenylpropyl)-2,3-dihydrobenzofuran-5-carboxamide and diethyl oxalate, the title compound was prepared, which was purified by crystallization in ethanol (55% yield).

$^1$H N.M.R. (300 MHz, CDCl$_3$) δ ppm: 1.48 (t, 3H); 1.70–1.92 (m, 4H); 2.79 (t, 2H); 2.90 (dd, 1H); 3.32 (dd, 1H); 4.48

(q, 2H); 4.90 (m, 1H); 6.80 (d, 1H); 7.08 (s, 1H); 7.18–7.32 (sc, 5H); 7.42 (dd, 1H); 7.69 (dd, 1H); 7.77 (s, 1H); 8.70 (dd, 1H); 8.71 (s, 1H).

14G 8-[2-(3-Phenylpropyl)-2,3-dihydrobenzofuran-5-carboxamido]-6-fluoro-4-oxo-4H-1-benzopyran-2-carboxylic acid Following the process described in example 1 (point M), starting from ethyl 8-[2-(3-phenylpropyl)-2,3-dihydrobenzofuran-5-carboxamido]-6-fluoro-4-oxo-4H-1-benzopyran-2-carboxylate, the title compound was prepared as a white solid with melting point 183–185° C., which was purified by chromatography through a silica gel column, eluting with chloroform:methanol, 95:5 (66% yield).

$^1$H N.M.R. (300 MHz, DMSO) δ ppm: 1.65–1.85 (m, 4H); 2.64 (t, 2H); 2.87 (dd, 1H); 3.31 (dd, 1H); 4.91 (m, 1H); 6.83 (d, 1H); 6.87 (s, 1H); 7.15–7.32 (sc, 5H); 7.49 (dd, 1H); 7.80 (d, 1H); 7.82 (s, 1H); 8.14 (dd, 1H); 10.17 (s, 1H).

Example 15

8-[4-Chloro-2-(3-phenylpropyl)-2,3-dihydrobenzofuran-5-carboxamido]-4-oxo-4H-1-benzopyran-2-carboxylic acid

15A 4-Allyloxy-2-chlorobenzonitrile

Following the process described in example 6 (point A), starting from 2-chloro-4-hydroxybenzonitrile, the title compound was prepared as a white solid with melting point 50–52° C. (98% yield).

$^1$H N.M.R. (300 MHz, CDCl$_3$) δ ppm: 4.59 (m, 2H); 5.35 (dd, 1H); 5.40 (dd, 1H); 6.00 (m, 1H); 6.88 (dd, 1H); 7.03 (d, 1H); 7.59 (d).

15B 5-Allyl-2-chloro-4-hydroxybenzonitrile and 3-allyl-2-chloro-4-hydroxybenzonitrile Following the process described in example 6 (point B), starting from 4-allyloxy-2-chlorobenzonitrile, a mixture of 5-allyl-2-chloro-4-hydroxybenzonitrile and 3-allyl-2-chloro-4-hydroxybenzonitrile was obtained. The two isomers were separated by chromatography through a silica gel column. Eluting with petroleum ether:ethyl ether, 8:2, the isomer 5-allyl-2-chloro-4-hydroxybenzonitrile (39% yield) was recovered and eluting with petroleum ether:ethyl ether, 6:4, the isomer 3-allyl-2-chloro-4-hydroxybenzonitrile was recovered (51% yield).

$^1$H N.M.R. (300 MHz, CDCl$_3$) δ ppm (isomer 5): 3,39 (d, 5.12–5.28 (m,2H); 5.98 (m, 1H); 7.03 (s, 1H); 7.44 (s, 1H).

$^1$H N.M.R. (300 MHz, CDCl$_3$) δ ppm (isomer 3): 3.61 (d, 5.07–5.18 (m,2H); 5.95 (m, 1H); 6.86 (d, 1H); 7.46 (d, 1H).

15C 4-Chloro-2-hydroxymethyl-2,3-dihydrobenzofuran-5-carbonitrile

Following the process described in example 6 (point C), starting from 3-allyl-2-chloro-4-hydroxybenzonitrile, the title compound was prepared (92% yield).

$^1$H N.M.R. (300 MHz, CDCl$_3$) δ ppm: 3.14 (dd, 1H); 3.32 (dd, 1H); 3.79 (dd, 1H); 3.91 (dd, 1H); 5.08 (m, 1H); 6.72 (d, 1H); 7.41 (d, 1H).

15D 4-Chloro-2-trifluoromethanesulfonyloxymethyl-2,3-dihydrobenzofuran-5-carbonitrile Following the process described in example 3 (point A), starting from 4-chloro-2-hydroxymethyl-2,3-dihydrobenzofuran-5-carbonitrile, the title compound was prepared (64% yield).

$^1$H N.M.R. (300 MHz, CDCl$_3$) δ ppm: 3.19 (dd, 1H); 3.50 (dd, 1H); 4.68 (dd, 1H); 4.70 (dd, 1H); 5.30 (m, 1H); 6.81 (d, 1H); 7.50 (d, 1H).

15E 4-Chloro-2-(3-phenylpropyl)-2,3-dihydrobenzofuran-5-carbonitrile

Following the process described in example 3 (point B), starting from 4-chloro-2-trifluoromethanesulfonyloxymethyl-2,3-dihydrobenzofuran-5-carbonitrile and 2-bromoethylbenzene, the title compound was prepared, which was purified by chromatography through a silica gel column, eluting with petroleum ether:ethyl ether, 95:5 (68% yield).

$^1$H N.M.R. (300 MHz, CDCl$_3$) δ ppm: 1.65–1.90 (m, 4H); 2.68 (t, 2H), 2.87 (dd, 1H); 3.12 (dd, 1H); 4.92 (m, 1H); 6.69 (d, 1H); 7.14–7.32 (sc, 5H); 7.40 (d, 1H).

15F 4-Chloro-2-(3-phenylpropyl)-2,3-dihydrobenzofuran-5-carboxylic acid

Following the process described in example 5 (point G), starting from, 4-chloro-2-(3-phenylpropyl)-2,3-dihydrobenzofuran-5-carbonitrile, the title compound was prepared (89% yield).

$^1$H N.M.R. (300 MHz, CDCl$_3$) δ ppm: 1.65–1.90 (m, 4H); 2.70 (t, 2H), 2.91 (dd, 1H); 3,38 (dd, 1H); 4.93 (m, 1H); 6.69 (d, 1H): 7.14–7.32 (sc, 5H); 7.98 (d, 1H).

15G N-(3-Acetyl-2-hydroxyphenyl)-4-chloro-2-(3-phenylpropyl)-2,3-dihydrobenzofuran-5-carboxamide Following the process described in example 1 (point K), starting from 4-chloro-2-(3-phenylpropyl)-2,3-dihydrobenzofuran-5-carboxylic acid and 3-amino-2-hydroxyacetophenone, the title compound was prepared (93% yield).

$^1$H N.M.R. (300 MHz, CDCl$_3$) δ ppm: 1.60–1.85 (m, 4H); 2.60 (s, 3H); 2.65 (t, 2H); 2.90 (dd, 1H); 3.32 (dd, 1H); 4.88 (m, 1H); 6.71 (d, 1H); 6.92 (t, 1H); 7.15–7.30 (sc, 5H); 7.43 (d, 1H); 7.67 (d, 1H); 8.75 (d, 1H); 8.80 (s, 1H); 12.92 (s, 1H).

15H Ethyl 8-[4-chloro-2-(3-phenylpropyl)-2,3-dihydrobenzofuran-5-carboxamido]-4-oxo-4H-1-benzopyran-2-carboxylate Following the process described in example 1 (point A), starting from N-(3-acetyl-2-hydroxyphenyl)-4-chloro-2-(3-phenylpropyl)-2,3-dihydrobenzofuran-5-carboxamide and diethyl oxalate, the title compound was prepared, which was purified by chromatography through a silica gel column, eluting with petroleum ether:chloroform, 4:6 (61% yield).

$^1$H N.M.R. (300 MHz, CDCl$_3$) δ ppm: 1.40 (t, 3H); 1.70–1.92 (m, 4H); 2.68 (t, 2H); 2.91 (dd, 1H); 3.35 (dd, 1H); 4.42 (q, 2H); 4.92 (m, 1H); 6.72 (d, 1H); 7.10 (s, 1H); 7.15–7.32 (sc, 5H); 7.40 (t, 1H); 7.85 (dd, 1H); 7.90 (d, 1H); 8.93 (d, 1H); 9.42 (s, 1H).

15I 8-[4-Chloro-2-(3-phenylpropyl)-2,3-dihydrobenzofuran-5-carboxamido]-4-oxo-4H-1-benzopyran-2-carboxylic acid Following the process described in example 1 (point M), starting from ethyl 8-[4-chloro-2-(3-phenylpropyl)-2,3- dihydrobenzofuran-5-carboxamido]-4-oxo-4H-1-benzopyran-2-carboxylate, the title compound was prepared as a yellowish solid which decomposes at 265° C. (81% yield).

$^1$H N.M.R. (300 MHz, CD$_3$OD/CDCl$_3$ mixtures) δ ppm: 1.65–1.92 (m, 4H); 2.70 (t, 2H); 2.94 (dd, 1H); 3.41 (dd, 1H); 4.92 (m, 1H); 6.75 (d, 1H); 7.11 (s, 1H); 7.15–7.35 (sc, 5H); 7.48 (m, 2H); 7.94 (d, 1H); 8.79 (d, 1H).

Example 16

8-[6-Chloro-2-(3-phenylpropyl)-2,3-dihydrobenzofuran-5-carboxamido]-4-oxo-4H-1-benzopyran-2-carboxylic acid 16A 6-Chloro-2-hydroxymethyl-2,3-dihydrobenzofuran-5-carbonitrile Following the process described in example 6 (point C), starting from 5-allyl-2-chloro-4-hydroxybenzonitrile, the title compound was prepared, which was purified by chromatography through a silica gel column, eluting with petroleum ether:chloroform, 1:4 (79% yield).

$^1$H N.M.R. (300 MHz, CDCl$_3$) δ ppm: 3.10 (dd, 1H); 3.29 (dd, 1H); 3.77 (dd, 1H); 3.92 (dd, 1H); 5.08 (m, 1H); 6.88 (d, 1H); 7.41 (s, 1H).

16B 6-Chloro-2-trifluoromethanesulfonyloxymethyl-2,3-dihydrobenzofuran-5-carbonitrile Following the process described in example 3 (point A), starting from 6-chloro-2-hydroxymethyl-2,3-dihydrobenzofuran-5-carbonitrile, the title compound was prepared (76% yield).

$^1$H N.M.R. (300 MHz, CDCl$_3$) δ ppm: 3.13 (dd, 1H); 3.49 (dd, 1H); 4.68 (dd, 1H); 4.69 (dd, 1H); 5.30 (m, 1H); 6.93 (s, 1H); 7.44 (s, 1H).

16C 6-Chloro-2-(3-phenylpropyl)-2,3-dihydrobenzofuran-5-carbonitrile

Following the process described in example 3 (point B), starting from 6-chloro-2-trifluoromethanesulfonyloxymethyl-2,3-dihydrobenzofuran-5-carbonitrile and 2-bromoethylbenzene, the title compound was prepared, which was purified by chromatography through a silica gel column, eluting with petroleum ether:ethyl ether, 9:1 (20% yield).

$^1$H N.M.R. (300 MHz, CDCl$_3$) δ ppm: 1.65–1.90 (m, 4H); 2.66 (t, 2H), 2.78 (dd, 1H); 3.23 (dd, 1H); 4.89 (m, 1H); 6.78 (d, 1H); 7.14–7.30 (sc, 6H).

16D 6-Chloro-2-(3-phenylpropyl)-2,3-dihydrobenzofuran-5-carboxylic acid

Following the process described in example 5 (point G), starting from 6-chloro-2-(3-phenylpropyl)-2,3-dihydrobenzofuran-5-carbonitrile, the title compound was prepared (77% yield).

$^1$H N.M.R. (300 MHz, CDCl$_3$) δ ppm: 1.65–1.90 (m, 4H); 2.62 (m, 3H), 3.07 (m, 1H); 4.76 (m, 1H); 6.68 (s, 1H); 7.14–7.32 (sc, 5H); 7.71 (s, 1H).

16E N-(3-Acetyl-2-hydroxyphenyl)-6-chloro-2-(3-phenylpropyl)-2,3-dihydrobenzofuran-5-carboxamide Following the process described in example 1 (point K), starting from 6-chloro-2-(3-phenylpropyl)-2,3-dihydrobenzofuran-5-carboxylic acid and 3-amino-2-hydroxyacetophenone, the title compound was prepared, which was purified by chromatography through a silica gel column, eluting with hexane:ethyl acetate, 1:1 (42% yield).

$^1$H N.M.R. (300 MHz, CDCl$_3$) δ ppm: 1.60–1.85 (m, 4H); 2.56 (s, 3H); 2.63 (t, 2H); 2.74 (dd, 1H); 3.18 (dd, 1H); 4.80 (m, 1H); 6.72 (d, 1H); 6.87 (t, 1H); 7.15–7.30 (sc, 5H); 7.38 (dd, 1H); 7.59 (s, 1H); 8.71 (d, 1H); 8.86 (s, 1H); 12.92 (s, 1H).

16F Ethyl 8-[6-chloro-2-(3-phenylpropyl)-2,3-dihydrobenzofuran-5-carboxamido]-4-oxo-4H-1-benzopyran-2-carboxylate Following the process described in example 1 (point A), starting from N-(3-acetyl-2-hydroxyphenyl)-6-chloro-2-(3-phenylpropyl)-2,3-dihydrobenzofuran-5-carboxamide and diethyl oxalate, the title compound was prepared, which was purified by chromatography through a silica gel column, eluting with petroleum ether:chloroform, 4:6 (75% yield).

$^1$H N.M.R. (300 MHz, CDCl$_3$) δ ppm: 1.42 (t, 3H); 1.70–1.92 (m, 4H); 2.68 (t, 2H); 2.85 (dd, 1H); 3.29 (dd, 1H); 4.45 (q, 2H); 4.92 (m, 1H); 6.81 (s, 1H); 7.12 (s, 1H); 7.15–7.32 (sc, 5H); 7.43 (t, 1H); 7.85 (dd, 1H); 7.86 (s, 1H); 8.93 (d, 1H); 9.52 (s, 1H).

16G 8-[6-Chloro-2-(3-phenylpropyl)-2,3-dihydrobenzofuran-5-carboxamido]-4-oxo-4H-1-benzopyran-2-carboxylic acid Following the process described in example 1 (point M), starting from ethyl 8-[6-chloro-2-(3-phenylpropyl)-2,3-dihydrobenzofuran-5-carboxamido]-4-oxo-4H-1-benzopyran-2-carboxylate, the title compound was prepared as a yellowish solid which decomposes at 265° C. (78% yield).

$^1$H N.M.R. (300 MHz, CD$_3$OD/CDCl$_3$ mixtures) δ ppm: 1.65–1.92 (m, 4H); 2.70 (t, 2H); 2.80 (dd, 1H); 3.22 (dd, 1H); 4.80 (m, 1H); 6.73 (s, 1H); 7.11 (s, 1H); 7.15–7.35 (sc, 5H); 7.42 (t, 1H); 7.65 (s, 1H); 7.86 (dd, 1H); 8.81 (d, 1H).

Example 17

N-[4-Oxo-2-(1H-5-tetrazolyl)-4H-1-benzopyran-8-yl]-1-(4-phenylbutyl)-3-methylindole-5-carboxamide 17A Methyl indole-5-carboxylate Following the process described in example 13 (point A), starting from indole-5-carboxylic acid, the title compound was prepared (92% yield).

$^1$H N.M.R. (300 MHz, CDCl$_3$) δ ppm: 3.98 (s, 3H); 6.64 (t, 1H); 7.26 (t, 1H); 7.40 (d, 1H); 7.91 (dd, 1H); 8.43 (s, 1H); 8.53 (broad s, 1H).

17B Methyl 3-Formylindole-5-carboxylate

Following the process described in example 1 (point E), starting from methyl indole-5-carboxylate, the title compound was prepared (90% yield).

$^1$H N.M.R. (300 MHz, DMSO) δ ppm: 3.90 (s, 3H); 6.63 (d, 1H); 7.90 (d, 1H); 8.45 (s, 1H); 8.80 (s, 1H); 10.00 (s, 1H); 12.46 (broad s, 1H).

17C Methyl 1-(4-phenylbutyl)-3-formylindole-5-carboxylate

A solution of methyl 3-formylindole-5-carboxylate (2.234 g, 11.0 mmol) and potassium tert-butoxide (1.259 g, 11.2 mmol) in dry N,N-dimethylformamide (50 ml) was added with 1-bromo-4-phenylbutane (2.385 g, 11.2 mmol) and left under stirring at room temperature for 18 h. After that the solvent was evaporated off under reduced pressure, the resulting residue was partitioned between a NaCl saturated solution (50 ml) and chloroform (50 ml) and the aqueous phase was extracted with chloroform (3×50 ml). After drying and evaporating off the solvent under reduced pressure, a crude was obtained which was purified by chromatography through a silica gel column, eluting with n-hexane:ethyl acetate, 70:30, thereby obtaining 2.847 g of the title compound (87% yield).

$^1$H N.M.R. (300 MHz, CDCl$_3$) δ ppm: 1.66 (m, 2H); 1.91 (m, 2H); 2.64 (t, 2H); 3.93 (s, 3H); 4.16 (t, 2H); 7.11 (d, 2H); 7.19 (m, 1H); 7.25 (d, 2H); 7.33 (d, 1H); 7.70 (s, 1H); 8.01 (dd, 1H); 8.99 (s, 1H); 9.98 (s, 1H).

17D Methyl 1-(4-phenylbutyl)-3-methylindole-5-carboxylate

A solution of methyl 1-(4-phenylbutyl)-3-formylindole-5-carboxylate (600 mg, 1.79 mmol) in dry dichloromethane (15 ml) was added successively zinc iodide (857 mg, 2.69 mmol) and sodium cyanoborohydride (843 mg, 13.41 mmol). The resulting mixture was left under stirring at 85° C. for 1.5 h. After that the mixture was filtered through celite, washing the solid with dichloromethane (200 ml). The solvent was evaporated off under reduced pressure and the resulting crude was purified by chromatography through a silica gel column, eluting with n-hexane:ethyl acetate, 98:2, thereby recovering 459 mg of the title compound (80% yield).

$^1$H N.M.R. (300 MHz, CDCl$_3$) δ ppm: 1.59 (m, 2H); 1.80 (m, 2H); 2.32 (s, 3H); 2.58 (t, 2H); 3.91 (s, 3H); 4.00 (t, 2H); 6.84 (s, 1H); 7.08 (d, 2H); 7.17 (m, 1H); 7.20–7.27 (m, 3H); 7.87 (dd, 1H); 8.34 (d, 1H).

17E 1-(4-Phenybutyl)-3-methylindole-5-carboxylic acid

Following the process described in example 6 (point E), starting from methyl 1-(4-phenylbutyl)-3-methylindole-5-carboxylate, the title compound was prepared (quantitative yield).

$^1$H N.M.R. (300 MHz, CDCl$_3$) δ ppm: 1.60 (m, 2H); 1.80 (m, 2H); 2.34 (s, 3H); 2.59 (t, 2H); 4.02 (t, 2H); 6.86 (s, 1H); 7.10 (d, 2H); 7.18 (d, 1H); 7.22–7.26 (m, 3H); 7.97 (dd, 1H); 8.45 (d, 1H).

17F N-[4-Oxo-2-(1H-5-tetrazolyl)-4H-1-benzopyran-8-yl]-1-(4-phenylbutyl)-3-methylindole-5-carboxamide Following the process described in example 1 (point K), starting from 1-(4-phenylbutyl)-3-methylindole-5-carboxylic acid and 8-amino-4-oxo-2-(5-1H-tetrazolyl)-4H-1-benzopyran, the title compound was prepared as a yellow solid with melting point 186°–187° C., which was purified by crystallization in methanol (54% yield).

$^1$H N.M.R. (300 MHz, CDCl$_3$) δ ppm: 1.53 (m, 2H); 1.78 (m, 2H); 2.35 (s, 3H); 2.59 (t, 2H); 4.21 (t, 2H); 7.13–7.18 (sc, 4H); 7.23–7.29 (sc, 3H); 7.57 (m, 2H); 7.83 (dd, 1H); 8.87 (dd, 1H); 8.33 (s, 1H); 8.38 (d, 1H); 10.05 (s, 1H).

Example 18

8-[[4-(4-Phenylbutoxy)phenyl]methyloxy]-4-oxo-4H-1-benzopyran-2-carbolic acid

18A Methyl 4-(4-phenylbutoxy)benzoate

A mixture of methyl 4-hydroxybenzoate (3 g, 19.7 mmol), 4-phenylbutanol (3.04 ml, 19.7 mmol) and triphenylphosphine (7.74 g, 29.6 mmol) in anhydrous tetrahydrofuran (110 ml) was added with diethyl azodicarboxylate (4.65 ml, 29.6 mmol). The resulting mixture was left under stirring at room temperature for 36 h, then was added with ethyl ether (500 ml) and left to crystallize for 24 hours at 0° C. After that the solid was filtered and the filtrate was washed successively with 0.2M hydrochloric acid, 5% sodium bicarbonate and a sodium chloride saturated solution. After drying and removing the solvent under reduced pressure, a residue was obtained which was purified by chromatography through a silica gel column, eluting with petroleum ether:chloroform mixtures of increasing polarity, thereby recovering 3.856 g of the title compound (70% yield).

$^1$H N.M.R. (300 MHz, CDCl$_3$) δ ppm: 1.82 (m, 4H); 2.69 (t, 2H); 3.87 (s, 3H); 4.00 (t, 2H); 6.88 (d, 2H); 7.18–7.31 (sc, 5H); 7.98 (d, 2H).

18B 4-(4-Phenylbutoxy)benzoic acid

Following the process described in example 10 (point B), starting from methyl 4-(4-phenylbutoxy)benzoate, the title compound was prepared which was purified by digestion in ethyl ether (92% yield).

$^1$H N.M.R. (300 MHz, CD$_3$OD) δ ppm: 1.81 (m, 4H); 2.68 (t, 2H); 4.01 (t, 2H); 6.90 (d, 2H); 7.16–7.31 (sc, 5H); 7.97 (d, 2H).

18C 4-(4-Phenylbutoxy)benzyl alcohol

A suspension of lithium aluminium hydride (309 mg, 7.62 mmol) in anhydrous tetrahydrofuran (65 ml) was added under inert atmosphere with a solution of 4-(4-phenylbutoxy)benzoic acid (1.03 g, 3.81 mmol) in 20 ml of dry ethyl ether. The mixture was left under stirring at room temperature for 2 hours, after that was added slowly with a NaCl saturated solution in water (80 ml), the two phases were separated and the aqueous one was extracted with ethyl acetate (3×50 ml). The organic extracts were dried and the solvent was evaporated off to obtain a crude, which was digested with ethyl ether. The digestion extracts were evaporated under reduced pressure to obtain 556 mg of the title compound (57% yield).

$^1$H N.M.R. (300 MHz, CDCl$_3$) δ ppm: 1.79 (m, 4H); 2.65 (t, 2H); 3.92 (t, 2H); 4.54 (s, 2H); 6.85 (d, 2H); 7.13–7.28 (sc, 7H).

18D 4-(4-Phenylbutoxy)benzyl chloride

A solution of 4-(4-phenylbutoxy)benzyl alcohol (556 mg, 2.17 mmol) in chloroform (10 ml) was added with thionyl chloride (0.288 ml) and left under stirring at room temperature for 24 h, then evaporated to dryness under reduced pressure to obtain 595 mg of the title compound (quantitative yield).

$^1$H N.M.R. (300 MHz, CDCl$_3$) δ ppm: 1.76 (m, 4H); 2.64 (t, 2H); 3.89 (t, 2H); 4.49 (s, 2H); 6.81 (d, 2H); 7.13–7.28 (sc, 7H).

18E 2-(2,3-Dimethoxyphenyl)ethan-2-ol

A solution of 2,3-dimethoxybenzaldehyde (10.0 g, 60.2 mmol) in dry ethyl ether (100 ml) was added at 0° C. with a 3M solution of methylmagnesium bromide in ethyl ether (35 ml) and left under stirring at 0° C. for 0.5 h. Afterwards the reaction mixture was added with a diphasic mixture of ethyl ether and an ammonium chloride saturated solution, extracting the aqueous phase with ethyl ether. The organic extracts were dried and the solvent was evaporated off under reduced pressure, thereby obtaining 10.06 g of the title compound (92% yield).

¹H N.M.R. (300 MHz, CDCl₃) δ ppm: 1.45 (d, 3H); 3.02 (broad s, 1H); 3.83 (s, 3H); 3.84 (s, 3H); 5.12 (m, 1H); 6.81 (dd, 1H); 6.96–7.06 (sc, 2H).

18F 2',3'-Dimethoxyacetophenone

A solution of potassium dichromate (24.76 g), water (124 ml) and concentrated sulfuric acid (12 ml) was added with 2-(2,3-dimethoxyphenyl)ethan-2-ol (10.06 g, 55.3 mmol) and left under stirring at room temperature for 15 min. After that the mixture was extracted with ethyl ether and washed successively with a 5% potassium carbonate solution (2×150 ml) and with a sodium chloride saturated solution (1×100 ml). The solvent was dried and evaporated under reduced pressure to obtain a residue which was purified by distillation under high vacuum. At a pressure of 0.3 torr and at a temperature of 85° C., 6.47 g of the title compound distiled (65% yield).

¹H N.M.R. (300 MHz, CDCl₃) δ ppm: 2.62 (s, 3H); 3.88 (s, 3H); 3.90 (s, 3H); 7.05–7.10 (sc, 2H); 7.21 (dd, 1H).

18G 2',3'-Dihydroxyacetophenone

A solution of 2',3'-dimethoxyacetophenone (4.85 g, 26.9 mmol) in dichloromethane (100 ml) was added at −70° C. with a 1M boron tribromide solution in dichloromethane (68 ml). The mixture was left to cool, keeping stirring for 2.5 hours at room temperature, then added with methanol (70 ml), left under stirring for 1 h, thereafter evaporated to dryness. The residue was dissolved in ethyl acetate (250 ml), washed with 2% NaHCO₃ (1×30 ml), dried and the solvent was evaporated off, to obtain a crude which was purified by crystallization in methanol, thereby obtaining 3.10 g of the title compound as a yellow solid (76% yield).

¹H N.M.R. (300 MHz, CDCl₃) δ ppm: 2.61 (s, 3H); 7.05–6.77 (t, 1H); 7.02 (dd, 1H); 7.36 (dd, 1H).

18H Ethyl 8-hydroxy-4-oxo-4H-1-benzopyran-2-carboxylate

Following the process described in example 1 (point A), starting from 2',3'-dihydroxyacetophenone, the title compound was prepared (83% yield).

¹H N.M.R. (300 MHz, CDCl₃) δ ppm: 1.47 (t, 3H); 4.52 (q, 2H); 7.10 (s, 1H); 7.30 (m, 2H); 7.61 (dd, 1H).

18I Ethyl 8-[[4-(4-phenylbutoxy)phenyl]methyloxy]-4-oxo-4H-1-benzopyran-2-carboxylate A solution of potassium carbonate (330 mg, 2.39 mmol) in dry N,N-dimethylformamide (15 ml) was added with ethyl 8-hydroxy-4-oxo-4H-1-benzopyran-2-carboxylate (520 mg, 2.39 mmol) stirring at room temperature for 10 min. After that the reaction mixture was added with 4-(4-phenylbutoxy)benzyl chloride 595 mg, 2.17 mmol) and left under stirring at 60° C. for 18 h, subsequently was added with water (25 ml), extracted with ethyl ether (3×50 ml), dried and the solvent was evaporated off under reduced pressure, to obtain a residue which was purified by chromatography through a silica gel column, eluting with petroleum ether:chloroform, 7:3, recovering 740 mg of the title compound (66% yield).

¹H N.M.R. (300 MHz, CDCl₃) δ ppm: 1.40 (t, 3H); 1.80 (m, 4H); 2.66 (t, 2H); 3.95 (t, 2H); 4.41 (q, 2H); 5.16 (s, 2H); 6.89 (d, 2H); 7.09 (s, 1H); 7.16–7.29 (sc, 7H); 7.40 (d, 2H); 7.71 (dd, 1H).

18J 8-[[4-(4-Phenylbutoxy)phenyl]methyloxy]-4-oxo-4H-1-benzopyran-2-carboxylic acid Following the process described in example 1 (point M), starting from ethyl 8-[[4-(4-phenylbutoxy)phenyl] methyloxy]-4-oxo-4H-1-benzopyran-2-carboxylate, the title compound was prepared as a slightly yellowish semisolid (78% yield).

¹H N.M.R. (300 MHz, CD₃OD) δ ppm: 1.78 (m, 4H); 2.66 (broad t, 2H); 3.95 (broad t, 2H); 5.20 (s, 2H); 6.87 (d, 2H); 7.10 (s, 1H); 7.14–7.34 (sc, 7H); 7.40 (d, 2H); 7.69 (dd, 1H).

Example 19

8-[[4-(4-Phenylbutoxy)phenyl]sulfonylamino]-4-oxo-4H-1-benzopyran-2-carboxylic acid

19A N-(3-Acetyl-2-hydroxyphenyl)-4-methoxybenzenesulfonamide

A solution of 3'-amino-2'-hydroxyacetophenone hydrobromide (1.282 g, 5.52 mmol) in pyridine (25 ml) was added at 0° C. with 4-methoxybenzenesulfonyl chloride (1.18 g, 5.71 mmol) dissolved in the minimum amount of pyridine and the mixture was left at room temperature for 18 h. Afterwards it was evaporated to dryness, redissolved in dichloromethane, washed with 1M HCl, dried and the solvent was evaporated off under reduced pressure, thereby obtaining 1.479 g of the title compound (81% yield).

¹H N.M.R. (300 MHz, CDCl₃) δ ppm: 2.58 (s, 3H); 3.80 (s, 3H); 6.85 (d, 2H); 6.86 (t, 1H); 7.11 (s, 1H); 7.45 (d, 1H); 7.72 (d, 2H); 7.77 (d, 1H); 12.59 (s, 1H).

19B Ethyl 8-(4-methoxyphenyl)sulfonylamino]-4-oxo-4H-1-benzopyran-2-carboxylate Following the process described in example 1 (point A), starting from N-(3-acetyl-2-hydroxyphenyl)-4-methoxybenzenesulfonamide and diethyl oxalate, the title compound was prepared, which was purified by chromatography through a silica gel column, eluting with petroleum ether:chloroform 4:6 (90% yield).

¹H N.M.R. (300 MHz, CDCl₃) δ ppm: 1.43 (t, 3H); 3.74 (s, 3H); 4.45 (q, 2H); 6.77 (d, 2H); 6.99 (s, 1H); 7.34 (dd, 1H); 7.71 (d, 2H); 7.80 (dd, 1H); 7.88 (d, 1H); 8.66 (s, 1H).

19C Ethyl 8-[(4-hydroxyphenyl)sulfonylamino)]-4-oxo-4H-1-benzopyran -2-carboxylate Following the process described in example 18 (point G), starting from ethyl 8-(4-methoxyphenyl)sulfonylamino]-4-oxo-4H-1-benzopyran-2-carboxylate, the title compound was prepared, which was purified by chromatography through a silica gel column, eluting with petroleum ether:chloroform, 25:75 (67% yield).

¹H N.M.R. (300 MHz, CDCl₃) δ ppm: 1.43 (t, 3H); 4.47 (q, 2H); 6.80 (d, 2H); 6.99 (s, 1H); 7.24 (s, 1H); 7.38 (t, 1H); 7.61 (d, 2H); 7.85 (d, 1H); 7.96 (d, 1H); 12.51 (s, 1H).

19D 8-[[4-(4-Phenylbutoxy)phenyl]sulfonylamino]-4-oxo-4H-1-benzopyran-2-carboxylic acid A solution of ethyl 8-[(4-hydroxyphenyl) sulfonylamino)]-4-oxo-4H-1-benzopyran-2-carboxylate (200 mg, 0.26 mmol) in DMF (3 ml) was added with a 5.3M sodium methoxide solution in methanol (0.194 ml, 1.04 mmol) and the mixture was left under stirring at 50° C. for 2 h, then was cooled at 0° C., added with 1-bromo-4-phenylbutane (57 mg, 0.26 mmol), stirring at 50° C. for 2 h. and at room temperature for 18 h. Subsequently the mixture was evaporated to dryness, partitioned in a mixture of water:ethyl acetate, 1:1, extracted with ethyl acetate (3×25 ml), washed with 0.2M HCl, dried and the solvent was evaporated off, to obtain a crude which was purified by chromatography through a silica gel column, eluting with mixtures of chloroform:methanol mixtures of increasing polarity, thereby obtaining 70 mg of the title product (54% yield).

¹H N.M.R. (300 MHz, CD₃OD—CDCl₃ mixtures) δ ppm: 1.76 (m, 4H); 2.65 (broad t, 2H); 3.95 (broad t, 2H); 6.83 (d, 2H); 6.99 (s, 1H); 7.14–725 (sc, 5H); 7.42 (t, 1H); 7.68 (d, 2H); 7.87 (d, 1H); 7.97 (d, 1H).

Example 20

4-Oxo-8-[(E)-2-[4-(4-phenylbutoxy)-phenyl]ethen-1-yl]-4H-1-benzopyran-2-carboxylic acid

20A 2'-Hydroxy-3'-iodoacetophenone

A suspension of 3'-amino-2'-hydroxyacetophenone hydrobromide (2.5 g, 10.8 mmol) in water (10 ml) at 0° C. was added successively with concentrated sulfuric acid (0.70 ml) and sodium nitrite (0.783 g, 11.3 mmol) dissolved in water (1.5 ml) and the mixture was left under stirring at 0° C. for 20 min. After that, concentrated sulfuric acid (0.2 ml) was added and the resulting mixture was poured onto a solution of potassium iodide (2.2 g) in water (2 ml) cooled at 0° C. Copper powder (11 mg) was added in a few minutes and the mixture was left at 75° C. for 2 h. After this time the mixture was left to cool at room temperature, then extracted with chloroform (3×50 ml), the organic phase was washed with a 5% sodium thiosulfate solution, dried and the solvent was evaporated off under reduced pressure. The resulting residue was purified by column chromatography eluting with petroleum ether:chloroform, 6:4, thereby recovering 1.95 g of title compound (69% yield).

¹H N.M.R. (300 MHz, CDCl₃) δ ppm: 2.64 (s, 3H); 6.69 (t, 1H); 7.71 (d, 1H); 7.90 (d, 1H), 13.15 (s, 1H).

20B 4-(4-Phenylbutoxy)benzaldehyde

Following the process described in example 18 (point A), starting from 4-hydroxybenzaldehyde and 4-phenyl-1-butanol, the title compound was prepared (63% yield).

¹H N.M.R. (300 MHz, CDCl₃) δ ppm: 1.80 (m, 4H); 2.66 (t, 2H); 4.00 (t, 2H); 6.93 (d, 2H); 7.16 (sc, 5H); 7.78 (d, 2H); 9.83 (s, 1H).

20C 4-(4-Phenylbutoxy)styrene

A solution of methyltriphenylphosphonium bromide (4.98 g, 13.9 mmol) in anhydrous tetrahydrofuran (130 ml) at 0° C. and under inert atmosphere was added with a 1.6M butyl lithium solution in hexane (8.69 ml) and the mixture was left under stirring at 0° C. for 2 h. After that, a solution of 4-(4-phenylbutoxy)benzaldehyde (2.5 g, 9.84 mmol) in tetrahydrofuran (10 ml) was added and the mixture was left under stirring at room temperature for 36 h, then carefully added with water (20 ml) and extracted with ethyl ether (4×50 ml). The organic extracts were dried and the solvents were evaporated off under reduced pressure. The resulting crude was purified by chromatography through a silica gel column, eluting with petroleum ether:ethyl ether, 95:5, thereby recovering 4.20 g of the title compound (62% yield).

¹H N.M.R. (300 MHz, CDCl₃) δ ppm: 1.78 (m, 4H); 2.67 (broad t, 2H); 3.95 (broad t, 2H); 5.10 (d, 1H); 5,58 (d, 1H); 6.64 (dd, 1H); 6.82 (d, 2H); 7.17–7.33 (sc, 7H).

20D 3'-[(E)-2-[4-(4-Phenylbutoxy)phenyl]ethen-1-yl]-2'-hydroxyacetophenone

A mixture of 4-(4-phenylbutoxy)styrene (742 mg, 2.92 mmol), 2'-hydroxy-3'-iodoacetophenone (612 mg, 2.33 mmol), triethylamine (0.408 ml, 3.01 mmol), palladium (II) acetate (14 mg, 0.06 mmol) in acetonitrile (15 ml) was left under stirring at 100° C. for 24 h. Then the mixture was added with water (15 ml), extracted with ethyl ether (4×30 ml), dried and the solvents were evaporated off under reduced pressure. The resulting residue was purified by chromatography through a silica gel column, eluting with petroleum ether:ethyl ether, 9:1, recovering 633 g of the title compound (70% yield).

¹H N.M.R. (300 MHz, CDCl₃) δ ppm: 1.79 (m, 4H); 2.62 (s, 3H); 2.68 (broad t, 2H); 3.95 (broad t, 2H); 6.85 (d, 2H); 6.86 (t, 1H); 7.08–7.36 (sc, 7H); 7.45 (d, 2H); 7.59 (dd, 1H); 7.73 (dd, 1H), 12.51 (s, 1H).

20E Ethyl 4-oxo-8-[(E)-2-[4-(4-phenylbutoxy)phenyl]-ethen-1-yl]-4H-1-benzopyran-2-carboxylate Following the process described in example 1 (point A), starting from 3'-[(E)-2-[4-(4-phenylbutoxy)phenyl]-ethen-1-yl]-2'-hydroxyacetophenone and diethyl oxalate, the title compound was prepared, which was purified by chromatography through a silica gel column, eluting with petroleum ether:chloroform, 6:4 (66% yield).

¹H N.M.R. (300 MHz, CDCl₃) δ ppm: 1.41 (t, 3H); 1.80 (m, 4H); 2.67 (broad t, 2H); 3.95 (broad t, 2H); 4.39 (q, 2H); 6.85 (d, 2H); 7.03 (s, 1H); 7.17–7.32 (sc, 8H); 7.44 (d, 2H); 7.77 (d, 1H); 7.93 (dd, 1H).

20F 4-oxo-8-[(E)-2-[4-(4-phenylbutoxy)phenyl]ethen-1-yl]-4H-1-benzopyran-2-carboxylic acid Following the process described in example 1 (point M), starting from ethyl 4-oxo-8-[(E)-2-[4-(4-phenylbutoxy)phenyl]ethen-1-yl]-4H-1-benzopyran-2-carboxylic, the title compound was prepared as a yellow solid with melting point 159–161° C. (78% yield).

¹H N.M.R. (300 MHz, DMSO) δ ppm: 1.74 (broad m, 4H); 2.65 (broad t, 2H); 4.03 (broad t, 2H); 6.94 (s, 1H); 6.99 (d, 2H); 7.17–7.32 (sc, 5H); 7.40 (d, 1H); 7.52 (t, 1H); 7.54 (d, 2H); 7.67 (d, 1H); 7.92 (dd, 1H); 8.13 (dd, 1H).

Example 21

8-[(E)-2-[4-(4-Phenylbutoxy)phenyl]ethen-1-yl]-4-oxo-2-(5-1H-tetrazolyl]-4H-1-benzopyran

21A 8-[(E)-2-[4-(4-Phenylbutoxy)phenyl]ethen-1-yl]-4-oxo-4H-1-benzopyran-2-carboxamide Following the process described in example 12 (point A), by aminolysis reaction of ethyl 8-[(E)-2-[4-(4-phenylbutoxy)phenyl]ethen-1-yl]-4-oxo-4H-1-benzopyran-2-carboxylate, the title compound was prepared as a yellow solid (83% yield).

¹H N.M.R. (300 MHz, DMSO) δ ppm: 1.73 (broad m, 4H); 2.65 (broad t, 2H); 4.03 (broad t, 2H); 6.91 (s, 1H); 6.99 (d, 2H); 7.17–7.32 (sc, 5H); 7.49 (d, 1H); 7.51 (t, 1H); 7.70 (d, 2H); 7.72 (d, 1H); 7.93 (d, 1H); 8.21 (d, 1H); 8.28 (broad s, 1H); 8.53 (broad s, 1H).

21B 8-[(E)-2-[4-(4-Phenylbutoxy)phenyl]ethen-1-yl]-4-oxo-4H-1-benzopyran-2-carbonitrile Following the process described in example 2 (point D), by reacting 8-[(E)-2-[4-(4-phenylbutoxy)phenyl]-ethen-1-yl]-4-oxo-4H-1-benzopyran-2-carboxamide with phosphorous oxychloride in DMF for 0.5 h at 0° C., the title compound was prepared (97% yield).

¹H N.M.R. (300 MHz, CDCl₃) δ ppm; 1.80 (broad m, 4H); 2.67 (broad t, 2H); 3.93 (broad t, 2H); 6.70 (s, 1H); 6.85

(d, 2H); 7.08–7.30 (sc, 7H); 7.38 (t, 1H); 7.43 (d, 2H); 7.91 (d, 1H); 7.98 (d, 1H).

21C 8-[(E)-2-[4-(4-Phenylbutoxy)phenyl]ethen-1-yl]-2-4-oxo-(5-1H-tetrazolyl]-4H-1-benzopyran Following the process described in example 7 (point C), starting from 8-[(E)-2-[4-(4-phenylbutoxy)phenyl]-ethen-1-yl]-4-oxo-4H-1-benzopyran-2-carbonitrile, the title compound was prepared as a yellow solid with melting point 191.4–192.1° C., which was purified by digestion with methanol (95% yield).

$^1$H N.M.R. (300 MHz, DMSO) δ ppm: 1.74 (broad m, 4H); 2.66 (broad t, 2H); 4.03 (broad t, 2H); 7.01 (d, 2H); 7.12 (s, 1H); 7.18–7.32 (sc, 5H); 7.53 (t, 1H); 7.61 (s, 2H); 7.65 (d, 2H); 7.95 (dd, 1H); 8.19 (dd, 1H).

Example 22

8-[(E)-2-[4-[4-(4-Fluorophenyl)-butoxy]phenyl]ethen-1-yl]-4-oxo-4H-1-benzopyran-2-carboxylic acid

22A 4-(4-Fluorophenyl)-1-butanol

A suspension of aluminium trichloride (10.2 g, 76.5 mmol) in dichloromethane (250 ml) at 0° C. was added with the borane-tert-butylamine complex (13.2 g, 153 mmol) and the mixture was left under stirring at 0° C. for 15 minutes. After that the mixture was added with 3-(4-fluorobenzoyl) propionic acid (5 g, 25.5 mmol) stirring at room temperature for 20 h, then added slowly with 0.2M HCl (75 ml) and extracted with ethyl acetate (3×100 ml). The combined organic phases were washed with 0.2M HCl and with a NaCl saturated solution, dried and the solvents were removed under reduced pressure. The resulting residue was purified by chromatography through a silica gel column, eluting with hexane:ethyl acetate, 8:2, thereby recovering 2.70 g of the title product as a colourless oil (63% yield).

$^1$H N.M.R. (300 MHz, CDCl$_3$) δ ppm: 1.59 (m, 4H); 2.58 (t, 2H); 3.60 (t, 2H); 6.90–7.12 (m, 5H).

22B 4-[4-(4-Fluorophenyl)butoxy]benzaldehyde

Following the process described in example 18 (point A), starting from 4-hydroxybenzaldehyde and 4-(4-fluorophenyl)-1-butanol, the title compound was prepared (43% yield).

$^1$H N.M.R. (300 MHz, CDCl$_3$) δ ppm: 1.80 (m, 4H); 2.65 (t, 2H); 4.03 (t, 2H); 6.95 (m, 3H); 7.12 (m, 2H); 7.81 (d, 2H); 9.85 (s, 1H).

22C 4-[4-(4-Fluorophenyl)butoxy]styrene

Following the process described in example 20 (point C), starting from 4-[4-(4-fluorophenyl)butoxy]benzaldehyde, the title compound was prepared, which was purified chromatographically through a silica gel column, eluting with petroleum ether:ethyl ether, 98:2 (58% yield).

$^1$H N.M.R. (300 MHz, CDCl$_3$) δ ppm: 1.75 (m, 4H); 2.56 (t, 2H); 3.87 (t, 2H); 5.06 (dd, 1H); 5.56 (dd, 1H); 6.60 (m, 1H); 6.79 (m, 2H); 6.91 (m, 2H); 7.05 (m, 2H); 7.26 (m, 2H).

22D 3'-[(E)-2-[4-[4-(4-Fluorophenyl)butoxy]phenyl]ethen-1-yl]-2'-hydroxyacetophenone Following the process described in example 20 (point D), starting from 4-[4-(4-fluorophenyl)butoxy]-styrene and 2'-hydroxy-3'-iodoacetophenone, the title compound was prepared, which was purified by chromatography through a silica gel column, eluting with petroleum ether:ethyl ether, 95:5 (70% yield).

$^1$H N.M.R. (300 MHz, CDCl$_3$) δ ppm: 1.78 (m, 4H); 2.63 (t, 2H); 3.95 (t, 2H); 6.84–6.99 (sc, 5H); 7.14 (m, 3H); 7.34 (d, 1H); 7.45 (d, 2H); 7.62 (d, 1H); 7.75 (d, 1H), 12.55 (s, 1H).

22E Ethyl 8-[(E)-2-[4-[4-(4-fluorophenyl)butoxy]phenyl]-ethen-1-yl]-4-oxo-4H-1-benzopyran-2-carboxylate Following the process described in example 1 (point A), starting from 3'-[(E)-2-[4-[4-(4-fluorophenyl)butoxy]phenyl]ethen-1-yl]-2'-hydroxy-acetophenone and diethyl oxalate, the title compound was prepared, which was purified by chromatography through a silica gel column, eluting with petroleum ether:chloroform, 8:2 (65% yield).

$^1$H N.M.R. (300 MHz, CDCl$_3$) δ ppm: 1.42 (t, 3H); 1.79 (m, 4H); 2.65 (broad t, 2H); 3.97 (broad t, 2H); 4.42 (q, 2H); 6.87 (d, 2H); 6.95 (t, 2H); 7.05 (s, 1H); 7.13 (t, 2H); 7.28 (d, 1H); 7.33 (broad s, 2H); 7.46 (d, 2H); 7.81(d, 1H); 7.97 (d, 1H).

22F 8-[(E)-2-[4-[4-(4-Fluorophenyl)butoxy]phenyl]-ethen-1-yl]-4-oxo-4H-1-benzopyran-2-carboxylic acid Following the process described in example 1 (point M), starting from ethyl 8-[(E)-2-[4-[4-(4-fluorophenyl)butoxy]phenyl]ethen-1-yl]-4-oxo-4H-1-benzopyran-2-carboxylate, the title compound was prepared as a yellow solid with melting point 161–162° C., which was purified by crystallization in methanol (71% yield).

$^1$H N.M.R. (300 MHz, DMSO) δ ppm: 1.73 (m, 4H); 2.65 (broad t, 2H); 4.04 (broad t, 2H); 6.96 (s, 1H); 7.01 (d, 2H); 7.11 (t, 2H); 7.27 (t, 2H); 7.43 (d, 1H); 7.53 (m, 3H); 7.68 (d, 1H); 7.94 (d, 1H); 8.15 (d, 1H).

Example 23

8-[(E)-2-[4-[4-(4-Fluorophenyl)butoxy]phenyl]ethen-1-yl]-4-oxo-2-(5-1H-tetrazolyl)-4H-1-benzopyran

23A 8-[(E)-2-[4-[4-(4-Fluorophenyl)butoxy]phenyl]ethen-1-yl]4-oxo-4H-1-benzopyran-2-carboxamide Following the process described in example 12 (point A), by aminolysis reaction of ethyl 8-[(E)-2-[4-[4-(4-fluorophenyl)butoxy]phenyl]ethen-1-yl]-4-oxo-4H-1-benzopyran-2-carboxylate, the title compound was prepared as a yellow solid (93% yield).

$^1$H N.M.R. (300 MHz, DMSO) δ ppm: 1.75 (broad m, 4H); 2.67 (broad t, 2H); 4.06 (broad t, 2H); 6.93 (s, 1H); 7.01 (d, 2H); 7.13 (t, 2H); 7.29 (t, 2H); 7.50 (d, 1H); 7.56 (t, 1H); 7.71 (d, 2H); 7.76 (d, 1H); 7.98 (dd, 1H); 8.25 (dd, 1H); 8.28 (broad s, 1H); 8.55 (broad s, 1H).

23B 8-[(E)-2-[4-[4-(4-Fluorophenyl)butoxy]phenyl]ethen-1-yl]-4-oxo-4H-1-benzopyran-2-carbonitrile Following the process described in example 2 (point D), reacting 8-[(E)-2-[4-[4-(4-fluorophenyl)butoxy]phenyl]ethen-1-yl]-4-oxo-4H-1-benzopyran-2-carboxamide with phosphorous oxychloride in DMF for 0.5 h at 0° C., the title compound was prepared (95% yield).

$^1$H N.M.R. (300 MHz, CDCl$_3$) δ ppm: 1.82 (broad m, 4H); 2.68 (broad t, 2H); 4.01 (broad t, 2H); 6.81 (s, 1H); 6.90–7.52 (sc, 11H); 8.02 (t, 2H).

23C 8-[(E)-2-[4-[4-(4-Fluorophenyl)butoxy]phenyl]-ethen-1-yl]-4-oxo-2-(5-1H-tetrazolyl)-4H-1-benzopyran Following the process described in example 7 (point C), starting from 8-[(E)-2-[4-[4-(4-fluorophenyl)butoxy]phenyl]ethen-1-yl]-4-oxo-4H-1-benzopyran-2-carbonitrile, the title compound was prepared as a yellow solid with melting point 173.6–174.7° C., which was purified by crystallization in methanol (83% yield).

$^1$H N.M.R. (300 MHz, DMSO) δ ppm: 1.74 (broad m, 4H); 2.66 (broad t, 2H); 4.04 (broad t, 2H); 7.01 (d, 2H); 7.13 (m, 3H); 7.27 (m, 2H); 7.53 (t, 1H); 7.61 (s, 2H); 7.65 (d, 2H); 7.95 (dd, 1H); 8.19 (dd, 1H).

Example 24

8-[(E)-2-[4-(4-Phenylbutoxy)-2-fluorophenyl]ethen-1-yl]-4-oxo-4H-1-benzopyran-2-carboxylic acid

24A 2-Fluoro-4-hydroxybenzoic acid

Following the process described in example 5 (point G), starting from 2-fluoro-2-hydroxybenzonitrile, the title compound was prepared (quantitative yield).

$^1$H.M.R. (300 MHz, CD$_3$OD) δ ppm: 6.61 (dd, 1H); 6.69 (dd, 1H); 7.87 (t, 1H), 12.51 (s, 1H).

24B Methyl 2-fluoro-4-hydroxybenzoate

Following the process described in example 5 (point C), starting from 2-fluoro-4-hydroxybenzoic acid, the title compound was prepared (86% yield).

$^1$H. M.R. (300 MHz, CD$_3$OD) δ ppm: 3.83 (s, 3H); 6.55 (dd, 1H); 6.65 (dd, 1H); 7.80 (t, 1H), 12.35 (s, 1H).

24C Methyl 4-(4-phenylbutoxy)-2-fluorobenzoate

Following the process described in example 18 (point A), starting from methyl 2-fluoro-4-hydroxybenzoate and 4-phenyl-1-butanol, the title compound was prepared, which was purified by chromatography through a silica gel column, eluting with hexane:ethyl acetate, 95:5 (97% yield).

$^1$H .M.R. (300 MHz, CDCl$_3$) δ ppm: 1.80 (m, 4H); 2.67 (t, 2H); 3.87 (s, 3H); 3.96 (t, 2H); 6.58 (dd, 1H); 6.67 (dd, 1H); 7.17–7.23 (m, 5H); 7.87 (t, 1H).

24D 4-(4-Phenylbutoxy)-2-fluorobenzyl alcohol

Following the process described in example 1 (point C), starting from methyl 4-(4-phenylbutoxy)-2-fluorobenzoate, the title compound was prepared (quantitative yield). $^1$H .M.R. (300 MHz, CD$_3$OD) δ ppm: 1.69 (m, 4H); 2.57 (t, 2H); 3.81 (t, 2H); 4.59 (s, 2H); 6.57 (dd, 1H); 6.64 (dd, 1H); 7.09–7.24 (m, 5H); 7.28 (t, 1H).

24E 4-(4-Phenylbutoxy)-2-fluorobenzaldehyde

A solution of 4-(4-phenylbutoxy)-2-fluorobenzyl alcohol (1.38 g, 5.03 mmol) in dichloromethane (50 ml) was added with pyridinium chlorochromate (1.63 g, 7.54 mmol), stirring at room temperature for 1 h. After that the reaction mixture was filtered on celite, washing with dichloromethane. After drying and removing the solvent, the resulting crude was purified by chromatography through a silica gel column, eluting with dichloromethane, thereby recovering 1.02 g of the title compound (74% yield).

$^1$H .M.R. (300 MHz, CDCl$_3$) δ ppm: 1.83 (m, 4H); 2.69 (t, 2H); 4.01 (t, 2H); 6.57 (dd, 1H); 6.73 (dd, 1H); 7.17–7.31 (m, 5H); 7.79 (t, 1H); 10.18 (s, 1H).

24F 4-(4-Phenylbutoxy-2-fluoro styrene

Following the process described in example 20 (point C), starting from 4-(4-phenylbutoxy)-2-fluorobenzaldehyde and methyl triphenyl phosphonium salt, the title compound was prepared, which was purified by chromatography through a silica gel column, eluting with hexane:ethyl acetate, 1:1 (65% yield).

$^1$H N.M.R. (300 MHz, CDCl$_3$) δ ppm: 1.78 (m, 4H); 2.66 (t, 2H); 3.90 (t, 2H); 5.21 (dd, 1H); 5.65 (dd, 1H); 6.55 (dd, 1H); 6.62 (dd, 1H); 6.78 (dd, 1H); 7.17–7.31 (m, 5H); 7.35 (t, 1H).

24G 3'-[(E)-2-[4-(4-Phenylbutoxy)-2-fluorophenyl]ethen-1-yl]-2'-hydroxyacetophenone Following the process described in example 20 (point D), starting from 4-(4-phenylbutoxy)-2-fluorostyrene and 2'-hydroxy-3'-iodoacetophenone, the title compound was prepared, which was purified by flash chromatography through a column, eluting with petroleum ether:ethyl acetate, 95:5 (67% yield).

$^1$H N.M.R. (300 MHz, CDCl$_3$) δ ppm: 1.78 (m, 4H); 2.59 (s, 3H); 2.66 (t, 2H); 3.91 (t, 2H); 6.56 (dd, 1H); 6.64 (dd, 1H); 6.86 (t, 1H); 7.17–7.30 (m, 6H); 7.40 (d, 1H); 7.53 (t, 1H); 7.59 (dd, 1H); 7.74 (dd, 1H), 12.88 (s, 1H).

24H Ethyl 8-[(E)-2-[4-(4-phenylbutoxy)-2-fluorophenyl]-ethen-1-yl]-4-oxo-4H-1-benzopyran-2-carboxylate Following the process described in example 1 (point A), starting from 3'-[(E)-2-[4-(4-phenylbutoxy)-2-fluorophenyl]ethen-1-yl]-2'-hydroxy-acetophenone and diethyl oxalate, the title compound was prepared (quantitative yield).

$^1$H N.M.R. (300 MHz, CDCl$_3$) δ ppm: 1.40 (t, 3H); 1.79 (m, 4H); 2.66 (t, 2H); 4.40 (q, 2H); 3.91 (t, 2H); 6.57 (dd, 1H); 6.64 (dd, 1H); 7.02 (s, 1H); 7.17–7.32 (m, 6H); 7.37 (d, 2H); 7.46 (t, 1H); 7.78 (d, 1H); 7.95 (d, 1H).

24I 8-[(E)-2-[4-[4-Phenylbutoxy)-2-fluorophenyl]ethen-1-yl]-4-oxo-4H-1-benzopyran-2-carboxylic acid Following the process described in example 1 (point M), starting from ethyl 8-[(E)-2-[4-(4-phenylbutoxy)-2-fluorophenyl]ethen-1-yl]-4-oxo-4H-1-benzopyran-2-carboxylate, the title compound was prepared as a yellow solid with melting point 73.4–73.5° C., which was purified by crystallization in methanol (52% yield).

$^1$H N.M.R. (300 MHz, CDCl$_3$/CD$_3$OD mixtures) δ ppm: 1.81 (broad m, 4H); 2.69 (broad t, 2H); 3.95 (broad t, 2H); 6.60 (d, 1H); 6.69 (d, 1H); 7.17–7.32 (m, 6H); 7.41 (t, 1H); 7.52 (s, 2H); 7.58 (t, 1H); 7.94 (d, 1H); 8.06 (d, 1H).

Example 25

8-[(E)-2-[2-(4'-Fluorobenzyloxymethyl)-2,3-dihydrobenzofuran-5-yl]ethen-1-yl]-4-oxo-4H-1-benzopyran-2-carboxylic acid

25A 2-(4'-Fluorobenzyloxymethyl)-5-hydroxymethyl-2,3-dihydrobenzofuran

Following the process described in example 18 (point C), starting from ethyl 2-(4'-fluorobenzyloxymethyl)-2,3-dihydrobenzofuran-2-carboxylate (7.00 g, 23.2 mmol), LiAlH$_4$ (3.51 g, 92.6 mmol) and dry ethyl ether (300 ml), the title compound was prepared (83% yield).

$^1$H N.M.R. (300 MHz, CDCl$_3$) δ ppm: 2.90 (dd, 1H); 3.08 (broad s, 1H); 3.14 (dd, 1H); 3.55 (dd, 1H); 3.61 (dd, 1H); 4.44 (s, 2H); 4.50 (dd, 2H); 4.90 (m, 1H); 6.70 (d, 1H); 6.98 (m, 3H); 7.08 (s, 1H); 7.26 (m, 2H).

25B 2-(4'-Fluorobenzyloxymethyl)-5-formyl-2,3-dihydrobenzofuran

Following the process described in example 24 (point E), starting from 2-(4'-fluorobenzyloxymethyl)-5-hydroxymethyl-2,3-dihydrobenzofuran, the title compound was prepared (72% yield).

$^1$H N.M.R. (300 MHz, CDCl$_3$) δ ppm: 3.06 (dd, 1H); 3.30 (dd, 1H); 4.56 (d, 2H); 4.44 (s, 2H); 5.09 (m, 1H); 6.89 (d, 1H); 7.01 (t, 2H); 7.27 (m, 2H); 7.67 (d, 1H); 7.71 (s, 1H); 9.82 (s, 1H).

25C 2-(4'-Fluorobenzyloxymethyl)-5-vinil-2,3-dihydrobenzofuran

Following the process described in example 20 (point C), starting from 2-(4'-fluorobenzyloxymethyl)-5-formyl-2,3-dihydrobenzofuran, the title compound was prepared, which was purified by chromatography through a silica gel column, eluting with petroleum ether:ethyl acetate, 95:5 (58% yield).

$^1$H N.M.R. (300 MHz, CDCl$_3$) δ ppm: 2.98 (dd, 1H); 3.21 (dd, 1H); 4.58 (dd, 1H); 4.66 (dd, 1H); 4.52 (d, 1H); 4.56 (d, 1H); 4.95 (m, 1H); 5.06 (d, 1H); 5.55 (d, 1H); 6.62 (dd, 1H); 6.73 (d, 1H); 7.00 (t, 2H); 7.12 (dd, 1H); 7.23–7.29 (m, 3H).

25D 3'-[(E)-2-[2-(4'-Fluorobenzyloxymethyl)-2,3-dihydrobenzofuran-5-yl]ethen-1-yl]-2'-hydroxyacetophenone Following the process described in example 20 (point D), starting from 2-(4'-fluorobenzyloxymethyl)-5-vinil-2,3-dihydrobenzofuran and 2'-hydroxy-3'-iodoacetophenone, the title compound was prepared, which was purified by chromatography through a silica gel column, eluting with petroleum ether:ethyl acetate, 85:15 (63% yield).

$^1$H N.M.R. (300 MHz, CDCl$_3$) δ ppm: 2.58 (s, 3H); 2.96 (dd, 1H); 3.22 (dd, 1H); 3.63 (m, 2H); 4.50 (d, 1H); 4.56 (d, 1H); 4.96 (m, 1H); 6.76 (d, 1H); 6.85 (t, 1H); 6.99 (t, 2H); 7.08 (d, 1H); 7.22–7.32 (m, 4H); 7.37 (s, 1H); 7.57 (d, 1H); 7.70 (d, 1H); 12.88 (s, 1H).

25E Ethyl 8-[(E)-2-[2-(4'-Fluorobenzyloxymethyl)-2,3-dihydrobenzofuran-5-yl]ethen-1-yl]-4-oxo-4H-1-benzopyran-2-carboxylate Following the process described in example 1 (point A), starting from 3'-[(E)-2-[2-(4'-fluorobenzyloxymethyl)-2,3-dihydrobenzofuran-5-yl]ethen-1-yl]-2'-hydroxyacetophenone and diethyl oxalate, the title compound was prepared (quantitative yield).

$^1$H N.M.R. (300 MHz, CDCl$_3$) δ ppm: 1.43 (t, 3H); 3.01 (dd, 1H); 3.26 (dd, 1H); 3.66 (m, 2H); 4.42 (q, 2H); 4.53 (d, 1H); 4.58 (d, 1H); 6.78 (d, 1H); 7.01 (m, 3H); 7.27–7.38 (m, 7H); 7.81 (dd, 1H); 7.96 (d, 1H).

25F 8-[(E)-2-[2-(4'-fluorobenzyloxymethyl)-2,3-dihydrobenzofuran-5-yl]ethen-1-yl]-4-oxo-4H-1-benzopyran-2-carboxylic acid Following the process described in example 1 (point M), starting from ethyl 8-[(E)-2-[2-(4'-fluorobenzyloxymethyl)-2,3-dihydrobenzofuran-5-yl]ethen-1-yl]-4-oxo-4H-1-benzopyran-2-carboxylate, the title compound was prepared as a yellow solid with melting point 203.6–205.4° C., which was purified by digestion with ethyl ether (53% yield).

$^1$H N.M.R. (300 MHz:, CDCl$_3$/CD$_3$OD mixtures) δ ppm: 3.03 (dd, 1H); 3.31 (dd, 1H); 3.69 (m, 2H); 4.55 (d, 1H); 4.60 (d, 1H); 5.02 (m, 1H); 6.79 (d, 1H); 7.03 (t, 2H); 7.14 (s, 1H); 7.32 (m, 3H); 7.38–7.45 (m, 4H); 7.92 (dd, 1H); 8.01 (dd, 1H).

Example 26

8-[(E)-2-[2-(4'-Fluorobenzyloxymethyl)-2,3-dihydrobenzofuran-5-yl]ethen-1-yl]-4-oxo-2-(5-1H-tetrazolyl]-4H-1-benzopyran

26A 8-[(E)-2-[2-(4'-Fluorobenzyloxymethyl)-2,3-dihydrobenzofuran-5-yl]ethen-1-yl]-4-oxo-4H-1-benzopyran-2-carboxamide Following the process described in example 12 (point A), by aminolysis reaction of ethyl 8-[(E)-2-[2-(4'-fluorobenzyloxymethyl)-2,3-dihydrobenzofuran-5-yl]-ethen-1-yl]-4-oxo-4H-1-benzopyran-2-carboxylate, the title compound was prepared as a yellow solid (83% yield).

$^1$H N.M.R. (300 MHz, DMSO) δ ppm: 3.02 (dd, 1H); 3.31 (dd, 1H); 3.67 (m, 2H); 4.55 (s, 2H); 5.04 (m, 1H); 6.81 (d, 1H); 6.93 (s, 1H); 7.17 (t, 2H); 7.35–7.53 (m, 5H); 7.65–7.72 (m, 2H); 7.94 (d, 1H); 8.17 (d, 1H); 8.28 (broad s, 1H); 8.53 (broad s, 1H).

26B 8-[(E)-2-[2-(4'-Fluorobenzyloxymethyl)-2,3-dihydrobenzofuran-5-yl]ethen-1-yl]-4-oxo-4H-1-benzopyran-2-carbonitrile Following the process described in example 2 (point D), by reacting 8-[(E)-2-[2-(4'-fluorobenzyloxymethyl)-2,3-dihydrobenzofuran-5-yl]ethen-1-yl]-4-oxo-4H-1-benzopyran-2-carboxamide with phosphorous oxychloride in DMF for 0.5 h at 0° C., the title compound was prepared (76% yield).

$^1$H N.M.R. (300 MHz, CDCl$_3$) δ ppm: 3.06 (dd, 1H); 3.32 (dd, 1H); 3.67 (m, 2H); 4.55 (d, 1H); 4.61 (d, 1H); 5.03 (m, 1H); 6.80 (s, 1H); 6.82 (d, 1H); 7.03 (t, 2H); 7.16 (d, 1H); 7.26–7.33 (m, 4H); 7.42–7.45 (m, 2H); 7.98 (d, 1H); 8.02 (d, 1H).

26C 8-[(E)-2-[2-(4'-Fluorobenzyloxymethyl)-2,3-dihydrobenzofuran-5-yl]ethen-1-yl]-4-oxo-2-(5-1H-tetrazolyl]-4H-1-benzopyran Following the process described in example 7 (point C), starting from 8-[(E)-2-[2-(4'-fluorobenzyloxymethyl)-2,3-dihydrobenzofuran-5-yl]ethen-1-yl]-4-oxo-4H-1-benzopyran-2-carbonitrile, the title compound was prepared as a yellow solid with melting point 137.5–140.8° C., which was crystallized from pentane:chloroform mixtures and recrystallized in benzene (42% yield).

$^1$H N.M.R. (300 MHz, DMSO) δ ppm: 3.05 (dd, 1H); 3.33 (dd, 1H); 3.67 (m, 2H); 4.55 (s, 2H); 5.04 (m, 1H); 6.84 (d, 1H); 7.11 (s, 1H); 7.18 (t, 2H); 7.35–7.40 (m, 2H); 7.45 (d, 1H); 7.52 (t, 1H); 7.54–7.61 (m, 3H); 7.94 (d, 1H); 8.17 (d, 1H).

Biological Activity Tests

The antagonistic activity on LTD$_4$ of the compounds of the present invention is determined by means of an inhibition test of the [$^3$H]-LTD$_4$ receptor binding in guinea-pig lung membranes.

[$^3$H]-LTD$_4$ Receptor Binding Inhibition Test in Guinea-pig Lung Membranes

Guinea pig lung membranes, containing the LTD$_4$ receptors, are purified following the method described by Mong and col. (Mong et al., *Prostaglandins*, 1984, 28. 805).

These purified membranes (150 μg/ml) are added to an incubation mixture containing 10 mM of PIPES buffer (piperazine-N,N'-bis(2-ethanesulfonic acid) (pH 7.4), 10 mM CaCl$_2$, 10 mM MgCl$_2$, 2 mM cysteine, 2 mM glycine, 0.5 nM [$^3$H]-LTD$_4$ (4700–6400 GBq/mmol) and different concentrations of the product under test in a final volume of 310 μl. The reaction mixture is incubated for 30 minutes at 25° C.

The radioligand bound to the membranes is separated from the free one by dilution with 4 ml washing buffer (10 mM Tris-HCl (pH 7.4) and 100 mM NaCl) at 0° C. and filtration with Whatman GF/B filters, by means of a Brandel Cell Harvester. The filters are washed 4 times with a total volume of 16 ml of washing buffer at 0° C. The radioactivity present in the filters is determined by liquid scintillation.

The specific binding is defined as the difference between the total binding of [$^3$H]-LTD$_4$ and the non-specific binding determined in the presence of 1 μM LTD$_4$. The data obtained in the competition tests are analyzed by a computational program, which determines the inhibition constant of each compound (K$_i$) by means of the Cheng-Prusoff equation (Cheng et al., *Biochem. Pharmacol.*, 1973, 22, 3094).

$$Ki=IC50/(1+[L]/Kd)$$

wherein IC$_{50}$ is the concentration of compound which displaces a 50% of the bound radioligand, [L] is the concentration of [$^3$H]LTD$_4$ free in the test and K$_d$ is the dissociation constant of the LTD$_4$ obtained in an independent way by means of Scatchard analysis.

The selected compounds of general formula I show in the described receptor binding inhibition test inhibition constants (Ki) between 1000 and 0.1 nM. The activity values of some representative compounds are shown in Table 1.

TABLE 1

| Compound Example No | [$^3$H]-LTD$_4$ Receptor binding inhibition Ki (nM) |
|---|---|
| 1 | 145 ± 34 |
| 2 | 12.0 ± 4 |
| 3 | 5.6 ± 0.5 |
| 4 | 2.3 ± 0.2 |
| 5 | 24.0 ± 3 |
| 6 | 6.0 ± 2.1 |
| 7 | 1.88 ± 0.2 |
| 8 | 1.73 ± 0.2 |
| 9 | 1.1 ± 0.2 |
| 10 | 9.0 ± 0.8 |
| 11 | 1.9 ± 0.04 |
| 12 | 0.39 ± 0.1 |
| 13 | 9.3 ± 3 |
| 14 | 4.2 ± 1.1 |
| 15 | 102 ± 48 |
| 16 | 169 ± 24 |
| 17 | 1200 ± 440 |
| 18 | 174 ± 43 |
| 19 | 6.0 ± 1.0 |
| 20 | 6.2 ± 1.3 |
| 21 | 0.5 ± 0.2 |
| 22 | 6.0 ± 3 |
| 23 | 0.39 ± 0.1 |
| 24 | 22.3 ± 0.1 |
| 25 | 1.25 ± 0.3 |
| 26 | 0.46 ± 0.1 |

What is claimed is:

1. A compound of formula I,

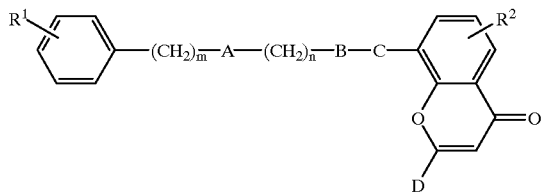

I
wherein:
A is an oxygen or sulfur atom or a methylene group;
B is:
a) a benzofused heterocycle

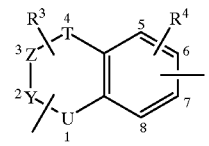

wherein:
U is an oxygen or sulfur atom or a NR$^5$ group, wherein R$^5$ is hydrogen or (C$_1$–C$_4$)-alkyl, the R$^5$ group being optionally replaced by the substituent R$^1$—C$_6$H$_4$—(CH$_2$)$_m$—A—(CH$_2$)$_n$— when said substituent is bound to the 1-position of the benzofused heterocycle;
Z and Y represent two carbon atoms linked together by a single bond or by a double bond;
T is a single bond, a methylene group or a carbonyl group; and wherein:
the substituent containing A is bound to any one of the possible 1-, 2-, 3- or 4-position of the benzofused heterocycle;
the substituent containing C is bound to the 6- or 7-position of the benzofused heterocycle; or
b) a phenyl group

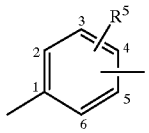

wherein the substituent containing C is bound to the phenyl group at the 3-, 4- or 5-position;
C is a diradical which represents:
a) when B is a benzofused heterocycle, a —CONR$^7$—, —CSNR$^7$—, —SO$_2$NR$^7$—, —CH$_2$O—, —CH═CH— group, wherein R$^7$ is hydrogen or methyl; or
b) when B is a phenyl group, a —SO$_2$NR$^7$—, —CH$_2$O—, —CH═CH— group, wherein R$^7$ is hydrogen or methyl;
D is a 5-tetrazolyl or —COOR$^8$ group, wherein R$^8$ is hydrogen, a (C$_1$–C$_4$)-alkyl or a phenylalkyl group of less than 10 carbon atoms;
R$^1$, R$^2$, R$^3$, R$^4$ and R$^6$ are independently hydrogen, halogen, (C$_1$–C$_4$)-alkyl, —OCH$_3$ or —OH;
m and n are integers from 0 to 4; or solvate, pharmaceutically acceptable salts, steroisomer, or mixtures thereof.

2. A compound according to claim 1, wherein $R^1$ and $R^2$ are hydrogen, fluorine or chlorine and D is a 5-tetrazolyl or $COOR^8$ group, wherein $R^8$ is hydrogen, methyl, ethyl or benzyl.

3. A compound according to claim 1, wherein B is a benzofused heterocycle, and C is —$CONR^7$— or —CH═CH—.

4. A compound according to claim 3, wherein $R^3$ is hydrogen or methyl and U is a $NR^5$ group, wherein $R^5$ is hydrogen or methyl or ($R^1$—$C_6H_4$—$(CH_2)_m$—A—$(CH_2)_n$—.

5. A compound according to claim 3, wherein $R^3$ is hydrogen, $R^4$ is hydrogen, fluorine, chlorine, methyl or methoxy and U is oxygen.

6. A compound according to claim 3, wherein the substituent containing C is bound to the 6-position of the central benzofused heterocycle.

7. A compound according to claim 4, wherein T is a single bond or a carbonyl group, Y—Z is a —CH═CH— group and the substituent containing A is bound to the 1- or 2-position of the central benzofused heterocycle.

8. A compound according to claims 5, wherein the substituent containing A is bound to the 2-position of the central benzofused heterocycle.

9. A compound according to any one of claims 3, wherein m and n are integers from 1 to 2.

10. A compound according to claims 1, wherein B is a substituted phenyl and C is —CH═CH—, —$CH_2O$— or —$SO_2NR^7$—, wherein $R^7$ is hydrogen or methyl.

11. A compound according to claim 10, wherein the substituents containing A and C are bound to the phenyl group in a respective para position.

12. A compound according to claims 10, wherein $R^6$ is hydrogen, fluorine, chlorine, methyl or methoxy, n is 0, A is oxygen or sulfur and m is 3.

13. A compound according to claim 1 selected from the following ones:

8-[2-(benzyloxymethyl)chromane-6-carboxamido]-4-oxo-4H-1-benzopyran-2-carboxylic acid;

N-[4-oxo-2-(1H-5-tetrazolyl)-4H-1-benzopyran-8-yl]-2-(benzyloxymethyl)chromane-6-carboxamide;

8-[2-(3-phenylpropyl)chromane-6-carboxamido]-4-oxo-4H-1-benzopyran-2-carboxylic acid;

N-[4-oxo-2-(1H-5-tetrazolyl)-4H-1-benzopyran-8-yl]-2-(3-phenylpropyl)chromane-6-carboxamide;

8-[2-(benzyloxymethyl)benzofuran-5-carboxamido]-4-oxo-4H-1-benzopyran-2-carboxylic acid;

8-(2-benzyloxymethyl-2,3-dihydrobenzofuran-5-carboxamido)-4-oxo-4H-1-benzopyran-2-carboxylic acid;

N-[4-oxo-2-(1H-5-tetrazolyl)-4H-1-benzopyran-8-yl]-2-benzyloxymethyl-2,3-dihydrobenzofuran-5-carboxamide;

8-[2-(3-phenylpropyl)-2,3-dihydrobenzofuran-5-carboxamido]-4-oxo-4H-1-benzopyran-2-carboxylic acid;

N-[4-oxo-2-(1H-5-tetrazolyl)-4H-1-benzopyran-8-yl]-2-(3-phenylpropyl)-2,3-dihydrobenzofuran-5-carboxamide;

8-(2-benzylthiomethyl-2,3-dihydrobenzofuran-5-carboxamido)-4-oxo-4H-1-benzopyran-2-carboxylic acid;

8-[2-(4'-fluorobenzyloxymethyl)-2,3-dihydrobenzofuran-5-carboxamido]-4-oxo-4H-1-benzopyran-2-carboxylic acid;

N-[4-oxo-2-(1H-5-tetrazolyl)-4H-1-benzopyran-8-yl]-2-(4'-fluorobenzyloxymethyl)-2,3-dihydrobenzofuran-5-carboxamide;

8-[7-chloro-2-(3-phenylpropyl)-2,3-dihydrobenzofuran-5-carboxamido]-4-oxo-4H-1-benzopyran-2-carboxylic acid;

8-[2-(3-phenylpropyl)-2,3-dihydrobenzofuran-5-carboxamido]-6-fluoro-4-oxo-4H-1-benzopyran-2-carboxylic acid;

8-[4-chloro-2-(3-phenylpropyl)-2,3-dihydrobenzofuran-5-carboxamido]-4-oxo-4H-1-benzopyran-2-carboxylic acid;

8-[6-chloro-2-(3-phenylpropyl)-2,3-dihydrobenzofuran-5-carboxamido]-4-oxo-4H-1-benzopyran-2-carboxylic acid;

N-[4-oxo-2-(1H-5-tetrazolyl)-4H-1-benzopyran-8-yl]-1-(4-phenylbutyl)-3-methylindole-5-carboxamide;

8-[[4-(4-phenylbutoxy)phenyl]methyloxy]-4-oxo-4H-1-benzopyran-2-carboxylic acid;

8-[[4-(4-phenylbutoxy)phenyl]sulfonylamino]-4-oxo-4H-1-benzopyran-2-carboxylic acid;

8-[(E)-2-[4-(4-phenylbutoxy)phenyl]ethen-1-yl]-4-oxo-4H-1-benzopyran-2-carboxylic acid;

8-[(E)-2-[4-(4-phenylbutoxy)phenyl]ethen-1-yl]-4-oxo-2-(5-1H-tetrazolyl)-4H-1-benzopyran;

8-[(E)-2-[4-[4-(4-fluorophenyl)butoxy]phenyl]ethen-1-yl]-4-oxo-4H-1-benzopyran-2-carboxylic acid;

8-[(E)-2-[4-[4-(4-fluorophenyl)butoxy]phenyl]ethen-1-yl]-4-oxo-2-(5-1H-tetrazolyl)-4H-1-benzopyran;

8-[(E)-2-[4-(4-phenylbutoxy)-2-fluorophenyl]ethen-1-yl]-4-oxo-4H-1-benzopyran-2-carboxylic acid;

8-[(E)-2-[2-(4'-fluorobenzyloxymethyl)-2,3-dihydrobenzofuran-5-yl]ethen-1-yl]-4-oxo-4H-1-benzopyran-2-carboxylic acid;

8-[(E)-2-[2-(4'-fluorobenzyloxymethyl)-2,3-dihydrobenzofuran-5-yl]ethen-1-yl]-4-oxo-2-(5-1H-tetrazolyl)-4H-1-benzopyran;

8-[(E)-2-[4-[4-(4-chlorophenyl)butoxy]phenyl]ethen-1-yl]-4-oxo-2-(5-1H-tetrazolyl)-4H-1-benzopyran;

8-[(E)-2-[4-[4-(4-methylphenyl)butoxy]phenyl]ethen-1-yl]-4-oxo-2-(5-1H-tetrazolyl)-4H-1-benzopyran;

8-[(E)-2-[4-[4-(4-methoxyphenyl)butoxy]phenyl]ethen-1-yl]-4-oxo-2-(5-1H-tetrazolyl)-4H-1-benzopyran;

8-[(E)-2-[4-[4-[4-(iso-propyl)phenyl]butoxy]phenyl]-ethen-1-yl]-4-oxo-2-(5-1H-tetrazolyl)-4H-1-benzopyran;

8-[(E)-2-[4-[4-[4-(tert-butyl)phenyl]butoxy]phenyl]-ethen-1-yl]-4-oxo-2-(5-1H-tetrazolyl)-4H-1-benzopyran;

8-[(E)-2-[4-[4-(4-chlorophenyl)propyloxy]phenyl]ethen-1-yl]-4-oxo-2-(5-1H-tetrazolyl)-4H-1-benzopyran;

8-[(E)-2-[4-[4-(4-fluorophenyl)propyloxy]phenyl]ethen-1-yl]-4-oxo-2-(5-1-tetrazolyl)-4H-1-benzopyran;

8-[(E)-2-[4-[4-(4-methylphenyl)propyloxy]phenyl]ethen-1-yl]-4-oxo-2-(5-1H-tetrazolyl)-4H-1-benzopyran;

8-[(E)-2-[4-[4-(4-methoxyphenyl)propyloxy]phenyl]ethen-1-yl]-4-oxo-2-(5-1H-tetrazolyl)-4H-1-benzopyran;

8-[(E)-2-[4-[4-[4-(iso-propyl)phenyl]propyloxy]phenyl]-ethen-1-yl]-4-oxo-2-(5-1H-tetrazolyl)-4H-1-benzopyran; and 8[(E)-2-[4-[4-[4-(tert-butyl)phenyl]propyloxy]phenyl]-ethen-1-yl]-4-oxo-2-(5-1H-tetrazolyl)-4H-1-benzopyran.

14. A process for the preparation of the compounds of general formula I of claim 1, and the pharmaceutically acceptable salt thereof, in which process:

a) when in general formula I D is —COOR⁸, a compound of general formula II,

II
wherein $R^1$, $R^2$, A, B, C, m and n have the above mentioned meanings, is reacted with a commercial compound III,

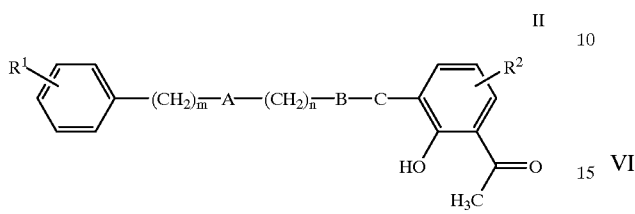

III
wherein $R^9$ is the residue $R^8$ with the exception of hydrogen, in the presence of a base, to obtain a compound IV,

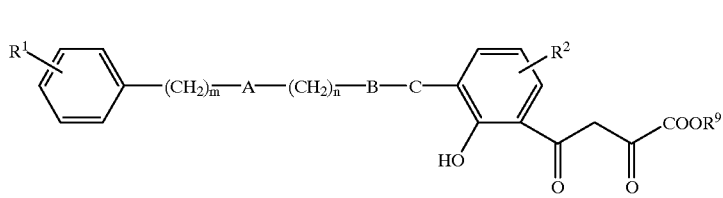

IV which is subjected to an acid treatment to obtain compound V,

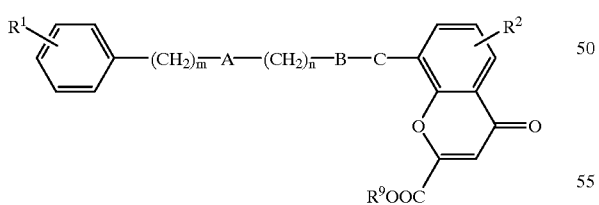

V which coincides with I wherein D is COOR⁸ or, when D is COOH in formula I, is converted into I by cleavage of the $R^9$ group through alkali hydrolysis;

b) when in general formula I D is a 5-tetrazolyl group, a compound of formula VI,

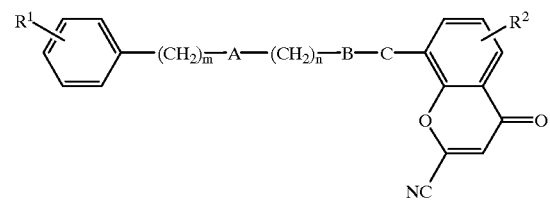

VI wherein $R^1$, $R^2$, A, B, C, m and n have the above mentioned meanings, is reacted with sodium azide to obtain a compound VII,

VII which coincides with I wherein D is the 5-tetrazolyl group;

c) alternatively, when in general formula I C is —CO—NR⁷—, then a compound VIII,

VIII wherein $R^1$, A, B, m and n have the above mentioned meanings, is reacted with a compound IX,

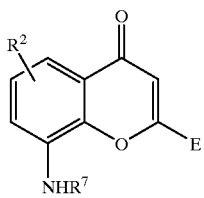

IX
wherein $R^2$ and $R^7$ have the above mentioned meanings and E can be equivalent to the group D in I or, when D in formula I is COOH, then E contains a suitable carboxy-protecting group, the reaction being carried out previously preparing the acid chloride of the compound VIII according to conventional processes, then reacting it with compound IX in the presence of a base, to obtain thereby a compound of formula X,

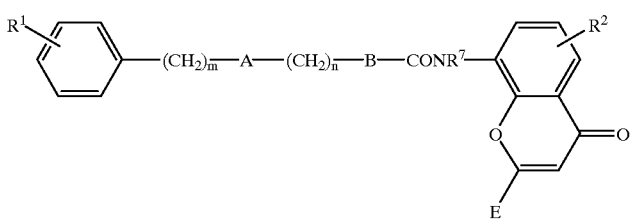

X which coincides with I, wherein C is —$CONR^7$— or is converted in I, wherein C is —$CONR^7$—, removing any COOH-protecting group present in E;

d) when in general formula I C is —$CH_2O$—, then a compound of formula XI,

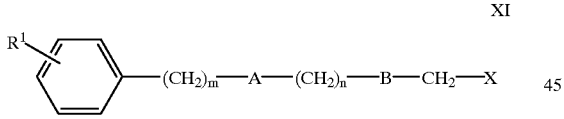

XI
wherein $R^1$, A, B, m and n have the above mentioned meanings and X is a chlorine or bromine atom or an alkyl- or aryl- sulfonate group, is reacted with a compound XII,

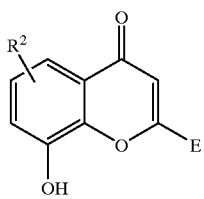

XII
wherein $R^2$ and E have the above mentioned meanings, in the presence of a base, to obtain a compound of formula XIII,

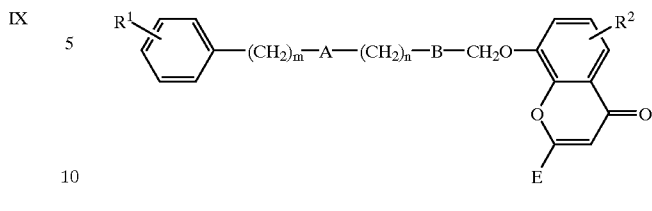

XIII which coincides with I, wherein C is —$CH_2O$— or is converted into I wherein C is —$CH_2O$— removing any COOH-protecting groups present in E;

e) when in formula I C is —$SO_2NR^7$— and A is oxygen or sulfur, then a compound XIV,

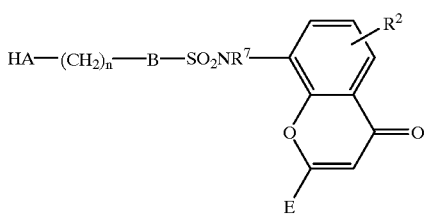

XIV
wherein $R^2$, $R^7$, B, E and n have the above mentioned meanings and A is an oxygen or sulfur atom, is reacted with a compound XV,

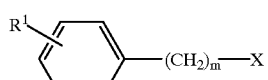

XV
wherein $R^1$, X and m have the above mentioned meanings, in the presence of a base to obtain a compound XVI,

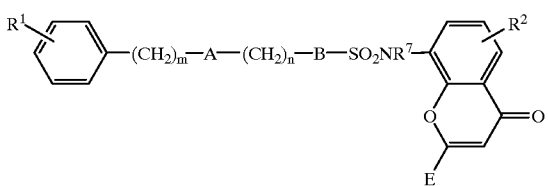

XVI which coincides with I, wherein C is —SO$_2$NR$^7$— and A is oxygen or sulfur, or is converted into I, wherein C is —SO$_2$NR$^7$— and A is oxygen or sulfur, removing any COOH-protecting groups present in E; or f) and, if necessary, the compound of formula I is converted into the desired salt, by treatment with a base or a suitable ion exchanger according to conventional methods.

15. A method for the treatment of leukotriene-mediated diseases in a patient requiring such treatment which comprises administering to such patient an effective amount of a compound of claim 1.

16. The method of claim 15, wherein the leukotriene-mediated diseases are of inflammatory or allergic type.

17. The method of claim 16, wherein the inflammatory or allergic diseases are: bronchial asthma, allergic rhinitis, allergic conjunctivitis, rheumatoid arthritis, osteoarthritis, tendonitis, bursitis, or psoriasis.

18. The method of claim 15, wherein the leukotriene-mediated diseases are of cardiovascular type.

19. The method of claim 18, wherein the diseases of cardiovascular type are: cardiac ischemia, cardiac infarction, coronary spasm, cardiac anaphylaxis, cerebral edema, or endotoxic shock.

* * * * *